US012528870B2

(12) United States Patent
Fang et al.

(10) Patent No.: US 12,528,870 B2
(45) Date of Patent: Jan. 20, 2026

(54) ANTI-C-MET ANTIBODY-DRUG CONJUGATE AND APPLICATIONS THEREOF

(71) Applicant: REMEGEN CO., LTD., Yantai (CN)

(72) Inventors: Jianmin Fang, Yantai (CN); Changjiang Huang, Yantai (CN); Xuejing Yao, Yantai (CN); Wenting Luo, Yantai (CN)

(73) Assignee: REMEGEN CO., LTD., Yantai (CN)

( * ) Notice: Subject to any disclaimer, the term of this patent is extended or adjusted under 35 U.S.C. 154(b) by 667 days.

(21) Appl. No.: 17/797,720

(22) PCT Filed: Aug. 31, 2021

(86) PCT No.: PCT/CN2021/115490

§ 371 (c)(1),
(2) Date: Aug. 5, 2022

(87) PCT Pub. No.: WO2022/048521

PCT Pub. Date: Mar. 10, 2022

(65) Prior Publication Data

US 2024/0165253 A1 May 23, 2024

(30) Foreign Application Priority Data

Sep. 1, 2020 (WO) ................ PCT/CN2020/112919
Sep. 2, 2020 (CN) ......................... 202010918330.4

(51) Int. Cl.

| | |
|---|---|
| ***A61P 35/00*** | (2006.01) |
| ***A61K 47/54*** | (2017.01) |
| ***A61K 47/68*** | (2017.01) |
| ***A61P 1/00*** | (2006.01) |
| ***A61P 11/00*** | (2006.01) |
| ***C07K 16/28*** | (2006.01) |

(52) U.S. Cl.

CPC ........ *C07K 16/2863* (2013.01); *A61K 47/545* (2017.08); *A61K 47/68031* (2023.08); *A61K 47/6817* (2017.08); *A61K 47/6849* (2017.08); *A61P 1/00* (2018.01); *A61P 11/00* (2018.01); *A61P 35/00* (2018.01); *C07K 2317/24* (2013.01); *C07K 2317/31* (2013.01)

(58) Field of Classification Search

None
See application file for complete search history.

(56) References Cited

U.S. PATENT DOCUMENTS

| | | | |
|---|---|---|---|
| 9,101,610 | B2 | 8/2015 | Cheong et al. |
| 10,543,284 | B2 | 1/2020 | Liu et al. |
| 2010/0129369 | A1 | 5/2010 | Davies et al. |
| 2011/0239316 | A1 | 9/2011 | Goetsch et al. |
| 2012/0148607 | A1 | 6/2012 | Hultberg et al. |
| 2013/0102494 | A1 | 4/2013 | Jouhanneaud |
| 2014/0115727 | A1 | 4/2014 | Goetsch et al. |
| 2018/0110875 | A1 | 4/2018 | Liu et al. |
| 2020/0054764 | A1 | 2/2020 | Sun et al. |
| 2020/0061204 | A1 | 2/2020 | Feng et al. |
| 2020/0138968 | A1 | 5/2020 | Huang et al. |
| 2021/0087277 | A1 | 3/2021 | Fang et al. |
| 2021/0403576 | A1 | 12/2021 | Jeong et al. |
| 2022/0072137 | A1 | 3/2022 | Huang et al. |

FOREIGN PATENT DOCUMENTS

| | | | |
|---|---|---|---|
| CN | 103562223 | A | 2/2014 |
| CN | 104628867 | A | 5/2015 |
| CN | 108853514 | A | 11/2018 |
| CN | 109541221 | A | 3/2019 |
| CN | 109771642 | A | 5/2019 |
| CN | 111433188 | A | 7/2020 |
| EA | 020398 | B1 | 10/2014 |
| JP | 2018516539 | A | 6/2018 |
| RU | 2607377 | C2 | 1/2017 |
| WO | 2010064089 | A1 | 6/2010 |
| WO | 2010069765 | A1 | 6/2010 |
| WO | 2011020925 | A1 | 2/2011 |
| WO | 2012007280 | A1 | 1/2012 |
| WO | 2018098035 | A1 | 5/2018 |
| WO | 2019034177 | A1 | 2/2019 |
| WO | 2019091306 | A1 | 5/2019 |
| WO | 2019175186 | A1 | 9/2019 |
| WO | 2019223579 | A1 | 11/2019 |
| WO | 2020101365 | A1 | 5/2020 |
| WO | 2020108612 | A1 | 6/2020 |
| WO | 2020125546 | A1 | 6/2020 |

OTHER PUBLICATIONS

Russian Patent Office, first office Action Issued in Application No. 2022117360, Aug. 29, 2023, 24 pages.
O.N. Solopova and V.A. Misyurin, Bispecific Antibodies in Clinical Practice and Clinical Trials (Literature Review), Clinical Oncohematology. 2019, 12(2), pp. 125-144.
B.Tran and M.A.Rosenthal, Survival comparison between glioblastoma multiforme and other incurable cancers,Journal of Clinical Neuroscience, 2010, vol. 17, pp. 417-421.
Japanese Patent Office, first office action Issued in Application No. 2022-565937, Sep. 19, 2023, 8 pages.

(Continued)

*Primary Examiner* — Ruixiang Li

(74) *Attorney, Agent, or Firm* — Kilpatrick Townsend & Stockton LLP

(57) ABSTRACT

The present disclosure relates to the technical field of c-Met antibody drugs, specifically to a c-Met-targeted antibody-drug conjugate and applications thereof. The antibody-drug conjugate of the present disclosure comprises an antibody conjugated with one or more therapeutic agents or antigen-binding fragments of the antibody, is able to effectively inhibit the growth of a tumor tissue, provides a significant inhibitory effect with respect to c-Met-positive cancer, and has excellent safety.

33 Claims, 6 Drawing Sheets

Specification includes a Sequence Listing.

(56) References Cited

OTHER PUBLICATIONS

Zhang, Longzhen et al. "Construction of Chimeric Anti-c-Met Antibody and Its Rapid Expression Using Lentiviral Vector", Journal of Hefei University ofT echnology(Natural Science), vol. 40, No. 6, Jun. 30, 2017 pp. 835-839.
Guo. Jia et al. "Construction of Chimeric Anti-c-Met Antibody Random Mutagenesis Libraries Using Mammalian Cell Surface Display", Chinese Journal of Cellular and Molecular Immunology, vol. 35, No. 6, Dec. 31, 2019, pp. 557-562.
Guo, Jia et al., "Preparation and Biological Activity of Anti-human C-mesenchymal Epithelial Transition Factor(c-Met) Monovalent Antibody)", Chinese Journal of Cellular and Molecular Immunology, vol. 32, No. 11, Dec. 31, 2016, pp. 1544-1553.
Yin, Y.X et al. "Preparation of a Novel One-Armed Anti-c-Met Antibody with Antitumor Activity Against Hepatocellular Carcinoma" Drug Design, Development and Therapy, vol. 13, Dec. 10, 2019 (Dec. 10, 2019), pp. 4173-4184.
Huang, L. et al. "Suppression of c-Met-Overexpressing Tumors by a Novel c-Met/CD3 Bispecific Antibody" Drug Design, Development and Therapy, vol. 14, Aug. 7, 2020 (Aug. 7, 2020), pp. 3201-3214.
Genichiro Edakuni et al., "Expression of the hepatocyte growth factor/c-Met pathway is increased at the cancer front in breast carcinoma", Pathology International , Nov. 10, 2000, pp. 172-178.
Martin Sattler et al., " The role of the C-Met pathway in lung cancer and the potential for targeted therapy", Therapeutic Advances in Medical Oncology, pp. 171-184.
Benedetta Peruzzi et al.,"Targeting the c-Met Signaling Pathway in Cancer", Molecular Pathways, Clin Cancer Res 2006;12; pp. 3657-3660.
Ki-Hyun Kim et al.,"Progress of antibody-based inhibitors of the HGF-cMET axis in cancer therapy", Experimental & Molecular Medicine, Mar. 24, 2017, total 7 pages.
Jieyi Wang et al.,"ABBV-399, a c-Met Antibody-Drug Conjugate that Targets Both MET-Amplified and c-Met-Overexpressing Tumors, Irrespective of MET Pathway Dependence", Clinical Cancer Rearch; 23(4) Feb. 15, 3.28 total 9 pages.
E.Angevin et al., "First-in-human phase 1, dose-escalation and -expansion study of ABBV-399, an antibody-drug conjugate (ADC) targeting c-Met, in patients (pts) with advanced solid tumors", Annals of Oncology 27 (Supplement 6): vi114-vi135, 2016, total 1 page.
European Patent Office, the Extended European Search Report Issued in Application No. 21863586.0, Mar. 22, 2024, Germany, 7 pages.

ANTI-C-MET ANTIBODY-DRUG CONJUGATE AND APPLICATIONS THEREOF

CROSS-REFERENCE OF RELATED APPLICATIONS

The present application is the national phase of International Application No. PCT/CN2021/115490, titled "ANTI-C-MET ANTIBODY-DRUG CONJUGATE AND APPLICATIONS THEREOF", filed on Aug. 31, 2021, which claims priority to PCT/CN2020/112919, filed on Sep. 1, 2020 with the World Intellectual Property Organization, which claims priority to Chinese Patent Application No. CN202010918330.4, filed on Sep. 2, 2020 with the China National Intellectual Property Administration, which are incorporated herein by reference in their entireties.

FIELD

The present disclosure relates to the field of antibody-drug conjugates, and specifically relates to an antibody-drug conjugate targeting c-Met and applications thereof.

BACKGROUND c-Met (tyrosine-protein kinase Met) is a proto-oncogene (Reference 1: Edakuni G, Sasatomi E, Satoh T, et al. Expression of the hepatocyte growth factor/c-Met pathway is increased at the cancer front in breast carcinoma. [J]. Pathology International, 2010, 51 (3): 172-178), and the post-transcriptional product is hepatocyte growth factor (HGF) receptor. Consistent with HGF, its precursor is a single chain, which is broken into a chain and β chain connected by disulfide bonds after various modifications. Cellularly, c-Met is mainly divided into intracellular and extracellular parts. For β chain, the extracellular region includes SD (Sema domain), PSID (plexin-semaphorin-integrin domain) and IPTD (immunoglobulin-like regions in plexins and transcription factors domain), and the intracellular region mainly includes JD (juxtamembrane domain) and TKCD (a tyrosine kinase domain (TK domain) and a c-terminal docking site) (Reference 2: Sattler M, Reddy M, Hasina R, et al. The role of the c-Met pathway in lung cancer and the potential for targeted therapy [J]. Therapeutic Advances in Medical Oncology, 2011, 3(4):171-84.). c-Met is the receptor of HGF. When HGF binds to c-Met, the structure of c-Met is changed, which activates the intracellular protein tyrosine kinase, resulting in the phosphorylation of itself, mainly the phosphorylation of Try1235 and Try1234. Upon activation of c-Met, Try1349 and Try1256 at the end of the β chain are phosphorylated (Reference 3: Peruzzi B, Bottaro D P. Targeting the c-Met Signaling Pathway in Cancer [J]. Clinical Cancer Research, 2006, 12(12):3657-3660). When HGF binds to c-Met, multiple signaling pathways are triggered: (1) Ras-Rac signaling pathway leads to the movement of the cytoskeleton; (2) Ras-MAPK cascade promotes cell division and differentiation; (3) PI3K-FAK signaling pathway promotes cell migration and invasion; and (4) PI3K-AKT signaling pathway promotes cell survival. The HGF/c-Met signaling pathway promotes growth and migration of tumor cells.

c-Met is overexpressed on many tumor cells, mainly head and neck squamous carcinoma and hypopharyngeal carcinoma, but also on renal cell carcinoma, colorectal cancer, lung adenocarcinoma, ovarian cancer, liver cancer, breast cancer, bladder cancer, non-small cell carcinoma and gastric cancer. The high expression in tumor cells and low expression in normal cells of c-Met makes c-Met an excellent target for targeted therapy.

Antibody-drug conjugate (ADC) is a biological drug that links a biologically active drug and an antibody through a chemical linker. In recent years, a number of antibody-drug conjugates have made breakthroughs in the treatment of malignant tumors, making them a major emerging treatment method after surgery, chemotherapy and radiotherapy. However, as of March 2021, only 11 antibody conjugated drugs have been approved in the world (10 have been approved by the US FDA, and one has been approved by the Japanese PMDA), and there are only a few approved indications, which are far from meeting the current clinical needs of patients with malignant tumors.

TABLE 1

Marketed antibody-drug conjugates

| Generic name | Companies | Target | Time to market |
|---|---|---|---|
| Brentuximab vedotin | Seattle, Takeda | CD30 | 2011 |
| Ado-trastuzumab emtansine | Genentech | Her2 | 2013 |
| Inotuzumab ozogamicin | Pfizer | CD22 | 2017 |
| Gemtuzumab ozogamicin | Pfizer | CD33 | 2017 |
| Moxetumomab pasudotox-tdfk | AstraZeneca | CD22 | 2018 |
| Enfortumab vedotin-ejfv | Seattle/Astellas | Nectin-4 | 2019 |
| Polatuzumab vedotin-piiq | Genentech | CD79b | 2019 |
| Fam-trastuzumab deruxtecan-nxki | AstraZeneca/Daiichi Sankyo | Her2 | 2019 |
| Sacituzumab govitecan-hziy | Immunomedics | Trop2 | 2020 |
| Belantamab mafodotin | Glaxosmithkline (Ireland) Ltd | BCMA | 2020 |
| Cetuximab sarotalocan | Rakuten Medical | EGFR | 2020 |

Note:
Mylotarg was withdrawn from the market in 2010 after being approved for marketing in 2000, and was re-approved for marketing in 2017.

At present, the biological drugs targeting c-Met in the research or clinical stage are mainly monoclonal antibodies, and there are few antibody-drug conjugates (ADC) (Reference 4: LILIANE GOETSCH, A. J. Anti-CMET antibody and its use for the detection and the diagnosis of cancer. WO2011020925 A1, 2012). Among them, SHR-A1403 for injection developed by Hengrui Medicine is an ADC formed by chemical coupling of a humanized anti-c-Met monoclonal antibody and a microtubule inhibitor. By binding to c-Met on the surface of tumor cells, this antibody-drug conjugate can be endocytosed into tumor cells, and then release small molecule toxins after degradation in lysosome, which plays a role in killing tumor cells (Reference 5: Ki-Hyun Kim Progress of antibody-based inhibitors of the HGF-cMET axis in cancer therapy, Experimental & Molecular Medicine (2017) 49, e307). SHR-A1403 was approved by the FDA for clinical trials in the United States in January 2017. According to the FDA official website (https://clinicaltrials.gov/ct2/show/NCT03856541?term=SHR-A1403&rank=1), the Phase I clinical trial is currently in the process of recruiting patients.

ABBVie's ABBV-399 is also in phase I clinical research in the United States. It is a conjugate of ABT-700 antibody and MMAE with a DAR (drug-to-antibody ratio) of 3.1 for the treatment of c-Met-overexpressing non-small cell lung cancer. The results of early clinical trials of c-Met showed that ABBV-399 can produce cytotoxic effect on c-Met positive cancer cells. The phase I clinical trial (NCT02099058) was conducted in 29 patients with c-Met-positive NSCLC, and the safety and efficacy of ABBV-399 alone or in combination with erlotinib were preliminarily investigated. In the single administration cohort, >10% of patients experienced adverse reactions, mainly fatigue, nausea, neuralgia, and nausea (43.8%, 37.5%, 25%, and 18.8%, respectively). In the single administration group, 3/16 patients experienced partial remission, lasting between 3.1 and 11.1 months. After 12 weeks of administration, 56.3% of patients in the single administration group were under control. In the combined administration group, >10% of patients also experienced adverse reactions, mainly neuralgia and nausea (46.2 and 23.1%, respectively). Partial remission occurred in 4/13 patients in this group, of which 1 remains to be confirmed, lasting between 2.8 to 9.1 months. After 12 weeks of treatment, 76.9% of patients in the combined administration group were under control. There were no treatment-related deaths in either the single administration group or the combined administration group. The trial results confirmed that ABBV-399 was well tolerated at a dose of 2.7 mg/kg, and showed good anti-tumor activity in HGF-positive NSCLC patients (Reference 6: Wang J, Anderson M G, Oleksijew A, et al. al. ABBV-399, a c-Met Antibody-drug conjugate that Targets Both MET Amplified and c-Met Overexpressing Tumors, Irrespective of MET Pathway Dependence [J]. Clinical Cancer Research, 2016, 23(4):992-1000.). According to the latest data released by ABBVie in 2016, about 19% of NSCLC patients with H-score ≥150 experienced partial remission after treatment with ABBV-399. The tolerated dose of ABBV-399 was 2.7 mg/kg every three weeks, and the most frequently occurring toxicities were fatigue (25%), nausea (23%), neuralgia (15%), decreased appetite (13%), vomiting (13%), and diarrhea (10%) (Reference 7: Angevin E, Kelly K, Heist R, et al. First-in-human phase 1, dose-escalation and -expansion study of ABBV-399, an antibody-drug conjugate (ADC) targeting c-Met, in patients (pts) with advanced solid tumors [J]. Annals of Oncology, 2016, 27(suppl 6).

Although dozens of antibodies targeting c-Met are currently in clinical stage, the tumor curative effect is not satisfactory. ADC drugs can effectively combine these well-targeted monoclonal antibodies and cytotoxins to maintain targeting while enhancing the killing effect on cells. Currently, the development of ADCs targeting c-Met is relatively slow, few in the clinical stage, and they are in the early clinical stage, such as ABBVie's ABBV-399 and Hengrui Medicine's SHR-A1403, both of which are in phase I clinical trials. The safety of drugs and effective targeted indications are still under exploration. Therefore, there is an urgent need to develop anti-c-Met antibody-drug conjugates with better efficacy and safety in clinical practice, and more targeted indications can be expanded for effective treatment.

SUMMARY

The present disclosure provides an antibody targeting c-Met or antigen-binding fragment thereof and use thereof in the treatment of cancer. The present disclosure also provides an antibody-drug conjugate (ADC) including the above-mentioned antibody, a nucleotide encoding the above-mentioned c-Met antibody, a polynucleotide combination, an expression vector and a host cell, a pharmaceutical composition including the above-mentioned antibody targeting c-Met or antibody-drug conjugate, as well as their use in the manufacture of a medicament for the treatment or prevention of a cancer.

Specifically, the present disclosure provides a humanized antibody targeting c-Met or antigen-binding fragment thereof, including a heavy chain variable region and a light chain variable region, and:

(1) the heavy chain variable region has a sequence shown in SEQ ID NO: 7, or a sequence that has the same CDRs 1-3 as SEQ ID NO: 7 and an identity of greater than 80%, 85%, 90%, 95%, 96%, 97%, 98% or 99% to SEQ ID NO: 7; and/or (2) the light chain variable region has a sequence shown in SEQ ID NO: 8, or a sequence that has the same CDRs 1-3 as SEQ ID NO: 8 and an identity of greater than 80%, 85%, 90%, 95%, 96%, 97%, 98% or 99% to SEQ ID NO: 8.

In some embodiments, the humanized antibody or antigen-binding fragment thereof is selected from the group consisting of monoclonal antibody, bispecific antibody, multispecific antibody, recombinant protein including the antigen-binding fragment, Fab 5 fragment, F(ab') fragment, F(ab') 2 fragment, FIT fragment, dAb, Fd, and single chain antibody (scFv).

In some embodiments, the antibody or antigen-binding fragment further comprises a constant region of an immunoglobulin, and the immunoglobulin is selected from the group consisting of IgG1, IgG2, IgG3 and IgG4.

In some specific embodiments, the heavy chain variable region of the antibody or antigen-binding fragment thereof has an amino acid sequence shown in SEQ ID NO: 7; and/or the light chain variable region of the antibody or antigen-binding fragment thereof has an amino acid sequence shown in SEQ ID NO: 8.

The amino acid sequence shown in SEQ ID NO: 7 is as follows:

```
QVQLEQSGPE VVKPGASVKV SCKASGYSFT          60
SYWMHWVRQA PGQGLEWMGM IDPSDSESRL

NQKFKDRVTM TVDTPTSTVY MELSSPRSED         120
TAVYYCARSG YHGTSYWYFD VWGQGTLVTV

SS                                       122
```

The amino acid sequence shown in SEQ ID NO: 8 is as follows:

```
DIVMTQSPLS LPVTPGEPAS ISCRSSKSLL          60
HSDGITYLYW YLQKPGQSPQ LLIYQMSNLA

SGVPDRFSGS GSGTDFTLKI SRVEAEDVGV         115
YYCAQNLELP PTFGGGTKVE IKRTV
```

In other specific embodiments, the heavy chain variable region of the antibody or antigen-binding fragment thereof has an amino acid sequence shown in SEQ ID NO: 9; and/or the light chain variable region of the antibody or antigen-binding fragment thereof has an amino acid sequence shown in SEQ ID NO: 10.

The amino acid sequence shown in SEQ ID NO: 9 is as follows:

```
QVQLEQSGPE VVKPGASVKV SCKASGYSFT          60
SYWMHWVRQA PGQGLEWMGM IDPSDSESRL

NQKFKDRVTM TVDTPTSTVY MELSSPRSED         120
TAVYYCARSG YHGTSYWYFD VWGQGTLVTV
```

-continued

```
SSASTKGPSV FPLAPSSKST SGGTAALGCL        180
VKDYFPEPVT VSWNSGALTS GVHTFPAVLQ

SSGLYSLSSV VTVPSSSLGT QTYICNVNHK        240
PSNTKVDKKV EPKSCDKTHT CPPCPAPELL

GGPSVFLFPP KPKDTLMISR TPEVTCVVVD        300
VSHEDPEVKF NWYVDGVEVH NAKTKPREEQ

YNSTYRVVSV LTVLHQDWLN GKEYKCKVSN        360
KALPAPIEKT ISKAKGQPRE PQVYTLPPSR

EEMTKNQVSL TCLVKGFYPS DIAVEWESNG        420
QPENNYKTTP PVLDSDGSFF LYSKLTVDKS

RWQQGNVFSC SVMHEALHNH YTQKSLSLSP        452
GK
```

The amino acid sequence shown in SEQ ID NO: 10 is as follows:

```
DIVMTQSPLS LPVTPGEPAS ISCRSSKSLL         60
HSDGITYLYW YLQKPGQSPQ LLIYQMSNLA

SGVPDRFSGS GSGTDFTLKI SRVEAEDVGV        120
YYCAQNLELP PTFGGGTKVE IKRTVAAPSV

FIFPPSDEQL KSGTASVVCL LNNFYPREAK        180
VQWKVDNALQ SGNSQESVTE QDSKDSTYSL

SSTLTLSKAD YEKHKVYACE VTHQGLSSPV        219
TKSFNRGEC
```

The present disclosure also relates to an isolated polynucleotide encoding the antibody or antigen-binding fragment thereof described in any one of the above.

The present disclosure also relates to a nucleic acid construct including the above-described polynucleotide.

The above-described nucleic acid construct is preferably an expression vector, and the polynucleotide is operably linked to a regulatory sequence that permits expression of a polypeptide encoded by the polynucleotide in a host cell or cell-free expression system.

The present disclosure also relates to a host cell including the above-described polynucleotide or expression vector, and the host cell is preferably selected from the group consisting of a prokaryotic cell, eukaryotic cell, yeast cell, mammalian cell and *E. coli* cell; and further, the host cell is preferably selected from the group consisting of a CHO cell, NS0 cell, Sp2/0 cell and BHK cell.

The present disclosure also provides a method for producing the antibody or antigen-binding fragment thereof described in any one of the above, the method including culturing the above-described host cell under a condition allowing the expression of the above-described nucleic acid construct, and recovering the produced expressed protein from the culture.

The present disclosure also provides an antibody-drug conjugate targeting c-Met, which is a conjugate of any one of the above-mentioned antibody or antigen-binding fragment thereof and one or more therapeutic agents.

In some embodiments, the therapeutic agent is selected from the group consisting of a cytotoxic molecule, immunoenhancer and radioisotope, the cytotoxic molecule includes but is not limited to a tubulin inhibitor or DNA damaging agent; further preferably, the tubulin inhibitor includes but is not limited to a cytotoxic molecule of dolastatins and auristatins and a cytotoxic molecule of maytansines; the DNA damaging agent includes but is not limited to calicheamicins, duocarmycins, pyrrolobenzodiazepine derivatives (PBD), camptothecins and derivatives thereof, SN-38 and Dxd; more preferably, the cytotoxic molecule of auristatins includes but is not limited to MMAE, MMAF, and a derivative thereof, and the cytotoxic molecule of maytansines includes but is not limited to DM1, DM4, and a derivative thereof.

The preferred general structural formula of the antibody-drug conjugate provided by the present disclosure is A-(L-U)n, and: A represents the antibody or antigen-binding fragment thereof described in any one of the above; U is an active drug unit; L is any linking group, and is covalently linked to the antibody or antigen-binding fragment A and the active drug unit U, respectively; n is an integer selected from 1, 2, 3, 4, 5, 6, 7 and 8; and A is linked to 1, 2, 3, 4, 5, 6, 7 or 8 of the active drug unit U through one or more of the linking group L.

The linking group L is covalently linked to the amino residue or thiol residue on the antibody targeting c-Met or antigen-binding fragment A; preferably, the linking group L is covalently linked to the thiol residue on the antibody targeting c-Met or antigen-binding fragment A; more preferably, the linking group L is covalently linked to the thiol residue formed after the interchain disulfide bond on the antibody targeting c-Met or antigen-binding fragment A is opened. The linking group L includes a cleavable linker and a non-cleavable linker. The cleavable linker includes a peptide unit including 2-20 amino acids, and preferably, the peptide unit is selected from the group consisting of -valine-citrulline- (-Val-Cit-), -glycine-glycine-phenylalanine-glycine- (-Gly-Gly-Phe-Gly-), -valine-alanine- (-Val-Ala-), -valine-lysine- (-Val-Lys-), -valine-arginine- (-Val-Arg-), -phenylalanine-citrulline- (-Phe-Cit-), -phenylalanine-lysine- (-Phe-Lys-), -phenylalanine-arginine- (-Phe-Arg-) and a combination thereof.

In some embodiments, L includes a structure selected from the group consisting of:

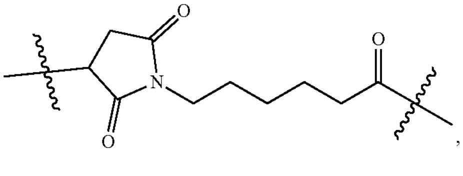
,
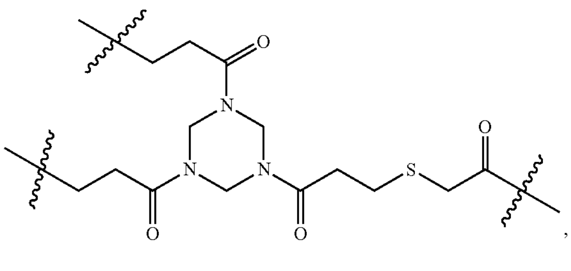
,

-continued
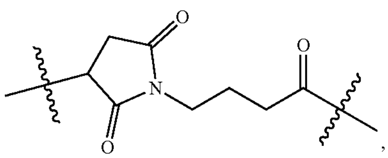
,
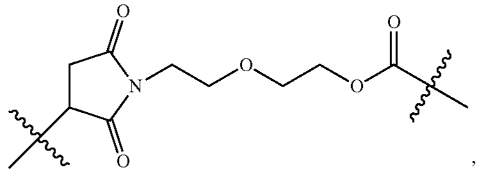
,
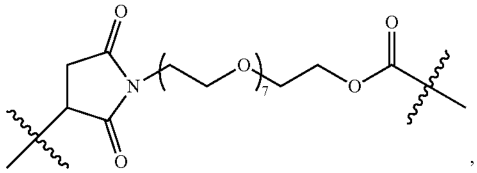
,
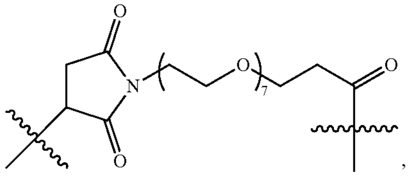
,
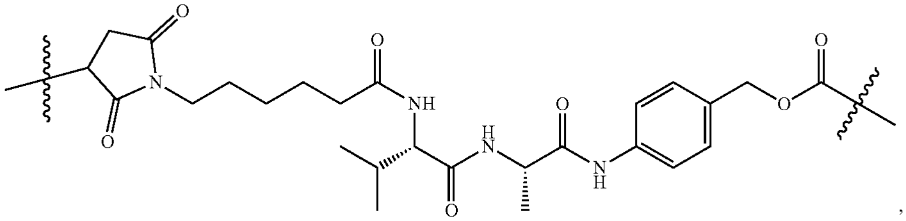
,
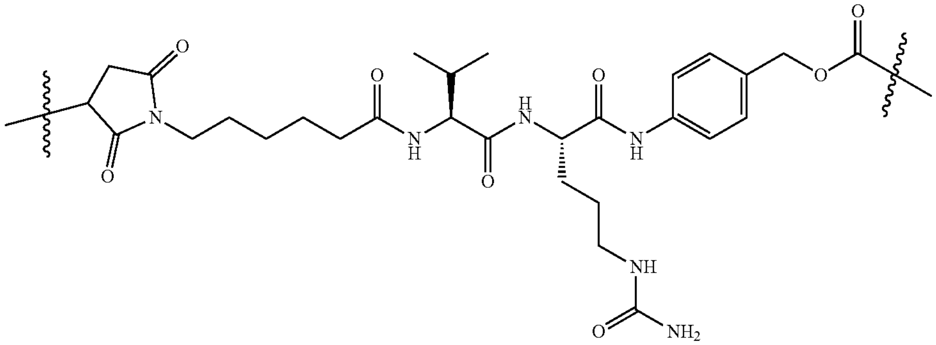
,
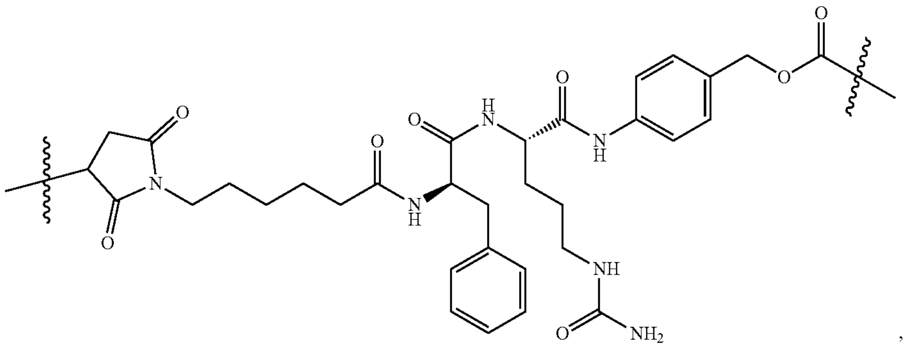
,
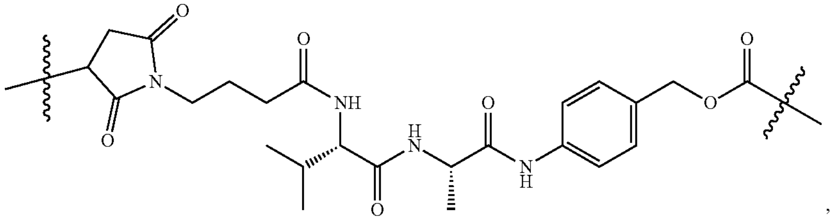
, -continued
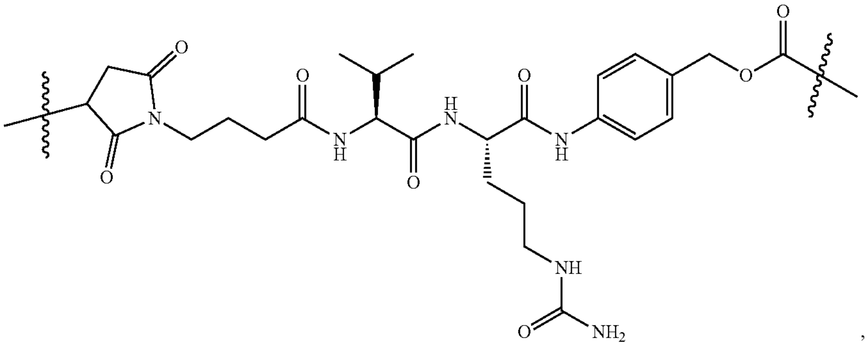
,
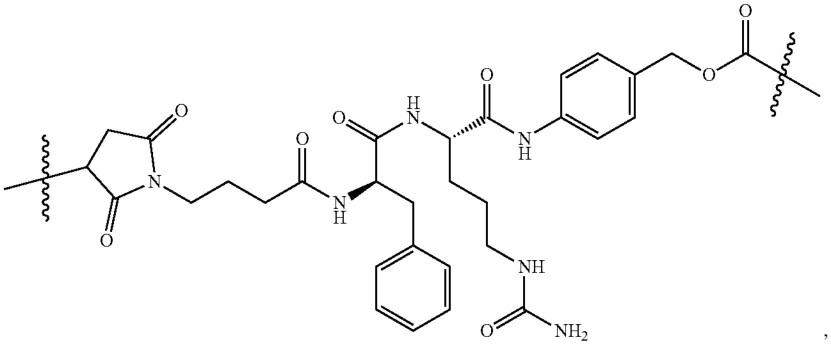
,
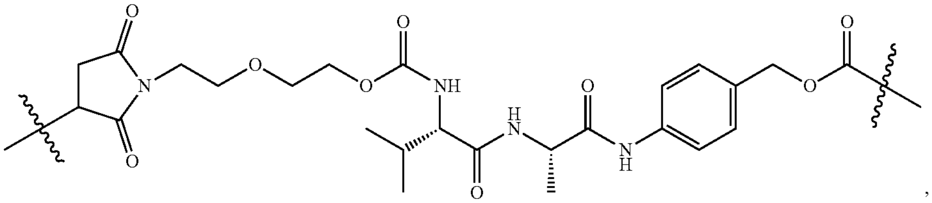
,
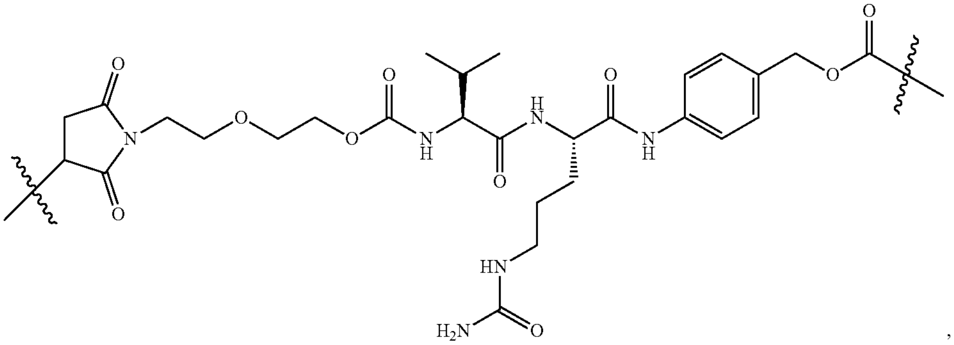
,
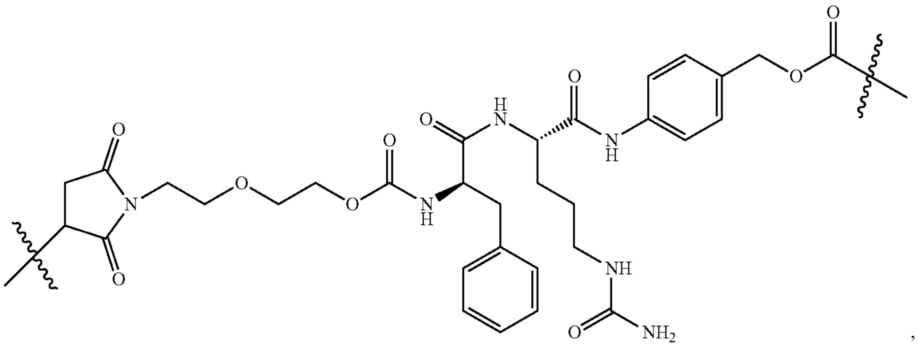
, -continued
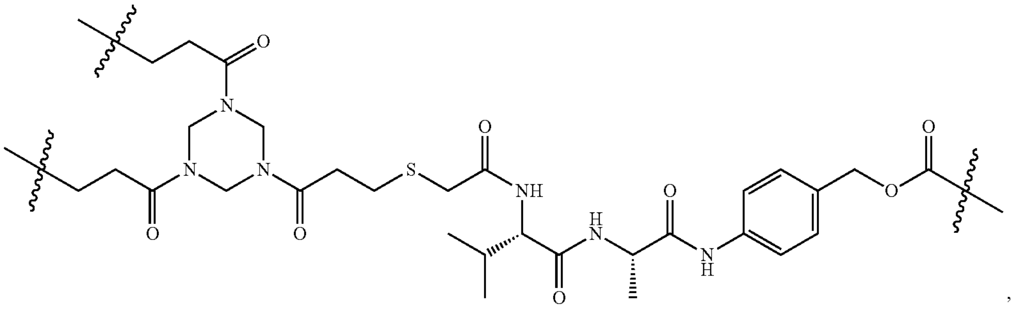
,
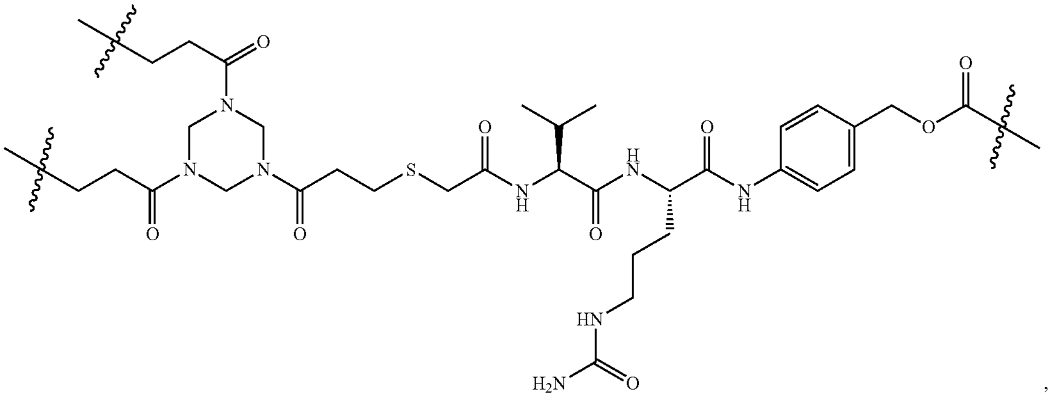
,
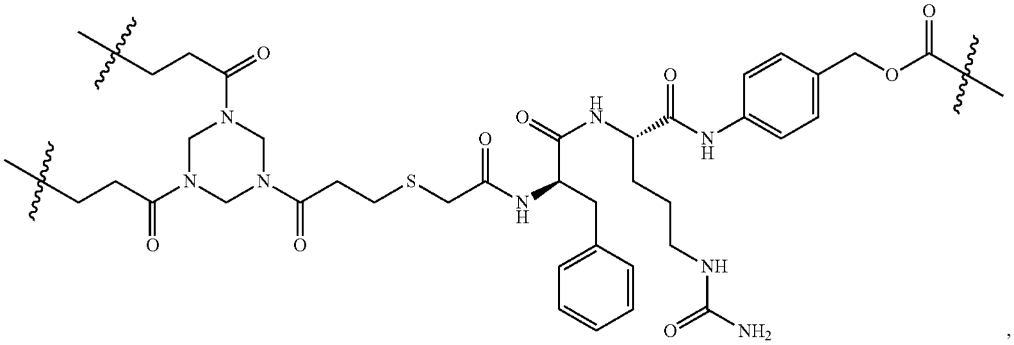
,
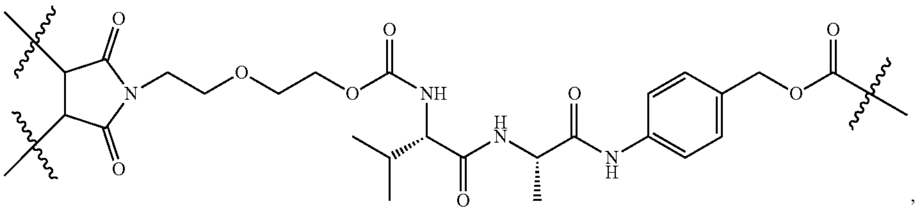
,
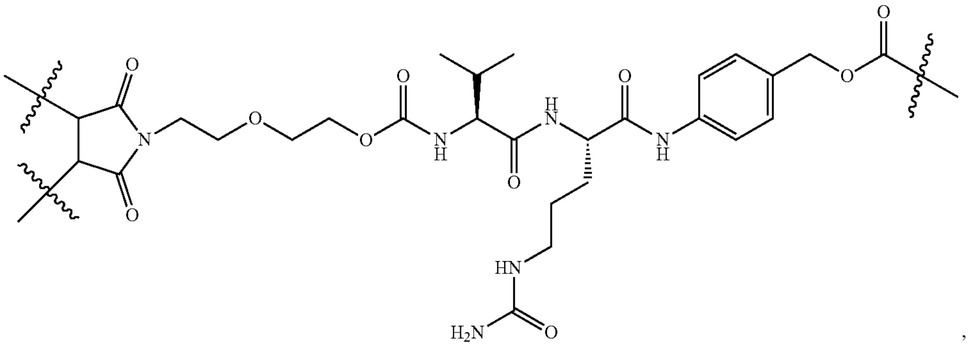
, -continued
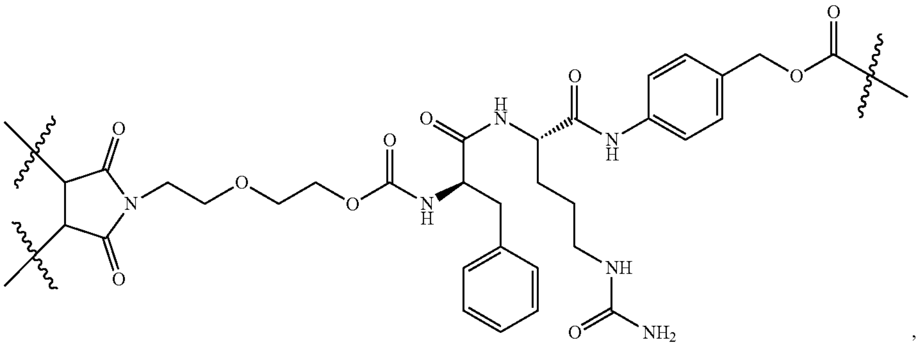
,
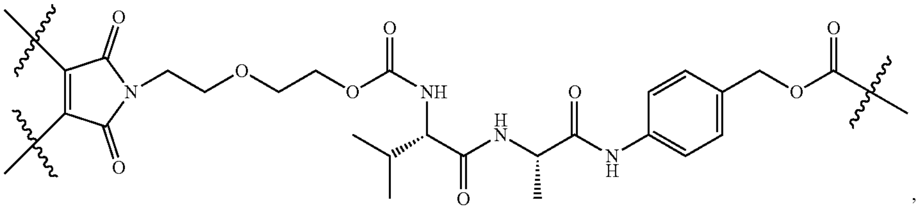
,
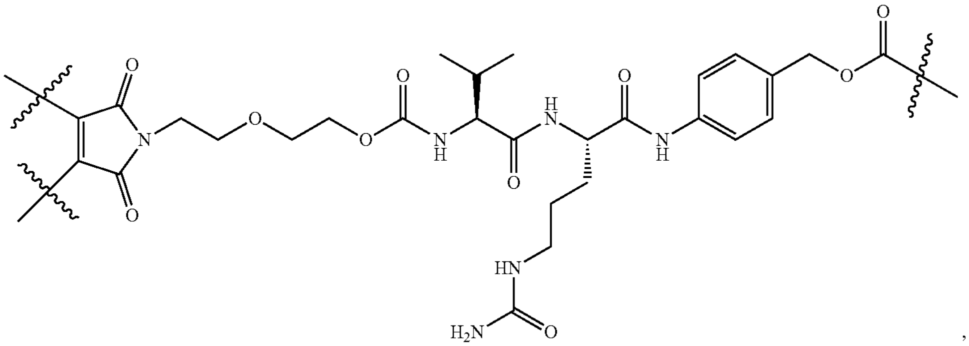
,
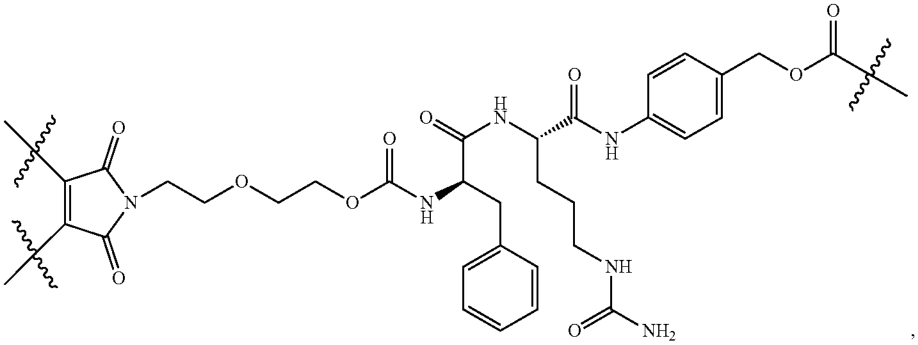
,
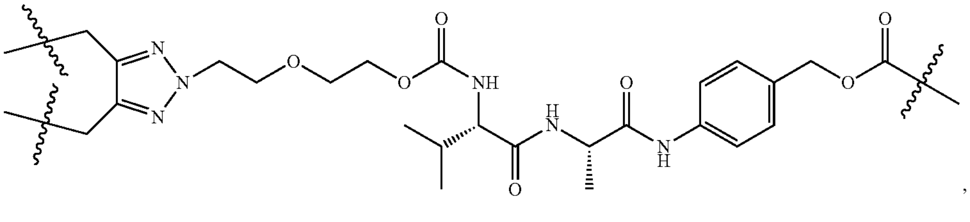
, -continued
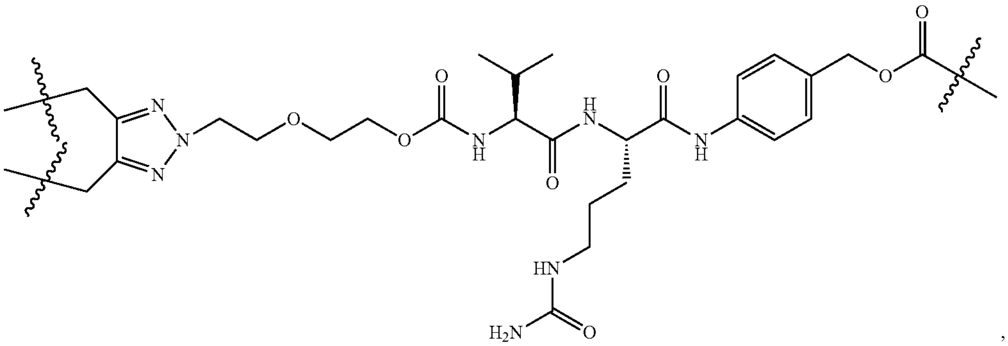
,
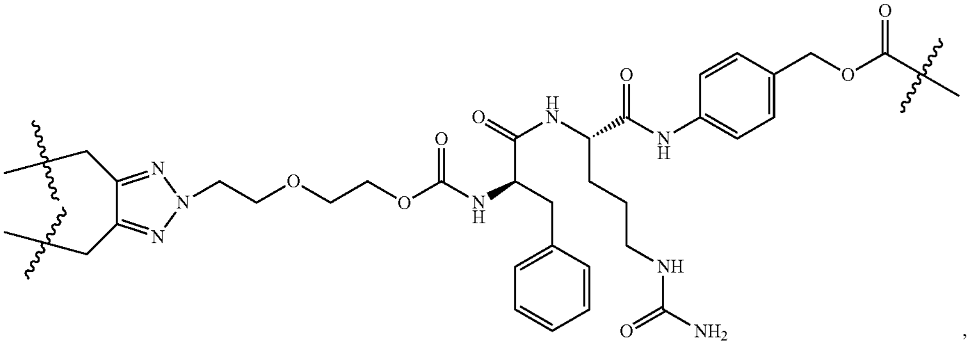
,
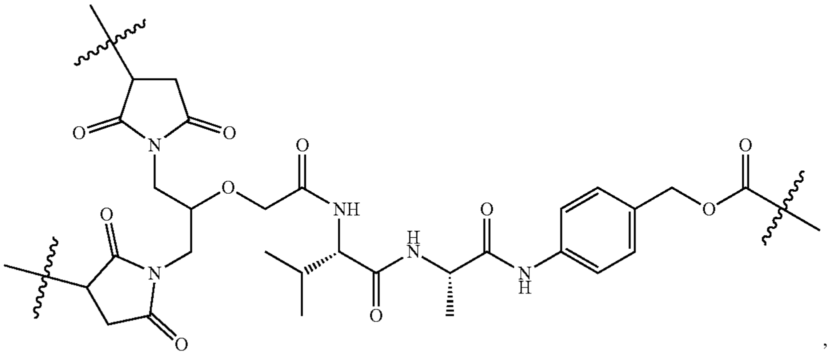
,
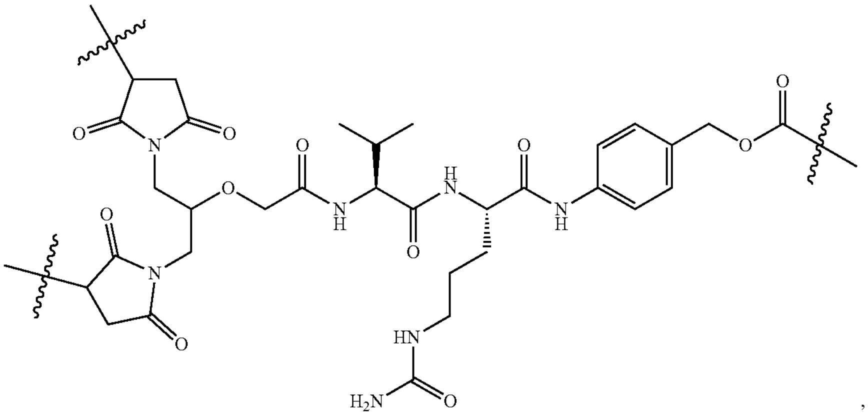
, -continued
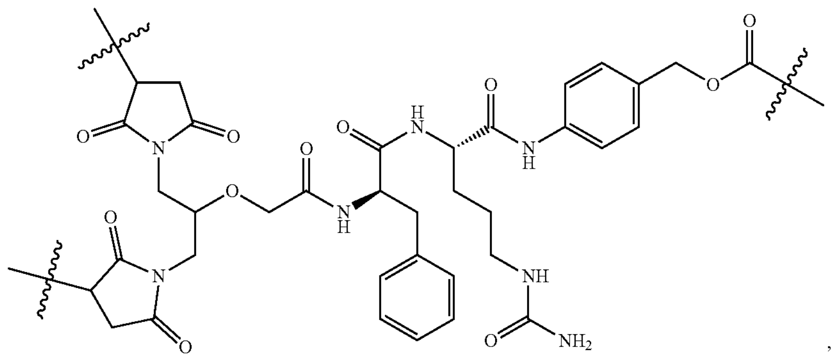
,
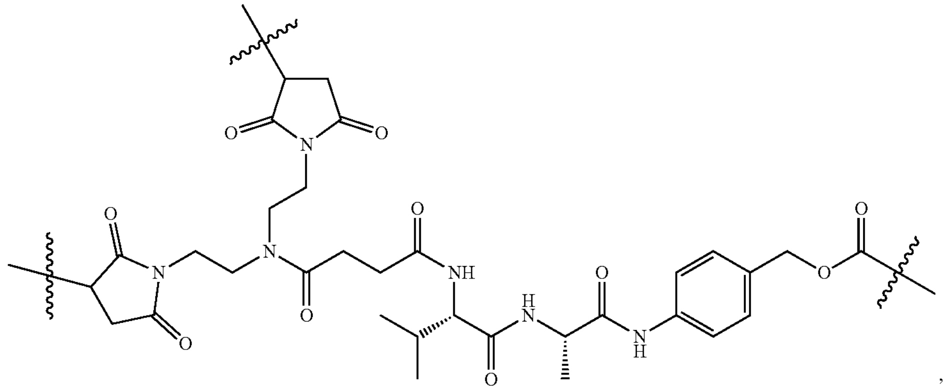
,
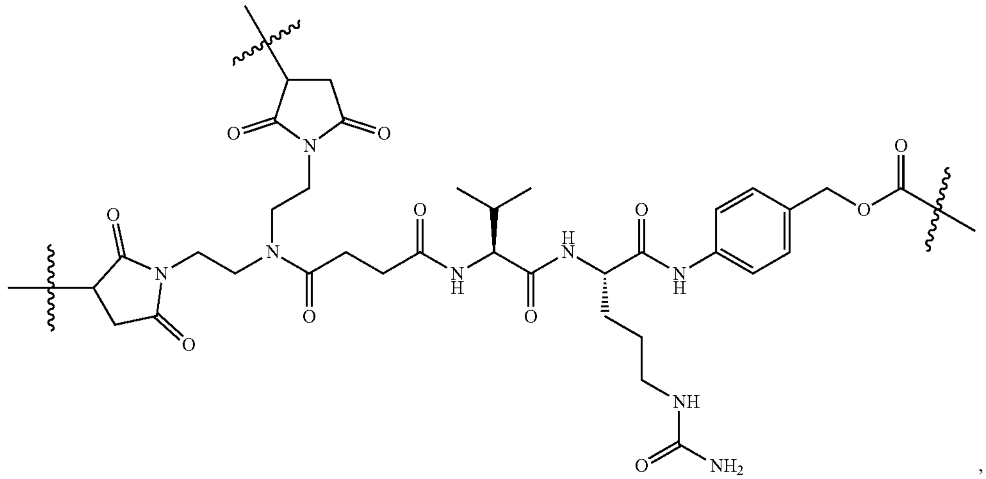
,
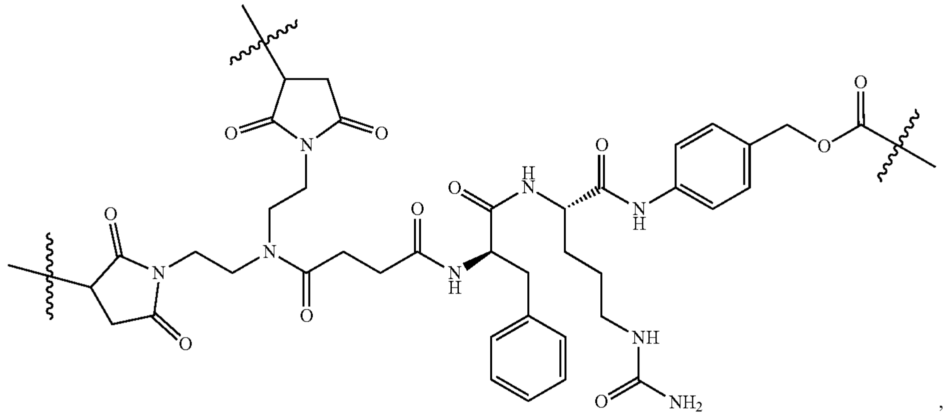
, -continued
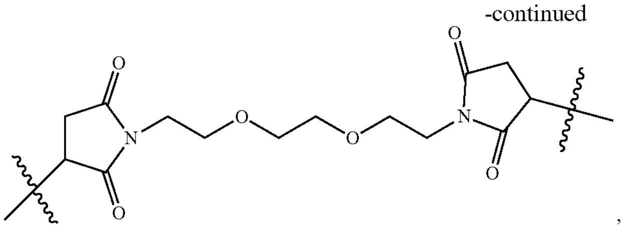
,
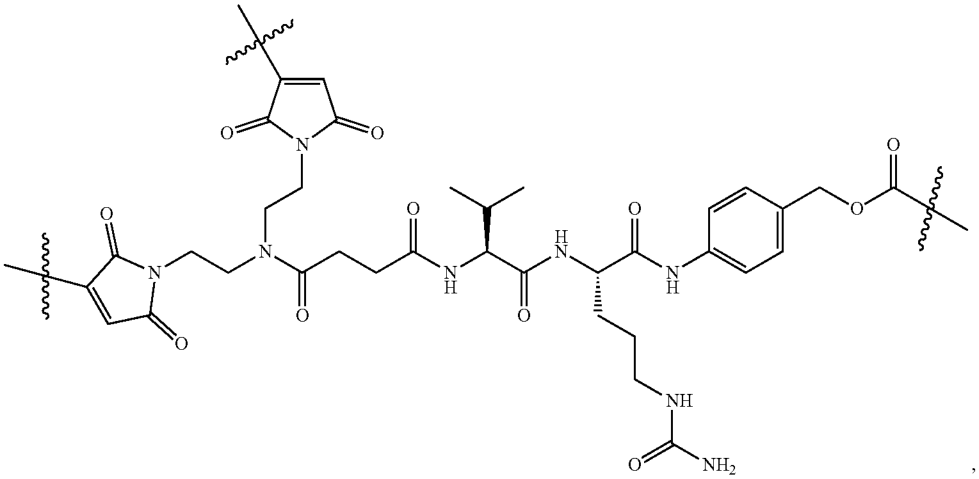
,
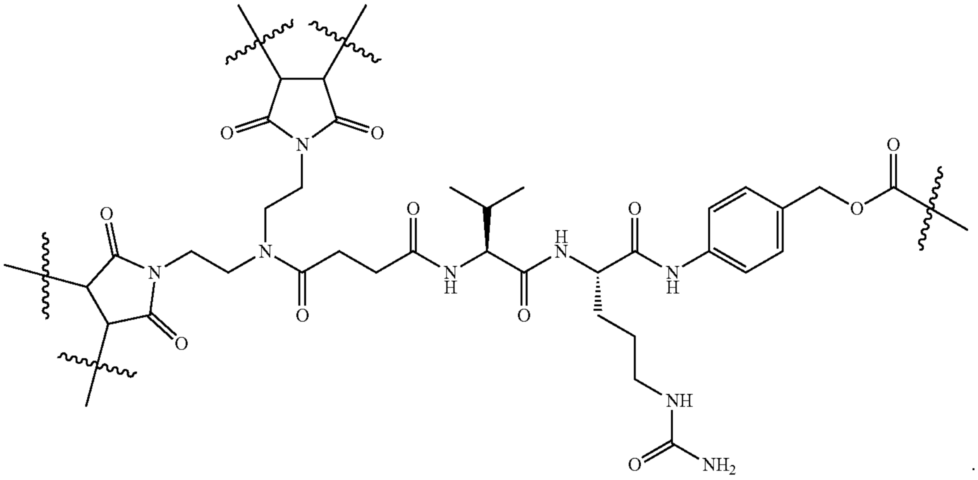
.
In some embodiments, the active drug unit U has a structure selected from the group consisting of:
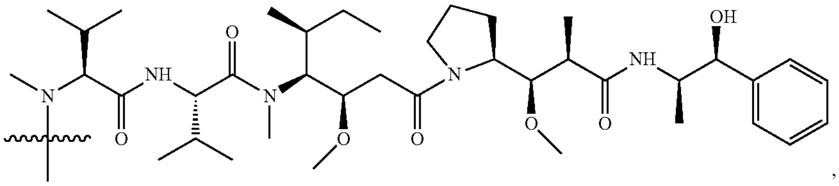
,
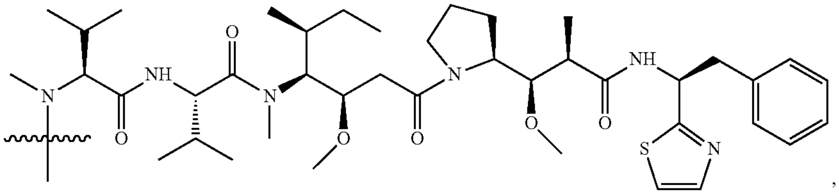
, -continued
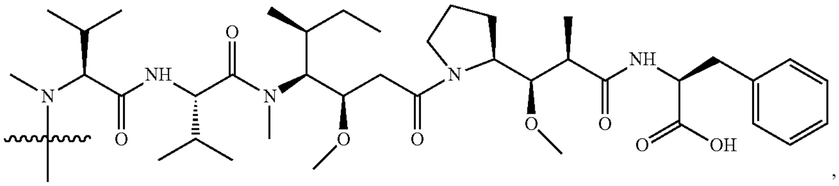
,
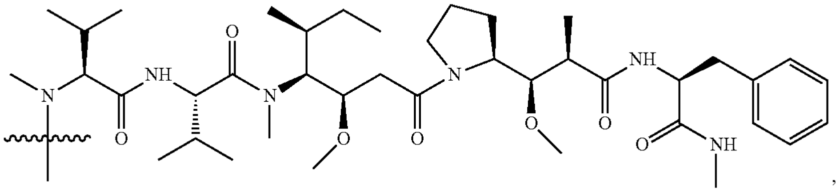
,
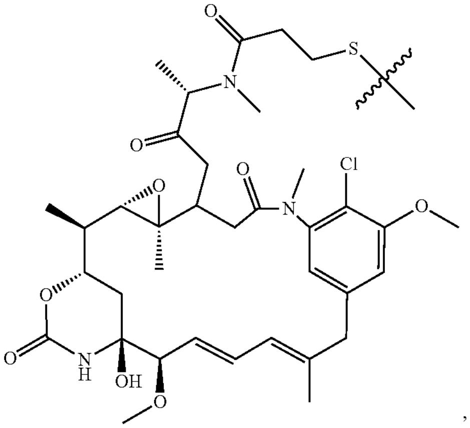
,
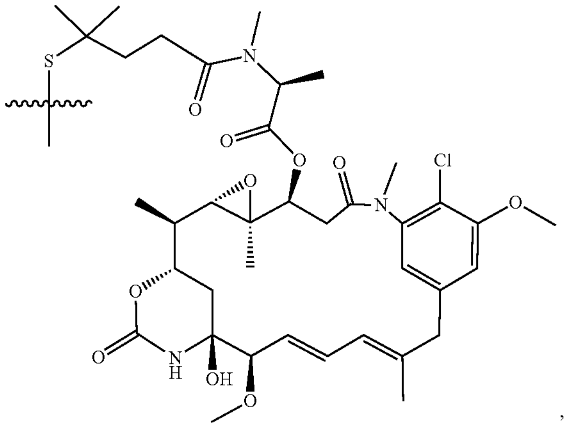
,
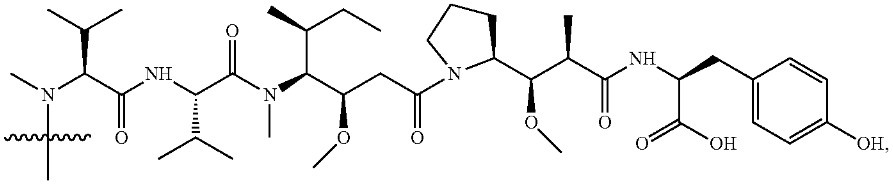
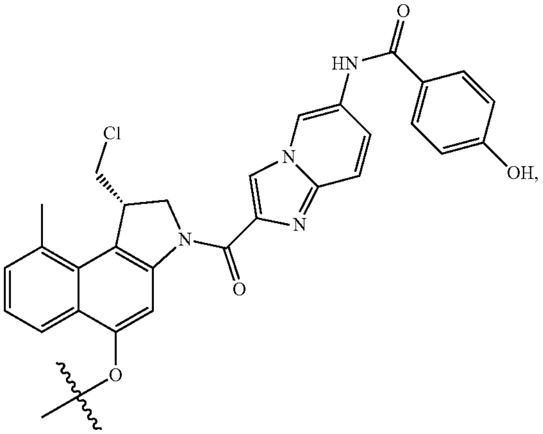
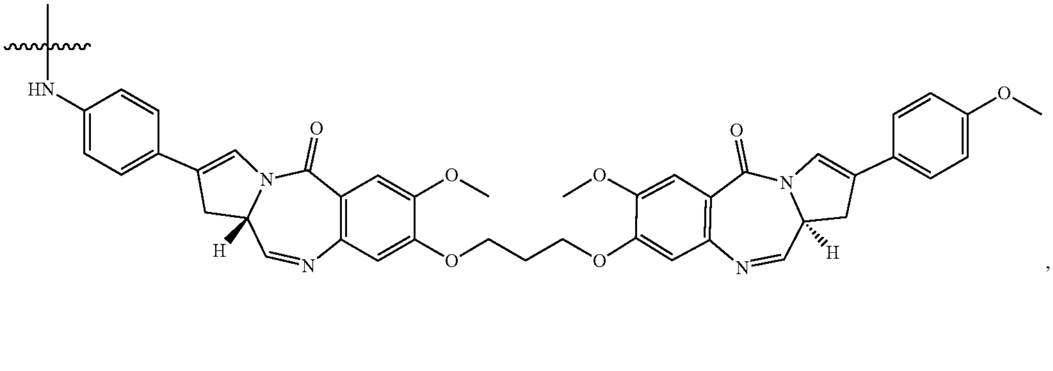
, -continued
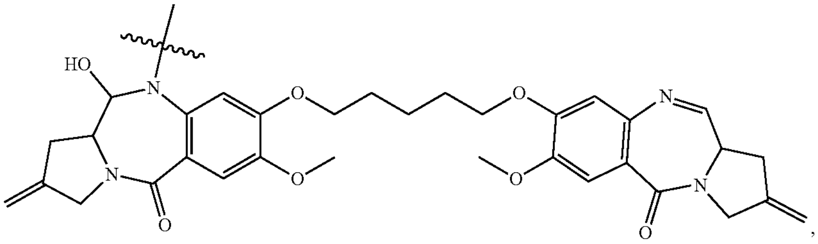
,
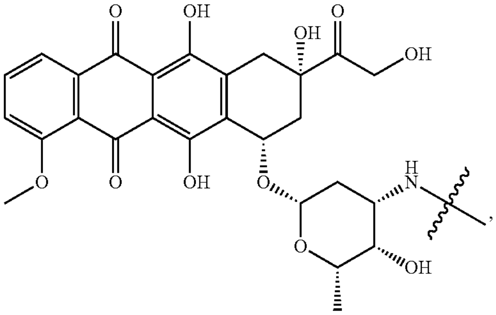
,
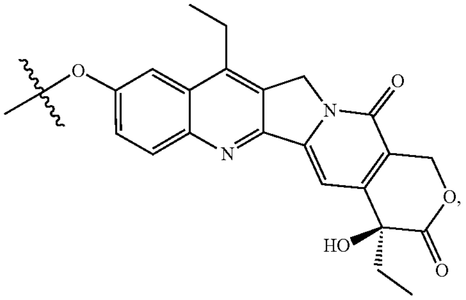
,
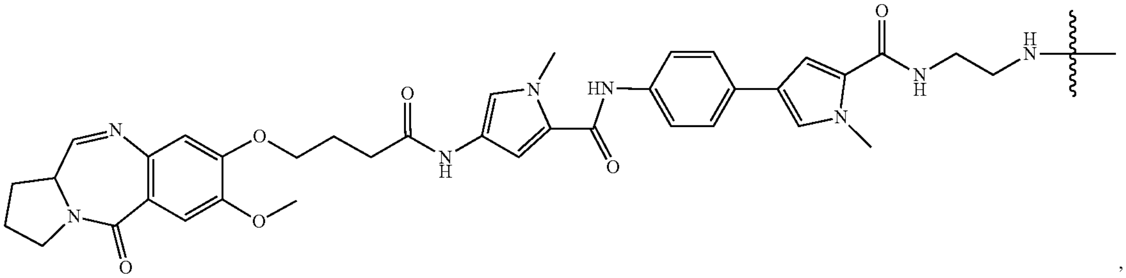
,
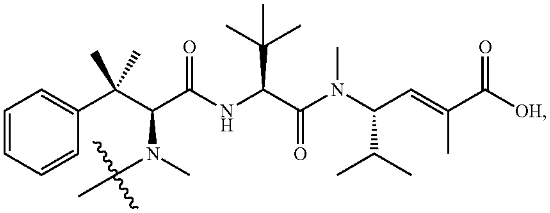
,
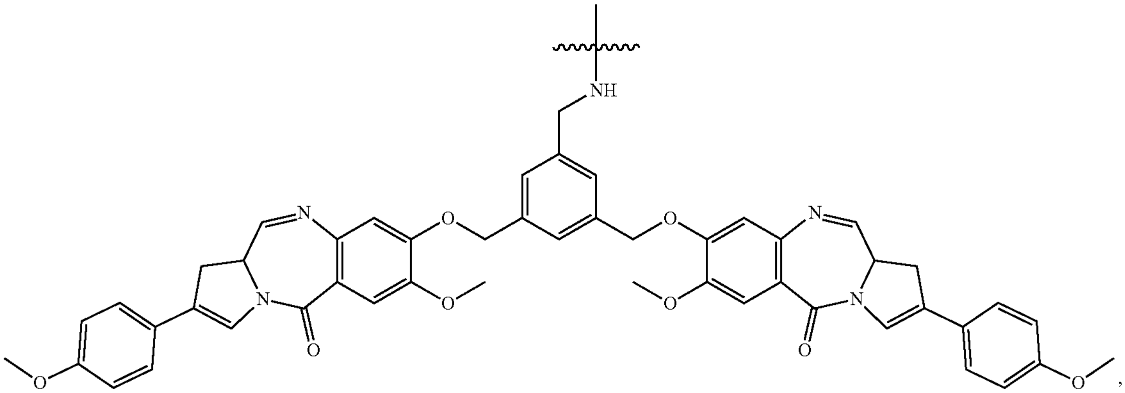
, -continued
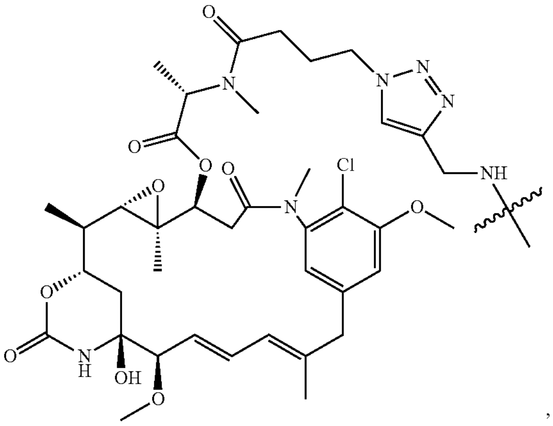
,
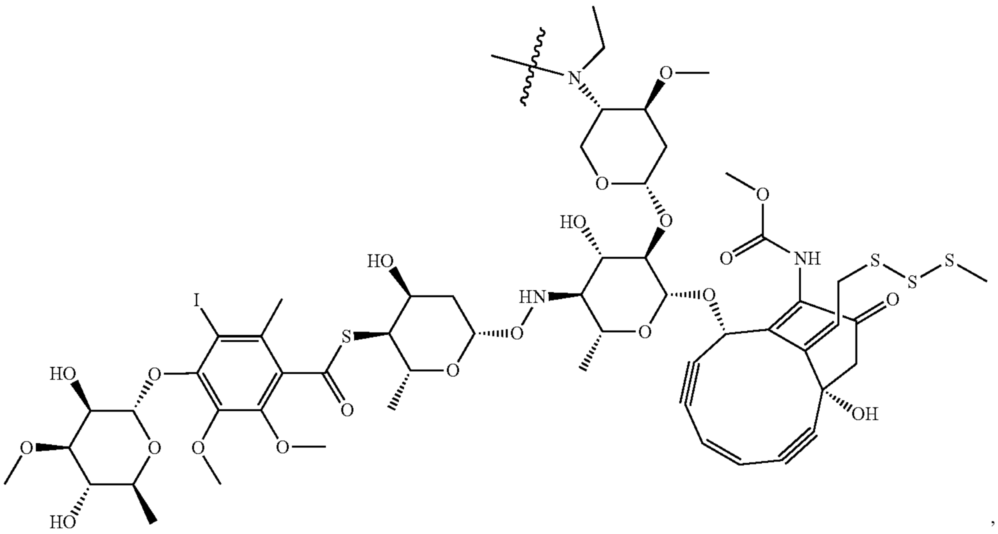
,
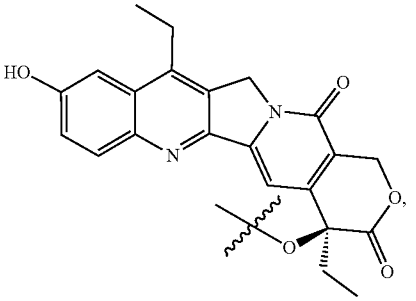
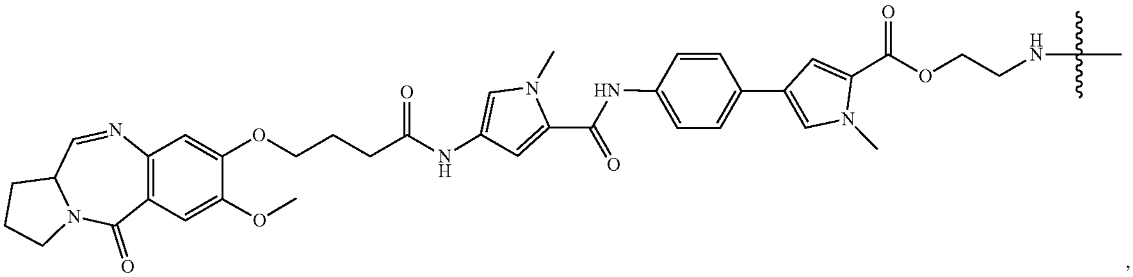
, -continued
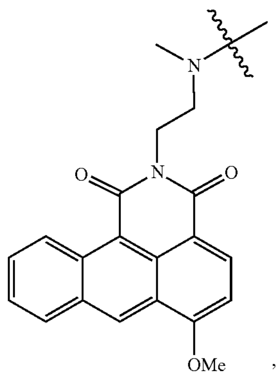
,
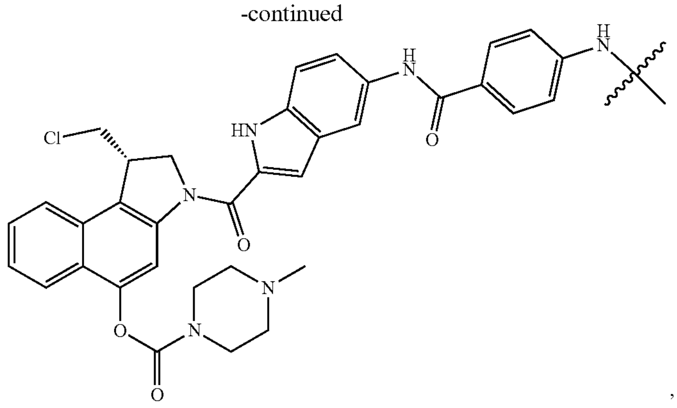
,
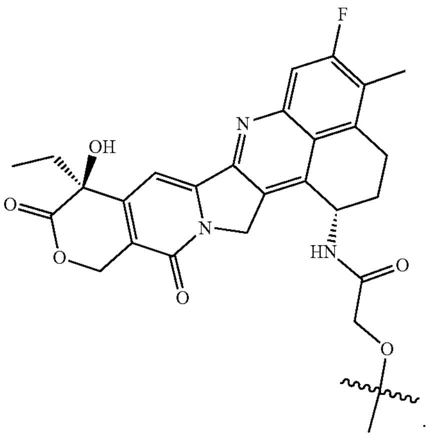
.
In some embodiments, the antibody-drug conjugate has a structure selected from the group consisting of:
ADC-1
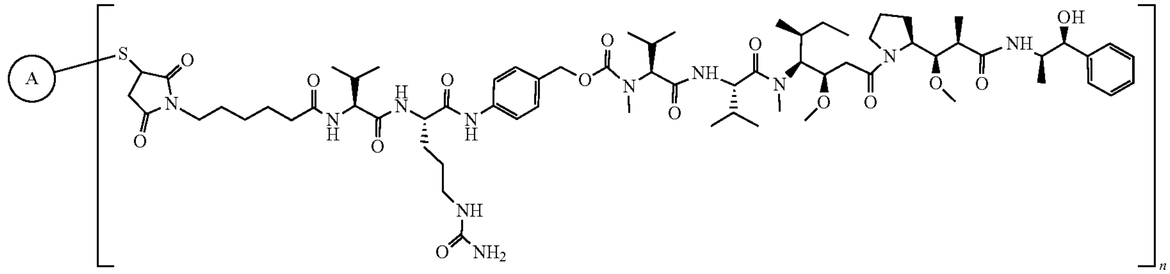

wherein, n in ADC-1 is an integer selected from 1, 2, 3, 4, 5, 6, 7 and 8; or
ADC-2
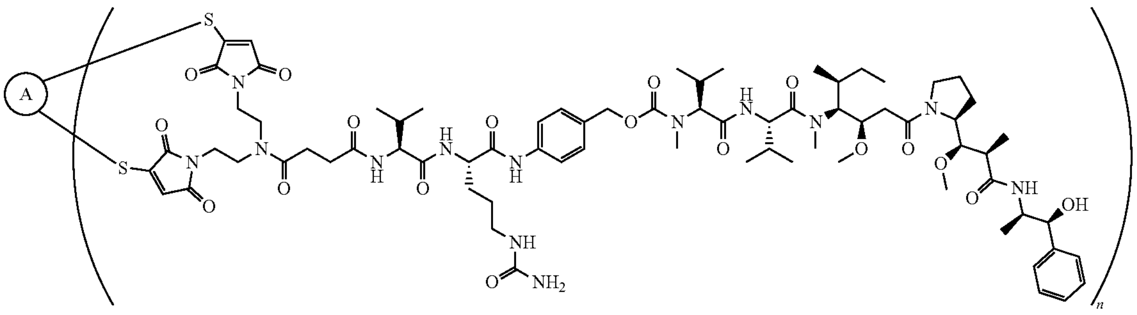
wherein, n in ADC-2 is an integer selected from 1, 2, 3 and 4; or
ADC-3
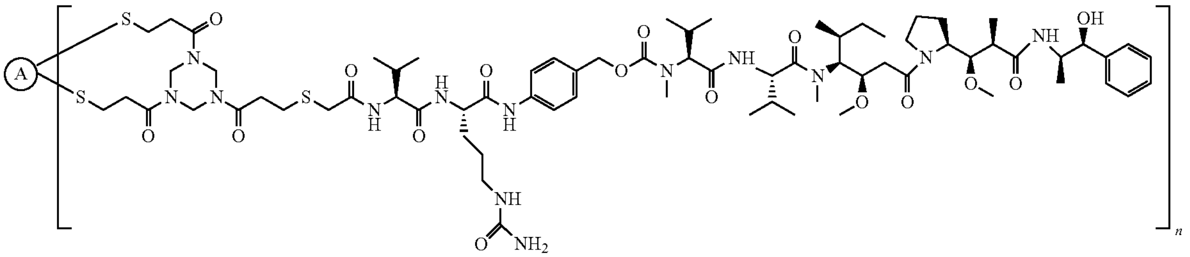
wherein, n in ADC-3 is an integer selected from 1, 2, 3 and 4; or
ADC-4
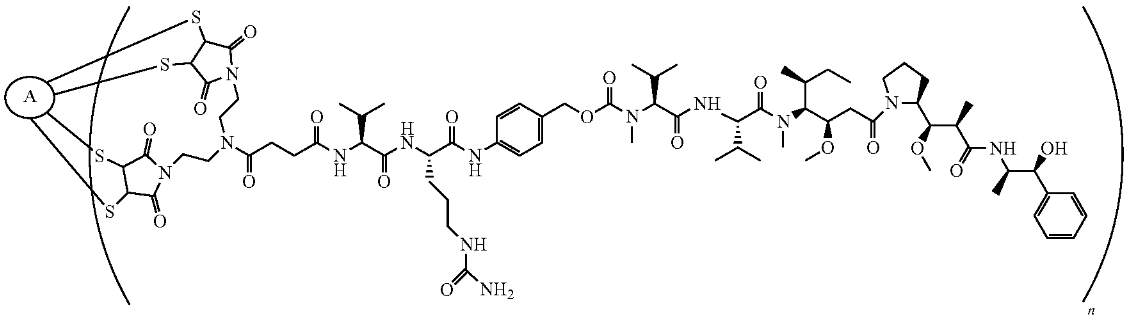

wherein, n in ADC-4 is an integer selected from 1 and 2; or
ADC-5
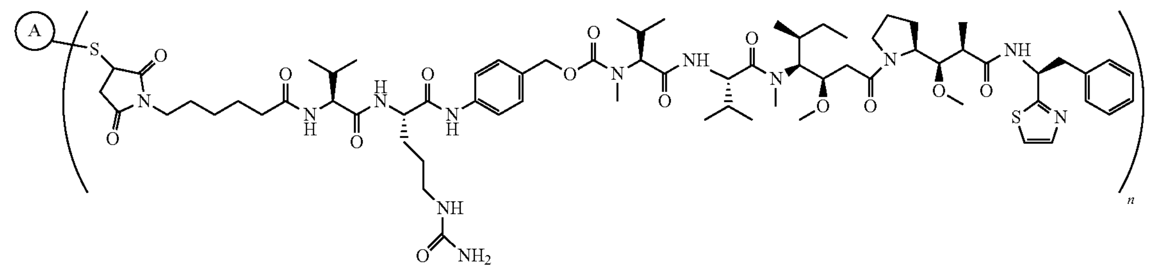
wherein, n in ADC-5 is an integer selected from 1, 2, 3, 4, 5, 6, 7 and 8; or
ADC-6
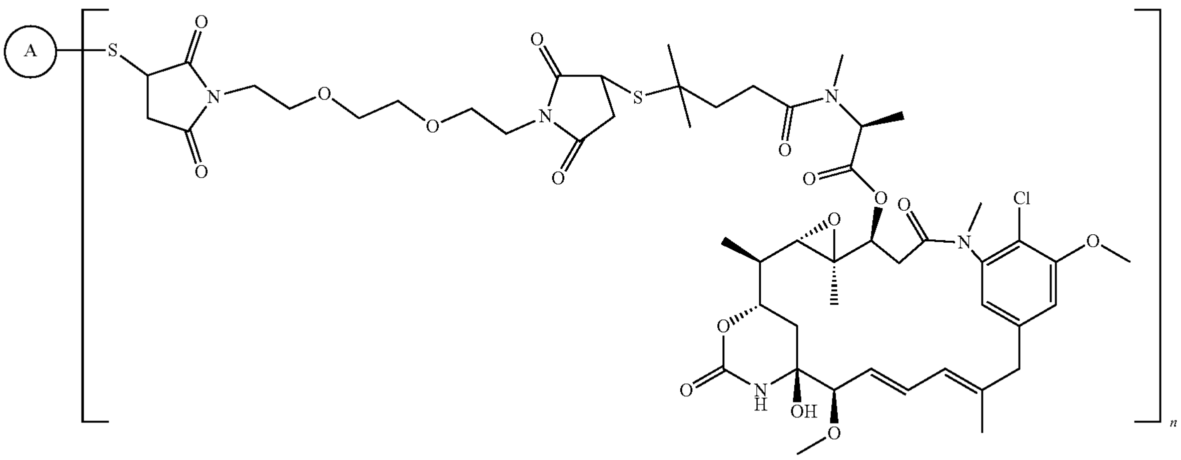
wherein, n in ADC-6 is an integer selected from 1, 2, 3, 4, 5, 6, 7 and 8; or
ADC-7
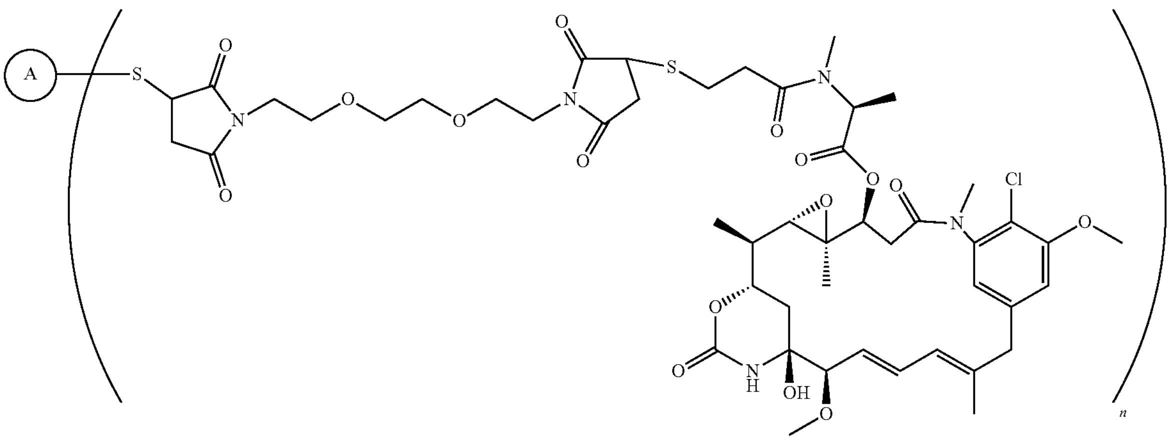
and, n in ADC-7 is an integer selected from 1, 2, 3, 4, 5, 6, 7 and 8.

The present disclosure also provides a pharmaceutical composition including the antibody or antigen-binding fragment thereof and/or antibody-drug conjugate described in any one of the above, and a pharmaceutically acceptable carrier.

The present disclosure also provides use of any one of the above-described antibody or antigen-binding fragment thereof, polynucleotide, nucleic acid construct, expression vector, antibody-drug conjugate or pharmaceutical composition in the manufacture of a medicament for treating or preventing a cancer.

In some embodiments, the cancer is a c-Met positive cancer.

In some embodiments, the c-Met positive cancer includes lung cancer and gastric cancer.

The present disclosure also provides a method of treating a disease, including administering to a patient in need thereof a therapeutically effective amount of the antibody-drug conjugate or pharmaceutical composition described in any one of the above; and the disease is a c-Met positive cancer, preferably lung cancer and gastric cancer.

The present disclosure also provides a kit including a container, a preparation placed in the container and an instruction; and the preparation comprises the antibody, antibody-drug conjugate or a pharmaceutically acceptable salt or solvate thereof, or the pharmaceutical composition described in any one of the above.

The present disclosure also provides use of the antibody or antigen-binding fragment thereof, antibody-drug conjugate, polynucleotide, nucleic acid construct, expression vector, or pharmaceutical composition described in any of the above in the manufacture of a medicament for treating or preventing a cancer. In one embodiment, the cancer is a solid tumor; and the solid tumor further includes lung cancer and gastric cancer.

The present disclosure also provides a recombinant protein including the antibody or antigen-binding fragment described in any one of the above.

The above-mentioned recombinant protein is preferably a bispecific antibody or multispecific antibody, and the multispecific antibody is preferably trispecific antibody, tetraspecific antibody, pentaspecific antibody, etc.

The present disclosure also provides use of any one of the above-mentioned antibody or antigen-binding fragment in the preparation of a recombinant protein.

DETAILED DESCRIPTION

Definitions

Figure 1:
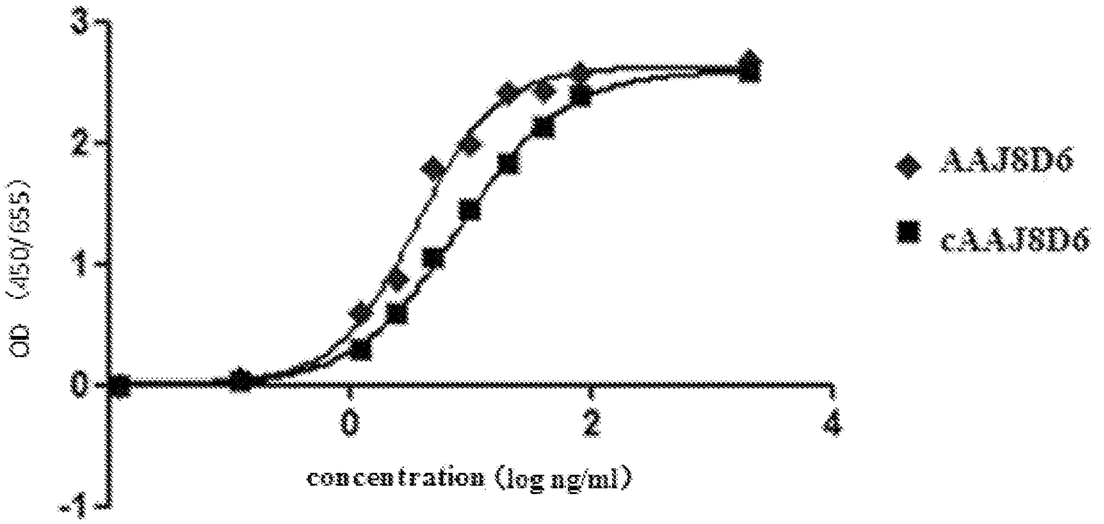
FIG. 1 shows the comparison of affinities of humanized antibody AAJ8D6 and chimeric antibody cAAJ8D8.

Unless otherwise defined, all technical and scientific terms used herein have the same meaning as understood by those of ordinary skill in the art. For definitions and terms in the art, those skilled in the art can specifically refer to Current Protocols in Molecular Biology (Ausubel). The abbreviations for amino acid residues are the standard 3-letter and/or 1-letter codes used in the art to refer to one of the 20 commonly used L-amino acids.

Definitions

Although the numerical ranges and parameter approximations are shown in the broad scope of the present disclosure, the numerical values shown in the specific examples are recorded as accurately as possible. However, any numerical value must inherently include an error, which is caused by the standard deviation in their respective measurements. In addition, all ranges disclosed herein should be understood as covering any and all subranges therein. For example, a recorded range of "1 to 10" should be considered to include any and all sub-ranges between a minimum of 1 and a maximum of 10 (inclusive); that is, all sub-ranges beginning with a minimum of 1 or greater, such as 1 to 6.1, and sub-ranges ending with a maximum of 10 or less, such as 5.5 to 10. In addition, any reference referred to as "incorporated herein" should be understood as being incorporated in its entirety.

It should also be noted that, as used in this specification, the singular form includes the plural form of the object to which it refers, unless clearly and explicitly limited to one object to which it refers. The term "or" may be used interchangeably with the term "and/or" unless the context clearly indicates otherwise.

As used herein, the terms "pharmaceutical composition", "combined drug", or "pharmaceutical combination" are used interchangeably, and means a combination of at least one drug and may have a pharmaceutically acceptable carrier or adjuvant material combined together to achieve a particular purpose. In one embodiment, the pharmaceutical composition comprises a combination that is separated in time and/or space as long as it can work together to achieve embodiments of the present disclosure. For example, the components contained in the pharmaceutical composition (for example, the antibody, nucleic acid molecule, nucleic acid molecule combination, and/or antibody-drug conjugate according to the present disclosure) may be administered to a subject as a whole or separately. When the ingredients contained in the pharmaceutical composition are separately administered to a subject, the ingredients can be administered to the subject simultaneously or sequentially. In one embodiment, the pharmaceutically acceptable carrier is water, a buffered aqueous solution, an isotonic saline solution such as PBS (phosphate buffer), glucose, mannitol, dextrose, lactose, starch, magnesium stearate, cellulose, magnesium carbonate, 0.3% glycerol, hyaluronic acid, ethanol or polyalkylene glycol such as polypropylene glycol, triglyceride and the like. The type of the pharmaceutically acceptable carrier used depends, inter alia, on whether the composition according to the present disclosure is formulated for oral, nasal, intradermal, subcutaneous, intramuscular or intravenous administration. The composition according to the present disclosure may contain a wetting agent, an emulsifier or a buffer substance as an additive.

The pharmaceutical composition, vaccine or pharmaceutical formulation according to the present disclosure can be administered by any suitable route, for example, orally, nasally, intradermally, subcutaneously, intramuscularly or intravenously.

The term "therapeutic agent" as used herein refers to any substance or entity plays a therapeutic role (e.g., treating, preventing, relieving or inhibiting any disease and/or condition), including but not limited to a chemotherapeutic agent, radiotherapy agent, immunotherapeutic agent, thermally therapeutic agent.

As used herein, "CDR region" or "CDR" refers to the hypervariable region of the heavy and light chain of an immunoglobulin, as defined by Kabat et al. (Kabat et al., Sequences of proteins of immunological interest, 5th Ed., U.S. Department of Health and Human Services, NIH, 1991, and later editions). There are three heavy chain CDRs and three light chain CDRs. Depending on the circumstances, the term CDR or CDRs used herein is used to indicate one of these regions, or several or even all of these regions, which region contains most of the amino acid residues responsible for binding based on the affinity of an antibody for an antigen or its recognition epitope.

For the present disclosure, "consistency", "identity" or "similarity" between two nucleic acid or amino acid sequences refers to the percentage of the same nucleotide or amino acid residues between the two sequences to be compared obtained after the optimal alignment. The percentage is purely statistical and the differences between the two sequences are randomly distributed and cover their full length. Comparisons between two nucleic acid or amino acid sequences are usually performed by comparing these sequences after aligning them in an optimal manner, and can be performed over a segment or over a "comparison window". In addition to manual implementation, the optimal alignment used for comparing sequences can also be performed by the local homology algorithm of Smith and Waterman (1981) [Ad. App. Math. 2:482], by the local homology algorithm of Neddleman and Wunsch (1970) [J. MoI. Biol. 48:443], by the similarity search method of Pearson and Lipman (1988) [Proc. Natl. Acad. Sci. USA 85:2444), or by a computer software using these algorithms (GAP, BESTFIT, FASTA and TFASTA in the Wisconsin Genetics Software Package, Genetics Computer Group, 575 Science Dr., Madison, WI, or by a comparison software BLAST N or BLAST P).

As used herein, "therapeutically effective amount" or "effective amount" refers to a dose sufficient to demonstrate a benefit when administered to a subject. The actual amount administered, as well as the frequency and time course of administration will depend on the condition and severity of the subject to be treated. General practitioners and other doctors are ultimately responsible for the treatment prescription (for example, decision on the dose) and usually make decisions based on the disease being treated, the condition of the individual patient, the delivery site, the mode of administration, and other factors known to the doctor.

The term "subject" as used herein refers to a mammal, such as human, but may also refer to other animals, such as wild animals (such as heron, stork, crane), domestic animals (such as duck, goose) or experimental animals (such as orangutan, monkey, rat, mouse, rabbit, guinea pig, marmot, ground squirrel).

The term "antibody" includes monoclonal antibody, bispecific antibody, multispecific antibody or recombinant protein including antigen-binding fragment; the term "antigen-binding fragment" includes Fab fragment, F(ab') fragment, F(ab')2 fragment, Fv fragment, dAb, Fd, single chain antibody (scFv), scFv-Fc fragment or diabody, or any fragment that should be able to increase half-life by chemical modification or by incorporation into liposomes, such chemical modifications as the addition of poly(alkylene) glycols such as polyethylene glycol ("PEGylation") (PEGylated fragments known as Fv-PEG, scFv-PEG, Fab-PEG, F(ab')2-PEG or Fab'-PEG) ("PEG" refers to polyethylene glycol), and such fragment has EGFR binding activity. In one embodiment, the functional fragment will consist of or comprise partial sequences of the heavy or light variable chain of the antibody from which it is derived, which partial sequence is sufficient to retain the same binding specificity and sufficient affinity as the antibody from which it is derived, preferably for EGFR at least equal to 1/100 of the affinity of the antibody from which it is derived, more preferably at least equal to 1/10. Such a functional fragment comprises a minimum of 5 amino acids, preferably 10, 15, 25, 50 and 100 contiguous amino acids of the antibody sequence from which it is derived.

The term "humanized antibody" refers to an antibody including a CDR region derived from a non-human antibody, and the other portion of the antibody is derived from one (or several) human antibody (antibodies). Moreover, in order to retain binding affinity, some residues of the backbone (referred to as FR) segment may be modified (Jones et al., Nature, 321:522-525, 1986; Verhoeyen et al., Science, 239: 1534-1536, 1988; Riechmann et al., Nature, 332: 323-327, 1988). A humanized antibody or fragment thereof according to the present disclosure can be prepared by known techniques;

The term "chimeric antibody" refers to an antibody in which the variable region sequence is derived from one species and the constant region sequence is derived from another species, for example, the variable region sequence is derived from a mouse antibody and the constant region sequence is derived from a human antibody. The chimeric antibody or fragment thereof according to the present disclosure can be prepared by using genetic recombination technology. For example, the chimeric antibody can be produced by cloning recombinant DNA including a promoter and a sequence encoding the variable region of the non-human and especially murine monoclonal antibody according to the present disclosure, and a sequence encoding the constant region of a human antibody. The chimeric antibody of the present disclosure encoded by this recombinant gene will be, for example, a murine-human chimera, and the specificity of the antibody is determined by the variable region derived from murine DNA, and its isotype is determined by the constant region derived from human DNA. Method for preparing chimeric antibodies can be found in, for example, Verhoeyn et al. (BioEssays, 8:74, 1988).

The term "monoclonal antibody" refers to a preparation of antibody molecules having a single molecular composition.

The monoclonal antibody composition shows a single binding specificity and affinity for a specific epitope.

The term "AAJ8D6 antibody" used herein, unless otherwise specified, refers to the humanized monoclonal antibody AAJ8D6 targeting c-Met obtained by the present disclosure.

The cAAJ8D6 antibody used herein refers to a human-murine chimeric antibody including a murine variable region and a human constant region. The difference between the cAAJ8D6 antibody and the AAJ8D6 antibody is only in the framework region in the variable region that the framework region of cAAJ8D6 is of murine origin, and the framework region of AAJ8D6 is of human origin.

In general, in order to prepare a monoclonal antibody or functional fragment thereof, especially of murine origin, reference may be made to the techniques described in particular in the manual "Antibodies" (Harlow and Lane, Antibodies: A Laboratory Manual, Cold Spring Harbor Laboratory, Cold Spring Harbor NY, pp. 726, 1988) or to the techniques for preparation from hybridoma cells described by Kohler and Milstein (Nature, 256:495-497, 1975).

The monoclonal antibody according to the present disclosure can be purified, for example, on an affinity column on which c-Met antigen has been immobilized in advance or which comprises one of the fragments of the epitope that can be specifically recognized by the monoclonal antibody according to the present disclosure. More specifically, the monoclonal antibody can be purified by protein A and/or G chromatography, in the presence or absence of ion exchange chromatography aimed at eliminating residual protein contaminants as well as DNA and LPS with or without size exclusion chromatography on Sepharose gels aimed at eliminating potential aggregates due to the presence of dimers or other multimers. More preferable, all of these techniques can be used simultaneously or sequentially.

The term "dolastatin" as used herein refers to a polypeptide isolated from a marine organism, *Dollabella auricularia*, which includes, but is not limited to, dolastatin 10 and dolastatin 15. Dolastatin is a mitotic inhibitor that exhibits strong anticancer activity, and is therefore a candidate for anticancer drugs. The researchers further discovered and synthesized many derivatives of dolastatin, such as MMAE and MMAF.

The term "linker" or "linking group" as used herein refers to the moiety of an antibody-drug conjugate (i.e. ADC) that links an antibody to a drug, which may or may not be cleavable. Cleavable linkers (i.e., breakable linkers or biodegradable linkers) can be cleaved in or on target cells to release the drug. In one embodiment, the linker of the present disclosure has very good stability, greatly reducing the release of the drug before delivery to the target (e.g., in the blood), to reduce side effects and toxicity. In some specific embodiments, the linker of the present disclosure is selected from cleavable linkers, such as disulfide-based linkers (which are selectively cleaved in tumor cells with higher thiol concentrations), peptide linkers (which are cleaved by enzymes in tumor cells) and hydrazone linker. In other specific embodiments, the linker of the present disclosure is selected from non-cleavable linkers, such as thioether linkers. In one embodiment, the linker of the present disclosure is selected from the group consisting of cleavable mc-vc-PAB linker and non-cleavable mc linker.

[Specific Examples]

Example 1. Preparation of Humanized c-Met Antibody and Determination of Amino Acid Sequence Thereof Based on the c-Met murine antibody mAAJ8D6, a variety of chimeric antibodies and humanized antibodies were further designed and compared for affinity, and the candidate chimeric c-Met antibody cAAJ8D6 and humanized anti-antibody AAJ8D6 were finally determined.

TABLE 2

CDRs 1-3 of heavy chain variable region and light chain variable region of AAJ8D6 (Kabat method)

| | | | |
|---|---|---|---|
| Heavy chain | HCDR1 | SEQ ID NO: 1 | SYWMH |
| | HCDR2 | SEQ ID NO: 2 | MIDPSDSESRLNQKFKD |
| | HCDR3 | SEQ ID NO: 3 | SGYHGTSYWYFDV |
| Light chain | LCDR1 | SEQ ID NO: 4 | RSSKSLLHSDGITYLY |
| | LCDR2 | SEQ ID NO: 5 | QMSNLAS |
| | LCDR3 | SEQ ID NO: 6 | AQNLELPPT |

Amino acid sequence of the heavy chain variable region of anti-c-Met humanized antibody AAJ8D6 (SEQ ID NO: 7):

```
QVQLEQSGPE VVKPGASVKV SCKASGYSFT        60
SYWMHWVRQA PGQGLEWMGM IDPSDSESRL

NQKFKDRVTM TVDTPTSTVY MELSSPRSED       120
TAVYYCARSG YHGTSYWYFD VWGQGTLVTV

SS                                     122
```

Amino acid sequence of the light chain variable region of anti-c-Met humanized antibody AAJ8D6 (SEQ ID NO: 8):

```
DIVMTQSPLS LPVTPGEPAS ISCRSSKSLL        60
HSDGITYLYW YLQKPGQSPQ LLIYQMSNLA

SGVPDRFSGS GSGTDFTLKI SRVEAEDVGV       115
YYCAQNLELP PTFGGGTKVE IKRTV
```

Amino acid sequence of the heavy chain of anti-c-Met humanized antibody AAJ8D6 (SEQ ID NO: 9):

```
QVQLEQSGPE VVKPGASVKV SCKASGYSFT        60
SYWMHWVRQA PGQGLEWMGM IDPSDSESRL

NQKFKDRVTM TVDTPTSTVY MELSSPRSED       120
TAVYYCARSG YHGTSYWYFD VWGQGTLVTV

SSASTKGPSV FPLAPSSKST SGGTAALGCL       180
VKDYFPEPVT VSWNSGALTS GVHTFPAVLQ

SSGLYSLSSV VTVPSSSLGT QTYICNVNHK       240
PSNTKVDKKV EPKSCDKTHT CPPCPAPELL

GGPSVFLFPP KPKDTLMISR TPEVTCVVVD       300
VSHEDPEVKF NWYVDGVEVH NAKTKPREEQ

YNSTYRVVSV LTVLHQDWLN GKEYKCKVSN       360
KALPAPIEKT ISKAKGQPRE PQVYTLPPSR

EEMTKNQVSL TCLVKGFYPS DIAVEWESNG       420
QPENNYKTTP PVLDSDGSFF LYSKLTVDKS

RWQQGNVFSC SVMHEALHNH YTQKSLSLSP       452
GK
```

Amino acid sequence of the light chain of anti-c-Met humanized antibody AAJ8D6 (SEQ ID NO: 10):

```
DIVMTQSPLS LPVTPGEPAS ISCRSSKSLL        60
HSDGITYLYW YLQKPGQSPQ LLIYQMSNLA

SGVPDRFSGS GSGTDFTLKI SRVEAEDVGV       120
YYCAQNLELP PTFGGGTKVE IKRTVAAPSV

FIFPPSDEQL KSGTASVVCL LNNFYPREAK       180
VQWKVDNALQ SGNSQESVTE QDSKDSTYSL

SSTLTLSKAD YEKHKVYACE VTHQGLSSPV       219
TKSFNRGEC
```

Example 2 Affinity Comparison of Chimeric cAAJ8D6 and Humanized Antibody AAJ8D6

The affinities of chimeric cAAJ8D6 and the humanized antibody AAJ8D6 were determined by ELISA. A 96-well plate was coated with soluble ED protein and then incubated with diluted antibodies. ED-related antibodies were detected with an HRP-conjugated goat F(ab')2 anti-human IgG Fc-specific secondary antibody. The GraphPaD Prism software was used and X was changed to log X to fit a dose-response curve, which is shown in FIG. 1.

From the experimental results shown in FIG. 1, the comparison of AAJ8D6 with cAAJ8D6 show that the humanized antibody AAJ8D6 not only did not have a reduced binding affinity, but had a more significant improvement, and the required amount of antibody was reduced by more than half under the same binding strength compared to the chimeric antibody cAAJ8D6. The specific results are shown in Table 3:

TABLE 3

Comparison of average affinity constants between humanized antibody and chimeric antibody

| Name | EC50 (ng/mL) | $R^2$ |
|---|---|---|
| AAJ8D6 | 3.529 | 0.9923 |
| cAAJ8D6 | 7.830 | 0.9988 |

Example 3 Comparison of Binding Abilities of Humanized Antibody AAJ8D6 and Competitor ABT-700

The c-Met protein was prepared with a diluent to a final concentration of 2 μg/ml, and added to a microplate at 100 μl per well, overnight at 4° C. The solution in the well was discarded, and the plate was washed three times with PBST. The plate was added with a blocking solution at 300 μl/well and incubated at 37° C. for 2 h. The solution in the well was discarded, and the plate was washed three times with PBST. AAJ8D6 antibody and ABT-700 (i.e., telisotuzumab, its sequence information can be found at https://extranet-.who.int/soinn/mod/page/view.php?id=137&inn n=10366, the same below) were diluted to 9 concentrations, added to the 96-well plate and incubated for 2 h. The solution in the well was discarded, and the plate was washed three times with PBST. HRP detection antibody was prepared by adding diluent at a dilution of 1:5000, added at 100 μl per well, and incubated at 37° C. for 1 h. The solution in the well was discarded, and the plate was washed three times with PB ST. The plate was added with TMB color developing solution, incubated at room temperature for 2 min, and then added with Elisa stop solution. The plate was put on a reader to obtain the results, which are shown in Table 4 and FIG. 2.

Figure 2:
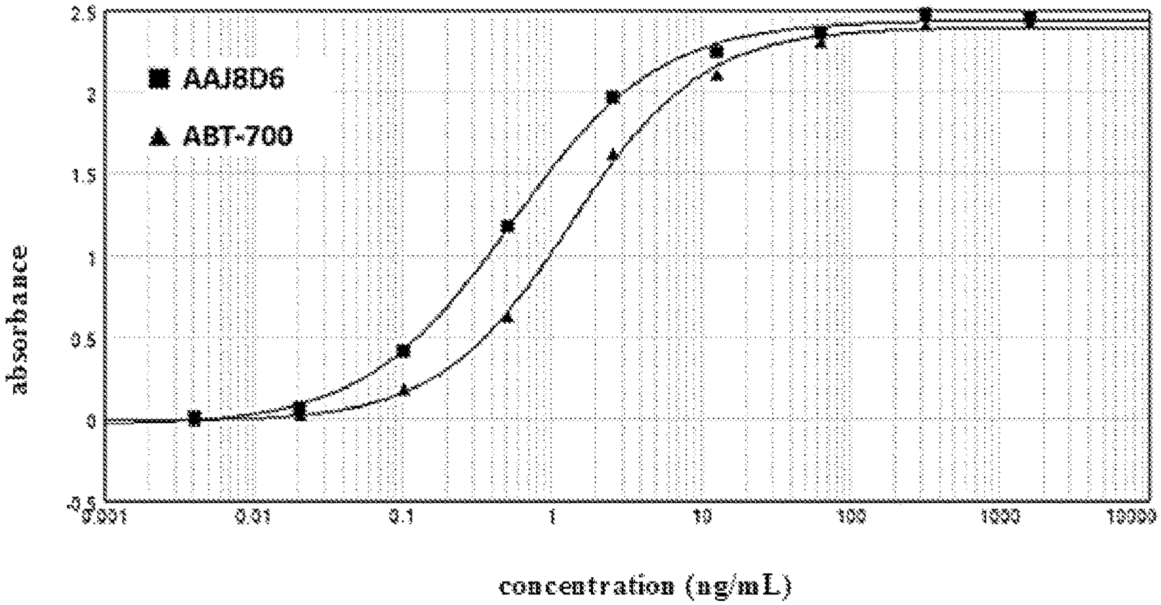
FIG. 2 shows the comparison of the binding ability of humanized antibody AAJ8D6 and ABT-700.

It can be seen from Table 4 and FIG. 2 that the EC50 value of AAJ8D6 was 0.54 ng/ml, and the EC50 value of ABT-700 was 1.33 ng/ml. The results show that the binding ability of AAJ8D6 antibody to c-Met antigen was significantly better than ABT-700.

TABLE 4

Comparison of the binding abilities of AAJ8D6 and ABT-700 to c-Met antigen

| | AAJ8D6 | ABT-700 |
|---|---|---|
| EC50 (ng/ml) | 0.54 | 1.33 |

Example 4 Preparation of Antibody-Drug Conjugates

The preparation of antibody-drug conjugates was performed according to a general conjugation method: a reducing agent and a protecting agent were prepared with purified water as follows: 1-20 mM TCEP (Tris-2-carboxyethyl-phosphine) and 1-20 mM DTPA (Diethylene triamine pentacetate acid) mother liquor, where the amount of reducing agent can be added within a concentration range according to the required coupling rate, were mixed with a concentration of monoclonal antibody (such as: 5-30 mg/mL) according to a volume ratio (1:1), and the final concentration molar ratio of TCEP to antibody was 0.5-6.0:1. The reaction was performed by stirring at 25° C. for 1 h. The TCEP-reduced antibody can be directly conjugated.

A concentration (5 mM) of a linker-active drug unit compound was prepared and dissolved in 25% DMSO (dimethyl sulfoxide). According to the molar ratio of drug to thio group of 0.32.8:1, the drug was slowly added, and the reaction was performed by stirring at 25° C. for 1-4 h. After the reaction, centrifugal ultrafiltration was performed 3 times with PBS buffer to purify and remove residual unreacted drugs and free small molecules such as DMSO, and SDS-PAGE electrophoresis and hydrophobic high performance liquid chromatography (HIC-HPLC) were used to detect the conjugation.

The linker-active drug unit compounds used in this example are Mc-Val-Cit-PAB-MMAE, D07-Val-Cit-PAB-MMAE and Py-MAA-Val-Cit-PAB-MMAE, whose structural formula are respectively as follows (for the synthesis methods, reference can be made to patent applications CN108853514A (page 14 of the specification), CN111433188A (page 53 of the specification), and WO2019223579A1 (pages 25-27 of the specification)).

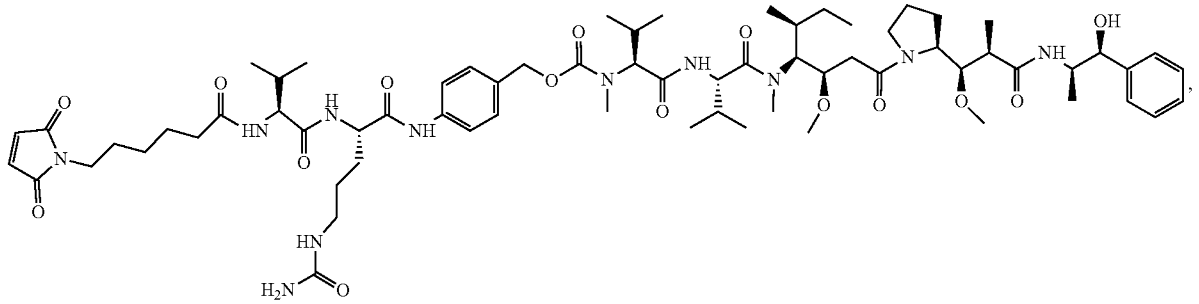
Mc-Val-Cit-PAB-MMAE
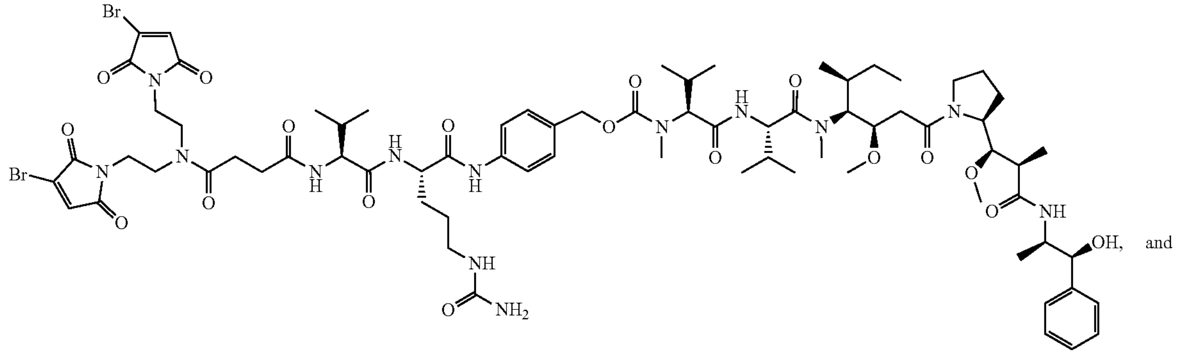
D07-Val-Cit-PAB-MMAE
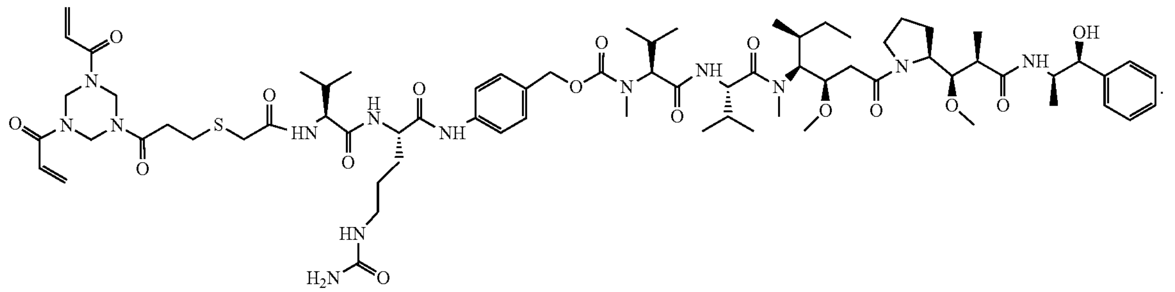
Py-MAA-Val-Cit-PAB-MMAE
The following ADCs were prepared by the above method (p was an integer selected from 1, 2, 3, 4, 5, 6, 7 and 8, q was an integer selected from 1, 2, 3 and 4, and Ab was the AAJ8D6 antibody provided by the present disclosure). The average DAR of these ADCs was 4.
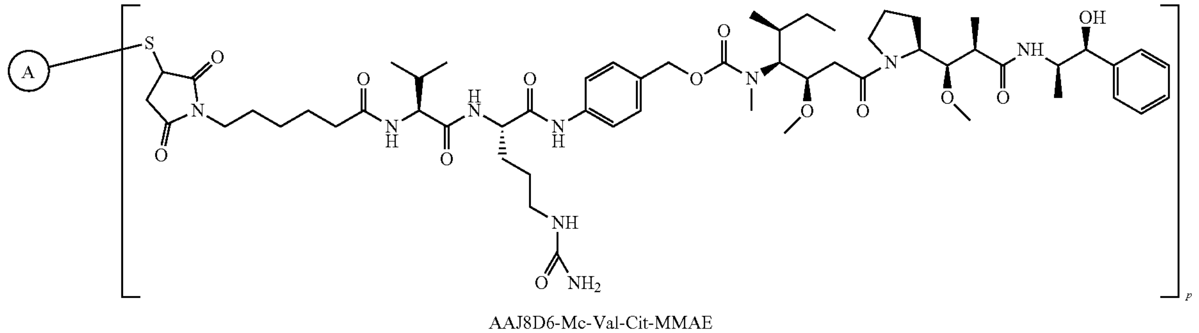
AAJ8D6-Mc-Val-Cit-MMAE -continued

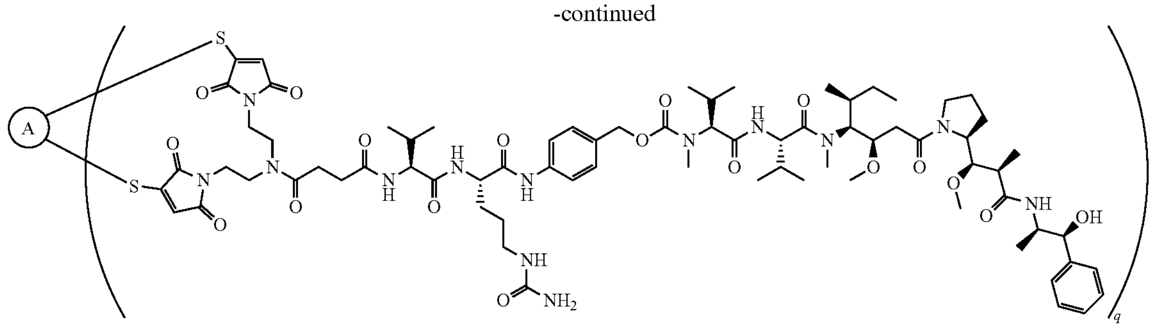

AAJ8D6-D07-Val-Cit-PAB-MMAE

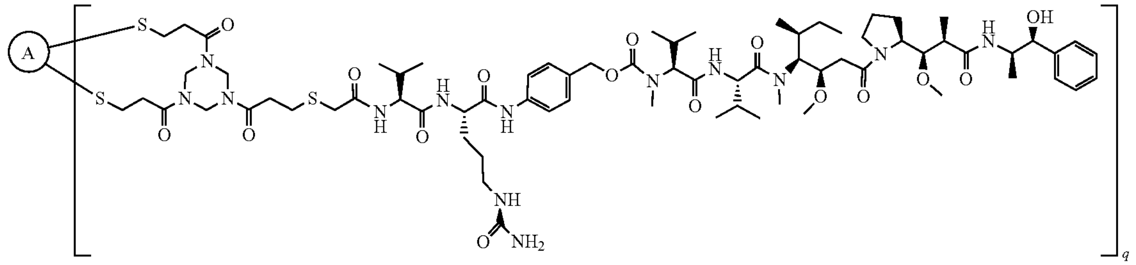

AAJ8D6-PY-Val-Cit-MMAE

In addition, this example also prepared an antibody-drug conjugate whose antibody part was ABT-700 antibody, the linking group was Mc-Val-Cit-PAB, and the active drug unit was MMAE, where p is an integer selected from 1, 2, 3, 4, 5, 6, 7 and 8, and the average DAR was 4.

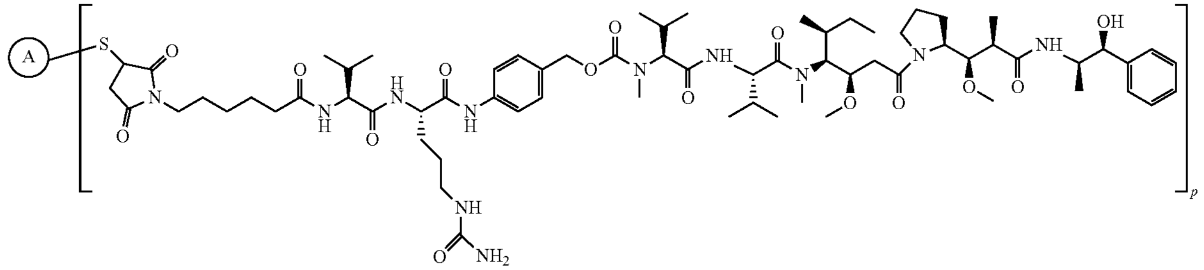

ABT-700-Mc-Val-Cit-MMAE

In addition, this example also prepared an antibody-drug conjugate of human immunoglobulin IgG1, Mc-Val-Cit-PAB and MMAE (i.e., IgG1-Mc-Val-Cit-PAB), where p was an integer selected from 1, 2, 3, 4, 5, 6, 7 and 8, and the average DAR was 4.

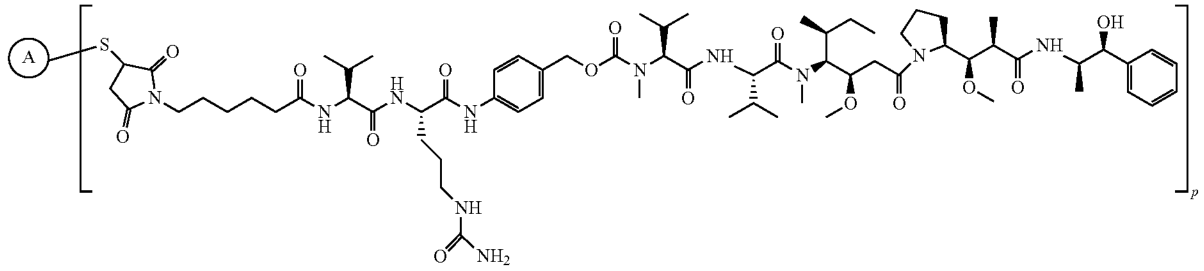

IgG1-Mc-Val-Cit-MMAE

Example 5 Endocytosis Experiment

Figure 3:
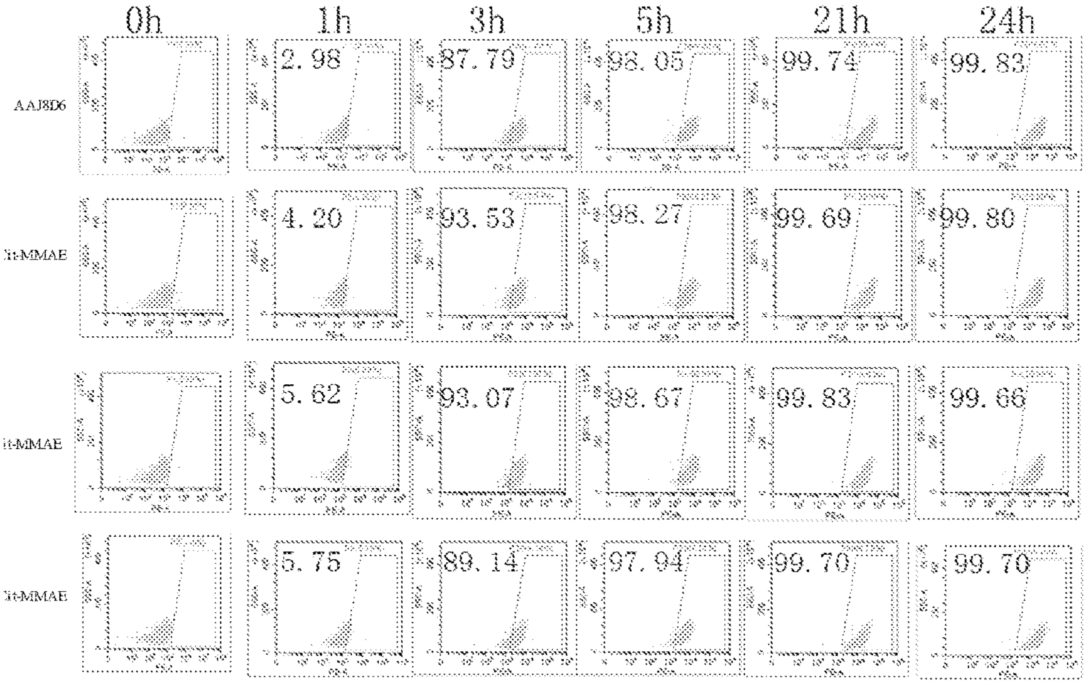
FIG. 3 shows the endocytosis effect of humanized antibody AAJ8D6, AAJ8D6-Mc-Val-Cit-MMAE, AAJ8D6-PY-Val-Cit-MMAE, and AAJ8D6-D07-Val-Cit-MMAE.
Figure 4A:
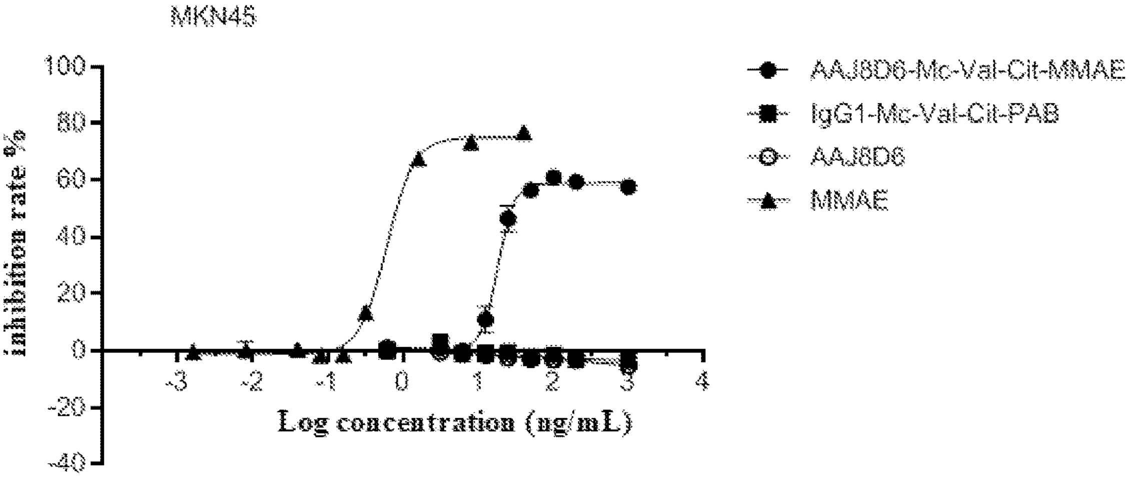
FIGS. 4A-4D show the comparison of the cytotoxic activity of humanized antibody AAJ8D6, its antibody-drug conjugate AAJ8D6-Mc-Val-Cit-MMAE and the control group, among which the representative cell line in FIG. 4A is MKN-45, the representative cell line in FIG. 4B is SNU-620, the representative cell line in FIG. 4C is HT29, and the representative cell line in FIG. 4D is BXPC-3.
Figure 4B:
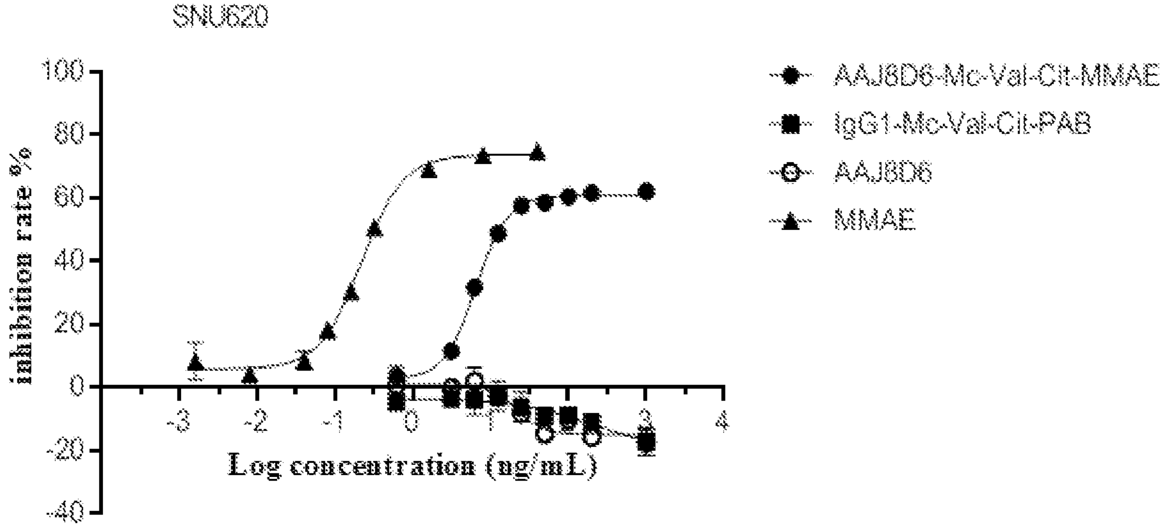
Figure 4C:
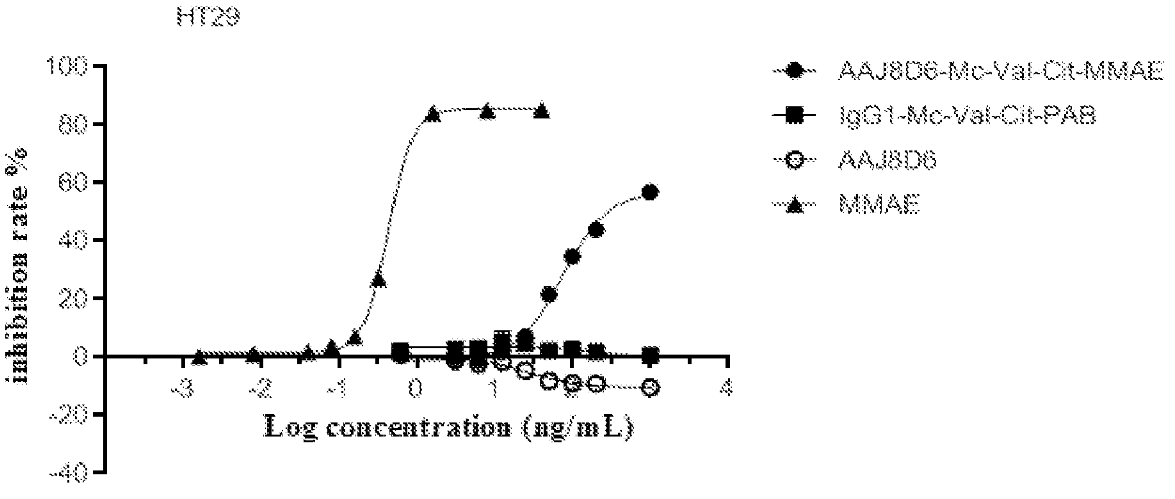
Figure 4D:
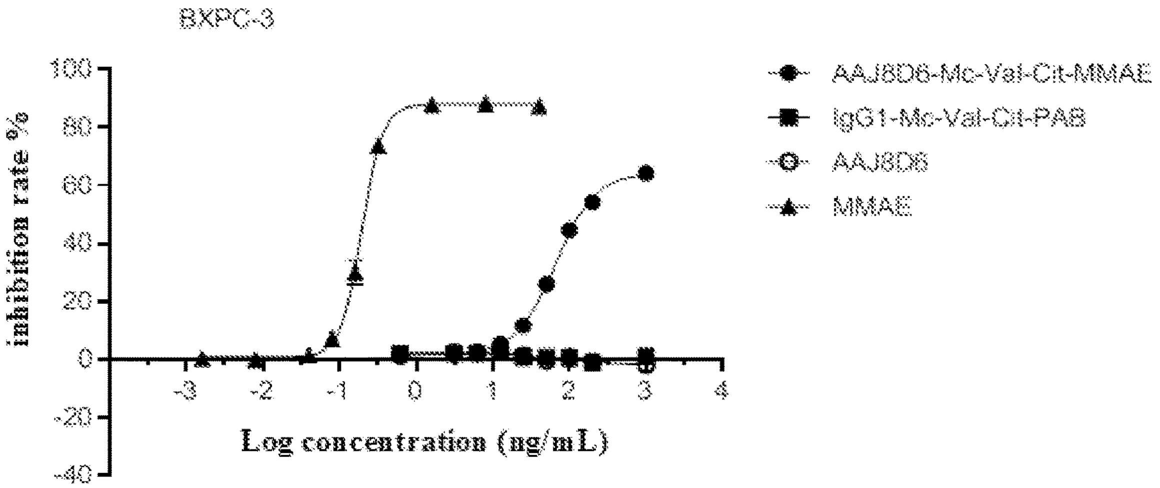

HT29 cells were resuspended in 6-well plates at approximately $1\times10^5$ cells per well. AAJ8D6 antibody, AAJ8D6-Mc-Val-Cit-MMAE, AAJ8D6-PY-Val-Cit-MMAE and AAJ8D6-D07-Val-Cit-MMAE were conjugated to pHAb amine-reactive dyes, respectively, and then diluted with cell culture medium to 10 μg/ml. 100 μl of AAJ8D6 antibody, AAJ8D6-Mc-Val-Cit-MMAE, AAJ8D6-PY-Val-Cit-MMAE and AAJ8D6-D07-Val-Cit-MMAE dye complexes were added to cells and incubated at 37° C. for indicated times (0 h, 1 h, 3 h, 5 h, 21 h and 24 h). The endocytosis effects of AAJ8D6 antibody, AAJ8D6-Mc-Val-Cit-MMAE, AAJ8D6-PY-Val-Cit-MMAE and AAJ8D6-D07-Val-Cit-MMAE were measured by flow cytometry. After 24 h, the samples were significantly endocytosed in HT29 cells; after 3 h, the endocytosis effects were all about 90%. It can be seen that the humanized antibody provided by the present disclosure and the prepared ADCs had good endocytosis effects, which will be able to efficiently deliver the drug into the target cells. The results are shown in FIG. 3.

Example 6 Cytotoxic Activities of Humanized Antibody AAJ8D6 and its Antibody-Drug Conjugate (AAJ8D6-Mc-Val-Cit-MMAE)

Cells MKN-45, SNU-620, HT29, and BXPC-3 with different c-Met expression levels in exponential doubling phase were seeded in 96-well plates, respectively, and incubated overnight in a 37° C., 5% $CO_2$ incubator. AAJ8D6, AAJ8D6-Mc-Val-Cit-MMAE and IgG1-Mc-Val-Cit-PAB were prepared in complete medium to a concentration of 1.25-2000 ng/mL, and MMAE was prepared in complete medium to a concentration of 0.0021-80 ng/mL. They were added to the plate at 100 μL per well with triplicate wells set up for each concentration, and a blank control group was set as well. After 72±2 h of drug action, the plate was added with CCK-8 reagent, incubated at 37° C., 5% $CO_2$ incubator for 1 to 4 h, and detected for OD value of each well at 450 nm of a microplate reader. The inhibition rate (IR) was calculated as: IR %=(OD of blank-OD of drug)×100/OD of blank. Four-parameter fitting was performed on the inhibition rate and drug concentration to calculate $IC_{50}$.

Results and conclusions: As shown in FIGS. 4A, 4B, 4C and 4D, the cytotoxic activity of AAJ8D6-Mc-Val-Cit-MMAE was positively correlated with the expression of c-Met in the cell line, while AAJ8D6 had no cytotoxic effect on target cells. The cytotoxicity of AAJ8D6-Mc-Val-Cit-MMAE mainly came from MMAE, which had targeting ability compared with IgG1-Mc-Val-Cit-PAB.

Example 7 In vitro efficacy differences between antibody-drug conjugate AAJ8D6-Mc-Val-Cit-MMAE and antibody-drug conjugate ABT-700-Mc-Val-Cit-MMAE The suspension of human colon cancer cell line HT29 was added to a 96-well plate at a density of 100 μL/well and 5000 cells/well, and placed in a water-saturated 37° C., $CO_2$ incubator overnight. The antibody-drug conjugate AAJ8D6-Mc-Val-Cit-MMAE and the antibody-drug conjugate ABT-700-Mc-Val-Cit-MMAE were serially diluted and added to a 96-well plate containing cells at 100 μL/well. The plate was placed in a 37° C. incubator to culture for another 72 h. The OD values at 450 nm were read with the microplate reader, and the inhibition rate (IR) was calculated as: IR %=(OD of blank-OD of drug)×100/OD of blank. The curve fitting software Softmax Pro7.0.3 Gxp was used to calculate $IC_{50}$.

Figure 5:
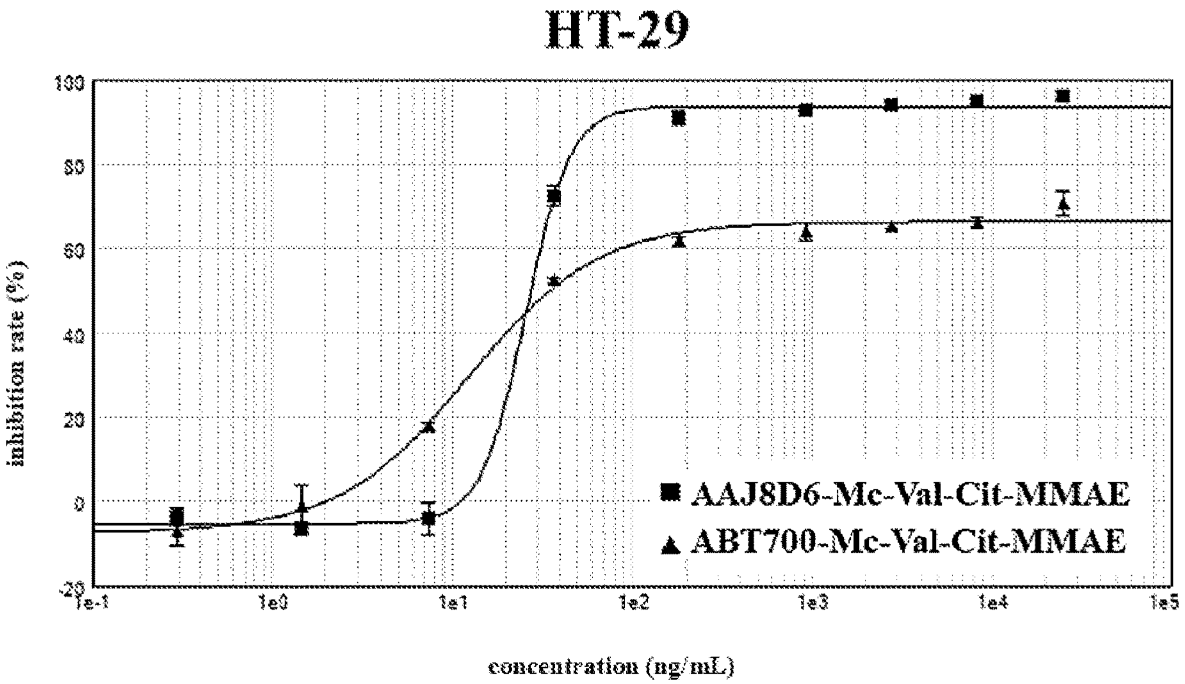
FIG. 5 shows the comparison of the maximum inhibition rate of antibody-drug conjugate AAJ8D6-Mc-Val-Cit-MMAE and antibody-drug conjugate ABT-700-Mc-Val-Cit-MMAE.

The results are shown in Table 5 and FIG. 5. The experimental results showed that the $IC_{50}$ maximum inhibition rate of AAJ8D6-Mc-Val-Cit-MMAE was significantly better than that of the antibody-drug conjugate ABT-700-Mc-Val-Cit-MMAE, indicating that the in vitro efficacy of AAJ8D6-Mc-Val-Cit-MMAE was better than that of the antibody-drug conjugate ABT-700-Mc-Val-Cit-MMAE.

TABLE 5

Results of maximum inhibition rate of antibody-drug conjugates on cells in vitro

| ADC | Inhibition rate (%) |
|---|---|
| AAJ8D6-Mc-Val-Cit-MMAE | 93.62 |
| ABT-700-Mc-Val-Cit-MMAE | 66.28 |

Example 8 Efficacy of Antibody-Drug Conjugate AAJ8D6-Mc-Val-Cit-MMAE on Human Gastric Cancer Cell MKN-45Subcutaneously Transplanted Tumors in Balb/c Nude Mice 42 Balb/c nude mice aged 6-7 weeks were taken, and 0.1 mL of MKN-45 cell suspension ($2.4\times10^6$ cells/mouse) was subcutaneously implanted in the back of the right armpit of the mice. When the tumor grew to about 100-300 $mm^3$, according to the tumor volume, mice were randomly divided into the Vehicle (PBS) group, IgG1-Mc-Val-Cit-PAB (3 mg/kg) group, antibody-drug conjugate AAJ8D6-Mc-Val-Cit-MMAE (0.75 mg/kg) group, antibody-drug conjugate AAJ8D6-Mc-Val-Cit-MMAE (1.5 mg/kg) group, antibody-drug conjugate AAJ8D6-Mc-Val-Cit-MMAE (3 mg/kg) and humanized antibody AAJ8D6 (3 mg/kg) group, 6 tumor-bearing mice in each group. Each group was administered intravenously, once a week, for a total of 3 times, and measured for long diameter and short diameter of tumor and body weight twice a week during the administration. On Day 21 after administration, the tumor inhibition rate ($TGI_{RTV}$) was calculated for efficacy evaluation.

Calculation formula:

Tumor volume: $TV=D1\times D2^2/2$, where D1 and D2 represent the long diameter and the short diameter of the tumor, respectively;

Relative tumor volume: $RTV=TV_n/TV_0$, where $T_{V0}$ is the tumor volume before administration, and $TV_n$ is the tumor volume at each measurement;

Relative tumor inhibition rate: $TGI_{RTV}(\%)=(1-T_{RTV}/C_{RTV})$ 100%, $T_{RTV}$ means RTV of drug administration group or positive control group, and $C_{RTV}$ means RTV of negative control group.

TABLE 6

Tumor volume and inhibition rate of each experimental group and control group on MKN-45 subcutaneously transplanted tumor in nude mice

| Group | Dose (mg/kg) | TV ($mm^3$) D 0 | TV ($mm^3$) D 21 | $TGI_{RTV}$ % |
|---|---|---|---|---|
| Vehicle (PBS) | — | 201 ± 25 | 1509 ± 276 | — |
| AAJ8D6 | 3 | 200 ± 24 | 1633 ± 77 | −15 |
| IgG1-Mc-Val-Cit-PAB | 3 | 201 ± 23 | 1314 ± 177 | 11 |
| AAJ8D6-Mc-Val-Cit-MMAE | 0.75 | 200 ± 22 | 1135 ± 74 | 22 |
| | 1.5 | 203 ± 23 | 415 ± 50 | 70 |
| | 3 | 201 ± 22 | 36 ± 9 | 99 |

Figure 6:
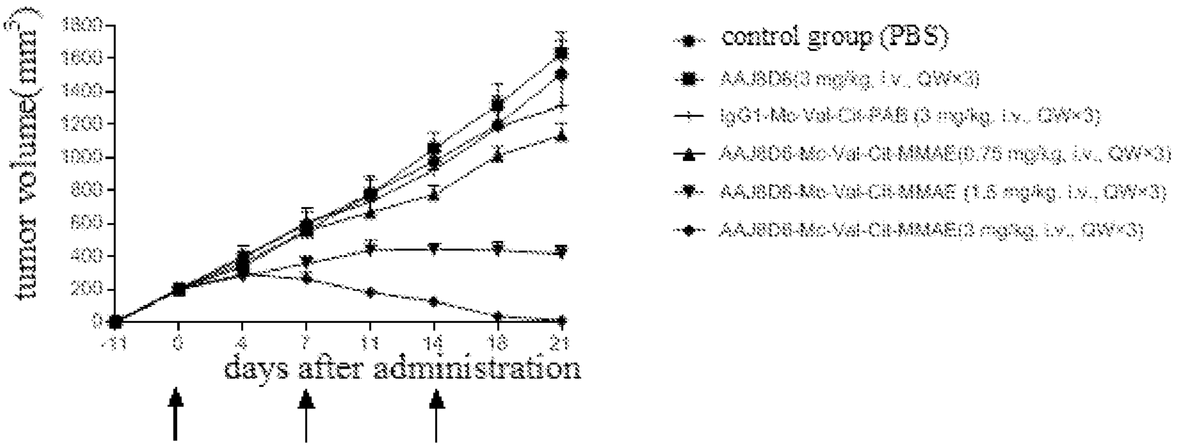
FIG. 6 shows the comparison of the therapeutic effects of antibody-drug conjugate AAJ8D6-Mc-Val-Cit-MMAE and the control group on MKN-45 tumor-bearing nude mice.

Result and conclusion: The inhibitory effect of each experimental group and control group on MKN-45 subcutaneously transplanted tumor in nude mice is shown in Table 6 and FIG. 6, and Table 6 shows tumor volume and inhibition rate of each experimental group and control group on MKN-45 subcutaneously transplanted tumor in nude mice, and FIG. 6 shows the tumor growth curve after administration. The experimental results showed that the antibody-drug conjugate AAJ8D6-Mc-Val-Cit-MMAE had a significant inhibitory effect on the MKN-45 subcutaneously transplanted tumor in nude mice.

Example 9 Efficacy of Antibody-Drug Conjugate AAJ8D6-Mc-Val-Cit-MMAE on Mouse PDX Model (Gastric Cancer GA0046)

The mouse PDX (patient-derived xenograft) model of gastric cancer GA0046 was constructed by transplanting tumor tissue from human patients with gastric cancer into severely immunodeficient mice, in which the gastric cancer tissue grew to form a transplanted tumor.

The tumor-bearing mice with good tumor growth were picked and euthanized, and the tumors were removed and cut into small pieces (2-3 mm in diameter), which were then inoculated on the right shoulder of the mice to establish a subcutaneous gastric cancer model. The tumor growth was regularly observed, and when the tumor grew to an average volume of about 100-150 mm 3, according to the tumor size and the weight of mice, mice were randomly divided into Vehicle (PBS) group, antibody-drug conjugate AAJ8D6-Mc-Val-Cit-MMAE (10 mg/kg) group, and IgG1-Mc-Val-Cit-PAB (10 mg/kg) group, 6 tumor-bearing mice in each group. Each group was administered intravenously, once a week, for a total of 2 times, for a total of 21 times. The long diameter and short diameter of tumor and body weight were measured twice a week during the administration. On Day 21 after administration, the tumor inhibition rate ($TGI_{RTV}$) was calculated for efficacy evaluation.

Calculation formula:

Tumor volume: $TV=D1\times D2^2/2$, where D1 and D2 represent the long diameter and the short diameter of the tumor, respectively;

Relative tumor volume: $RTV=TV_n/TV_0$, where $TV_0$ is the tumor volume before administration, and $TV_n$ is the tumor volume at each measurement;

Relative tumor inhibition rate: $TGI_{RTV}(\%)=(1-T_{RTV}/C_{RTV})$ 100%, $T_{RTV}$ means RTV of drug administration group or positive control group, and $C_{RTV}$ means RTV of negative control group.

Figure 7:
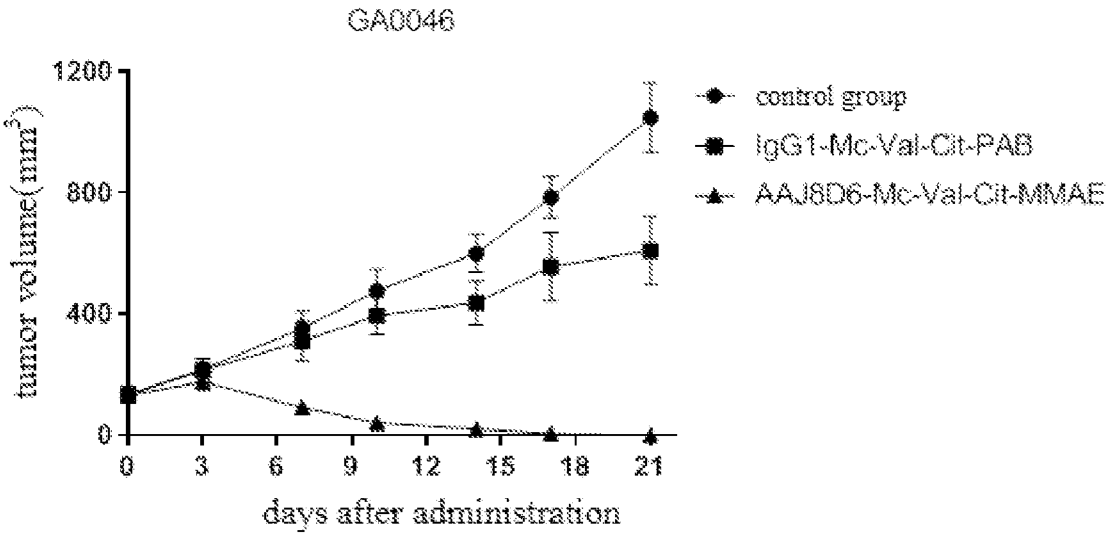
FIG. 7 shows the comparison of the efficacy of antibody-drug conjugate AAJ8D6-Mc-Val-Cit-MMAE and the control group on a PDX model of mice (gastric cancer GA0046)

Results and conclusions: The tumor inhibitory effects of each experimental group and control group on the mouse gastric cancer PDX model (GA0046) are shown in Table 7 and FIG. 7, in which Table 7 shows the tumor volume of and inhibition rate on the mouse gastric cancer PDX model (GA0046), and FIG. 7 shows the tumor growth curve after administration. The results showed that the antibody-drug conjugate AAJ8D6-Mc-Val-Cit-MMAE had a significant anti-tumor effect on the gastric cancer GA0046PDX tumor model at a dose of 10 mg/kg.

TABLE 7

Tumor volume and inhibition rate of antibody-drug conjugate AAJ8D6-Mc-Val-Cit-MMAE on mouse PDX model of gastric cancer GA0046

| Group | Tumor volume ($mm^3$) $TV_{D0}$ | Tumor volume ($mm^3$) $TV_{D21}$ | Inhibition rate (%) |
|---|---|---|---|
| Vehicle(PBS) | 133.90 ± 18.34 | 1048.57 ± 112.90 | — |
| IgG1-Mc-Val-Cit-PAB | 134.55 ± 26.59 | 609.72 ± 114.26 | 42.13 |
| AAJ8D6-Mc-Val-Cit-MMAE | 131.38 ± 17.85 | 0.00 ± 0.00 | 100.00 |

Example 10 Efficacy of Antibody-Drug Conjugate AAJ8D6-Mc-Val-Cit-MMAE on Mouse PDX Model (Lung Cancer LU2503)

The mouse PDX (patient-derived xenograft) model of lung cancer LU2503 was constructed by transplanting tumor tissue from human patients with lung cancer into severely immunodeficient mice, in which the gastric cancer tissue grew to form a transplanted tumor.

The tumor-bearing mice with good tumor growth were picked and euthanized, and the tumors were removed and cut into small pieces (2-3 mm in diameter), which were then inoculated on the right shoulder of the mice to establish a subcutaneous lung cancer model. The tumor growth was regularly observed, and when the tumor grew to an average volume of about 150 $mm^3$, according to the tumor size and the body weight of mice, mice were randomly divided into Vehicle (PBS) group, humanized antibody AAJ8D6 (10 mg/kg) group, and low, medium and high concentrations of antibody-drug conjugate AAJ8D6-Mc-Val-Cit-MMAE (1.1 mg/kg, 3.3 mg/kg, 10 mg/kg) groups, 6 tumor-bearing mice in each group. Mice in the antibody-drug conjugate AAJ8D6-Mc-Val-Cit-MMAE and humanized antibody AAJ8D6 groups were administered intravenously, once a week, for a total of 2 times. The long diameter and short diameter of tumor and body weight were measured twice a week during the administration. On Day 21 after administration, the tumor inhibition rate ($TGI_{RTV}$) was calculated for efficacy evaluation.

Calculation formula:

Tumor volume: $TV=D1\times D2^2/2$, where D1 and D2 represent the long diameter and the short diameter of the tumor, respectively;

Relative tumor volume: $RTV=TV_n/TV_0$, where $TV_0$ is the tumor volume before administration, and $TV_n$ is the tumor volume at each measurement;

Relative tumor inhibition rate: $TGI_{RTV}(\%)=(1-T_{RTV}/C_{RTV})$ 100%, $T_{RTV}$ means RTV of drug administration group or positive control group, and $C_{RTV}$ means RTV of negative control group.

Figure 8:
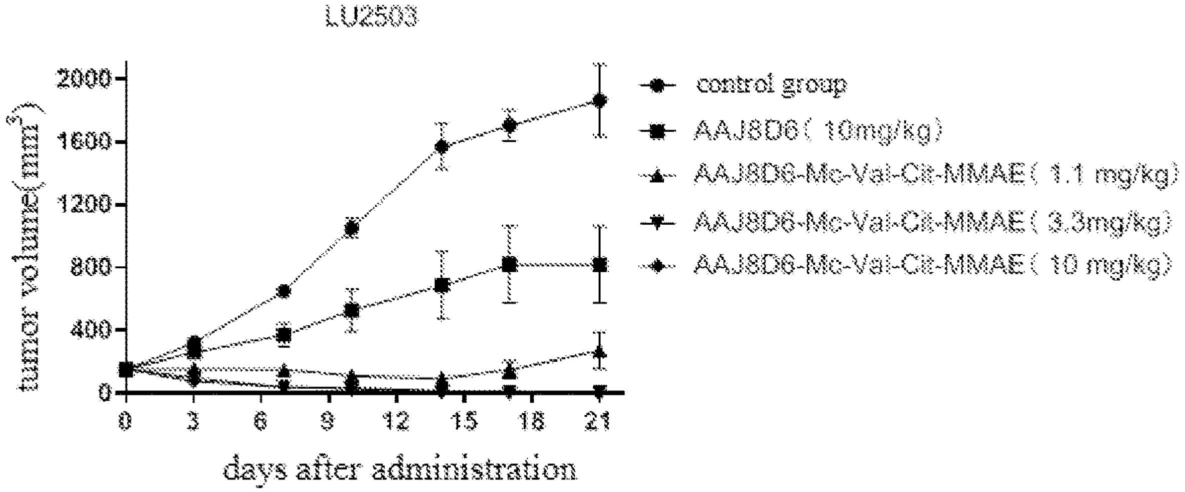
FIG. 8 shows the comparison of the efficacy of antibody-drug conjugate AAJ8D6-Mc-Val-Cit-MMAE and the control group on a PDX model of mice (lung cancer LU2503).

Results and conclusions: The tumor inhibitory effects of each experimental group and control group on the mouse lung cancer PDX model (LU2503) are shown in Table 8 and FIG. 8, in which Table 8 shows the tumor volume of and inhibition rate on the mouse lung cancer PDX model (LU2503), and FIG. 8 shows the tumor growth curve after administration. The results showed that the antibody-drug conjugate AAJ8D6-Mc-Val-Cit-MMAE had a significant anti-tumor effect on the LU2503 tumor model when used alone at doses of 1.1 mg/kg, 3.3 mg/kg and 10 mg/kg, and especially at 3.3 mg/kg and 10 mg/kg, the tumors of mice completely disappeared.

TABLE 8

Tumor volume and inhibition rate of ADC on mouse PDX model (LU2503)

| Group | Dose (mg/kg) | Tumor volume ($mm^3$) $TV_{D0}$ | Tumor volume ($mm^3$) $TV_{D21}$ | Inhibition rate (%) |
|---|---|---|---|---|
| Vehicle (PBS) | — | 150.43 ± 6.69 | 1864.30 ± 228.19 | — |
| AAJ8D6 | 10 | 157.05 ± 9.21 | 1165.02 ± 163.71 | 37.60 |
| AAJ8D6-Mc- | 1.1 | 150.47 ± 8.46 | 270.61 ± 116.64 | 85.49 |
| Val-Cit- | 3.3 | 150.53 ± 8.21 | 0.00 ± 0.00 | 100.00 |
| MMAE | 10 | 150.33 ± 6.47 | 0.00 ± 0.00 | 100.00 |

The above examples show that the antibody-drug conjugate AAJ8D6-Mc-Val-Cit-MMAE provided by the present disclosure has a very significant therapeutic effect on c-Met positive tumors.

The principles and implementations of the present disclosure are illustrated by specific examples herein, and the descriptions of the above examples are only used to help understand the method and the central idea of the present disclosure. Several improvements and modifications can also be made to the present disclosure without departing from the principles of the present disclosure, and these improvements and modifications also fall within the protection of the claims of the present disclosure.

The invention claimed is:

1. A humanized antibody targeting c-Met or antigen-binding fragment thereof, comprising a heavy chain variable region and a light chain variable region, wherein:

(1) the heavy chain variable region has CDRs 1-3 set forth in SEQ ID NOs: 0.3 respectively determined by Kabat method; and (2) the light chain variable region has CDRs 1-3 set forth in SEQ ID NOs: 4-6 respectively determined by Kabat method.

2. The antibody or antigen-binding fragment thereof according to claim 1, wherein the humanized antibody or antigen-binding fragment thereof is selected from the group consisting of monoclonal antibody, bispecific antibody, multispecific antibody, recombinant protein comprising the antigen-binding fragment, Fab fragment, F(ab') fragment, $F(ab')_2$ fragment, Fv fragment, dAb, Fd, and single chain antibody (scFv).

3. The antibody or antigen-binding fragment thereof according to claim 1, further comprising a constant region of an immunoglobulin, wherein the immunoglobulin is selected from the group consisting of IgG1, IgG2, IgG3 and IgG4.

4. The antibody or antigen-binding fragment thereof according to claim 1, wherein:

(1) the heavy chain variable region has an amino acid sequence shown in SEQ ID NO: 7; and/or (2) the light chain variable region has an amino acid sequence shown in SEQ ID NO: 8.

5. The antibody or antigen-binding fragment thereof according to claim 4, wherein the humanized antibody targeting c-Met comprises a heavy chain and a light chain, and (1) the heavy chain has an amino acid sequence shown in SEQ ID NO: 9; and/or (2) the light chain has an amino acid sequence shown in SEQ ID NO:10.

6. An isolated polynucleotide encoding the antibody or antigen-binding fragment thereof according to claim 1.

7. A nucleic acid construct comprising the polynucleotide according to claim 6.

8. The nucleic acid construct according to claim 7, wherein the nucleic acid construct is an expression vector, and the polynucleotide is operably linked to a regulatory sequence that permits expression of a polypeptide encoded by the polynucleotide in a host cell or cell-free expression system.

9. A host cell comprising the polynucleotide according to claim 6, wherein the host cell is preferably selected from the group consisting of a prokaryotic cell, eukaryotic cell, yeast cell, mammalian cell and *E. coli* cel.

10. A host cell comprising the polynucleotide according to claim 9, wherein the host cell is selected from the group consisting of a CHO cell, NS0 cell, Sp2/0 cell and BHK cell.

11. An antibody-drug conjugate targeting c-Met, comprising the antibody or antigen-binding fragment thereof according to claim 1 coupled with one or more therapeutic agents.

12. The antibody-drug conjugate according to claim 11, wherein the therapeutic agent is selected from the group consisting of a cytotoxic molecule, immunoenhancer and radioisotope, the cytotoxic molecule is selected from the group consisting of a tubulin inhibitor and a DNA damage agent.

13. The antibody-drug conjugate according to claim 12, wherein the antibody-drug conjugate has a structural formula of A-(L-U)n, wherein A represents an antibody or antigen-binding fragment thereof; U is an active drug unit; L is any linking group, and L is covalently linked to A and U, respectively; n is an integer selected from 1, 2, 3, 4, 5, 6, 7 or 8; and A is linked to 1, 2, 3, 4, 5, 6, 7 or 8 of U through one or more L;

wherein A comprises a heavy chain variable region and a light chain variable region, wherein:

(1) the heavy chain variable region has CDRs 1-3 set forth in SEQ ID NOs: 1-3 respectively determined by Kabat method, and (2) the heavy chain variable region has CDRs 1-3 set forth in SEQ ID NOs: 4-6 respectively determined by Kabat method.

14. The antibody-drug conjugate according to claim 13, wherein L is covalently linked to the amino residue or thiol residue on A.

15. The antibody-drug conjugate according to claim 14, wherein L comprises a cleavable linker and a non-cleavable linker.

16. The antibody-drug conjugate according to claim 15, wherein the cleavable linker comprises a peptide unit comprising 2-20 amino acids.

17. The antibody-drug conjugate according to claim 16, wherein the peptide unit is selected from the group consisting of -valine-citrulline-(-Val-Cit-), -glycine-glycine-phenylalanine-glycine-(-Gly-Gly-Phe-Gly-), -valine-alanine-(-Val-Ala-), -valine-lysine-(-Val-Lys-), -valine-arginine-(-Val-Arg-), - phenylalanine-citrulline-(-Phe-Cit-), -phenylalanine-lysine-(-Phe-Lys-), -phenylalanine-arginine-(-Phe-Arg-) and a combination thereof.

18. The antibody-drug conjugate according to claim 15, wherein L comprises a structure selected from the group consisting of:

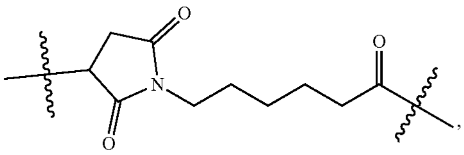,

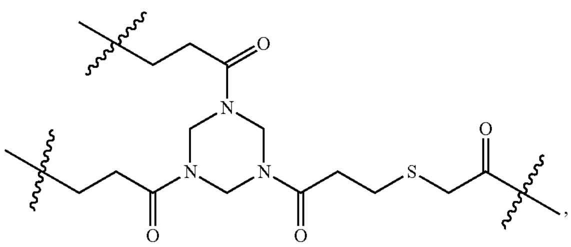,

-continued
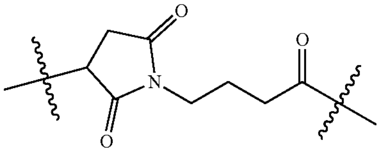
,
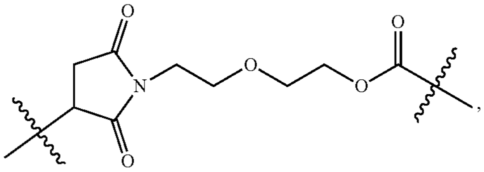
,
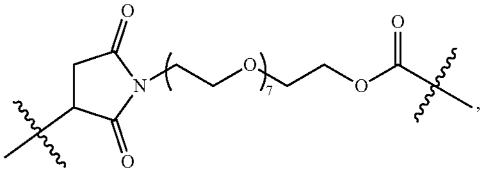
,
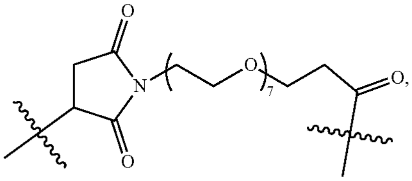
,
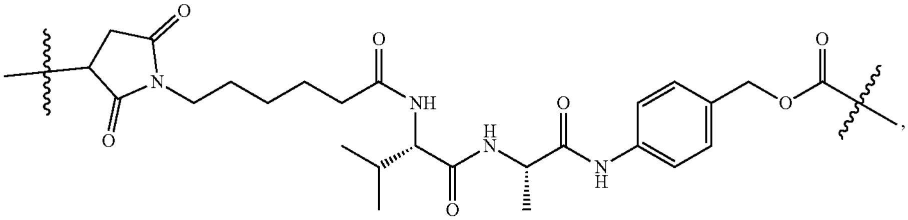
,
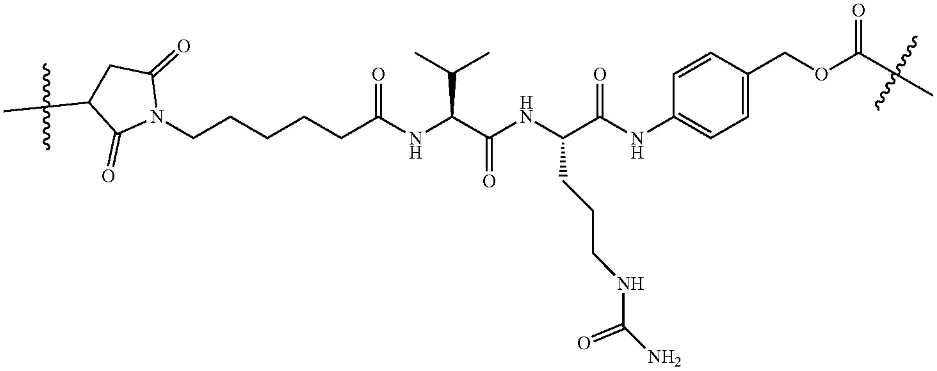
,
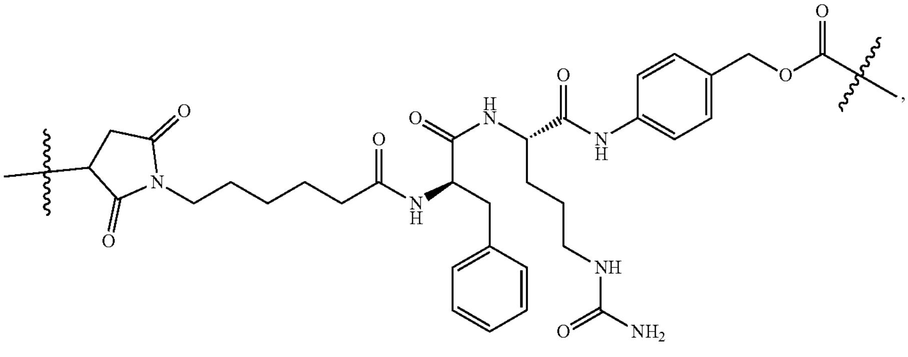
,
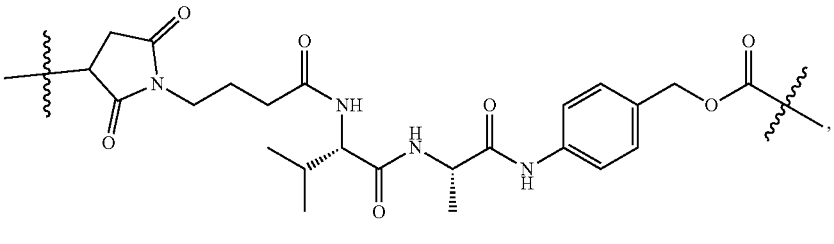
, -continued
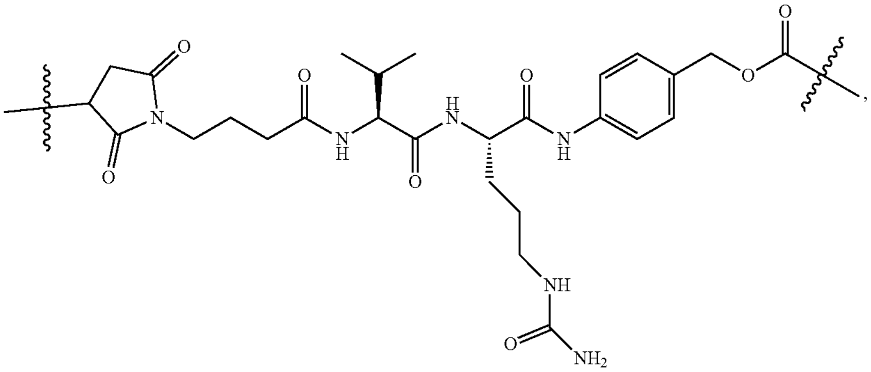
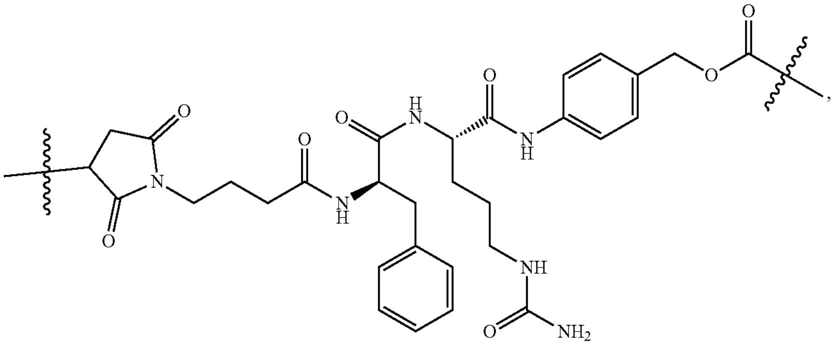
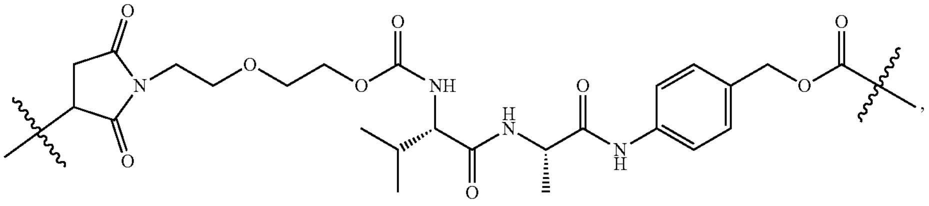
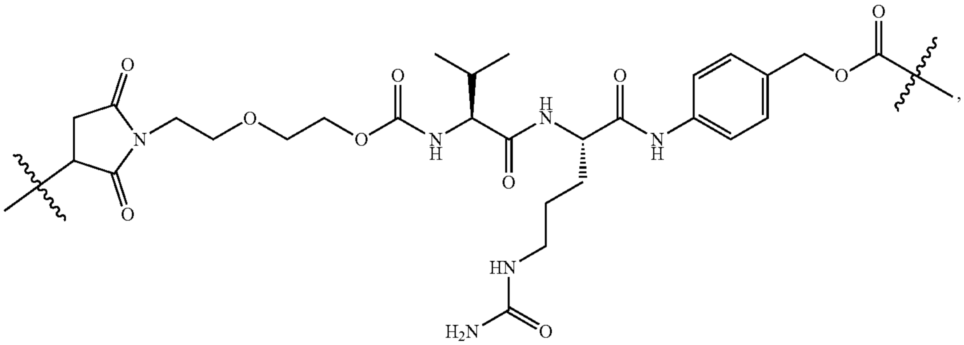
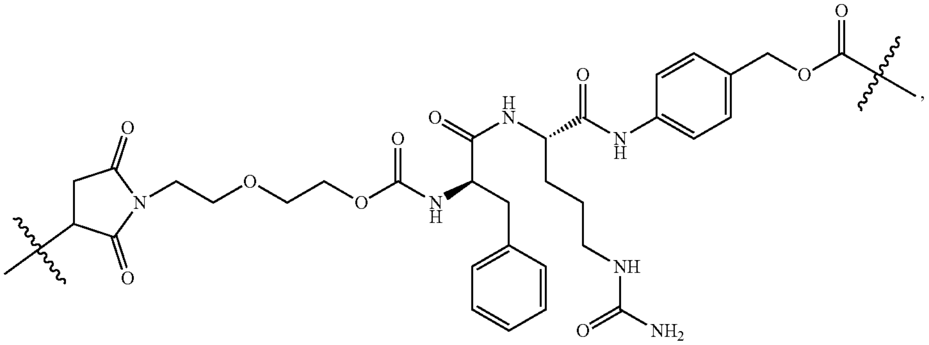

-continued
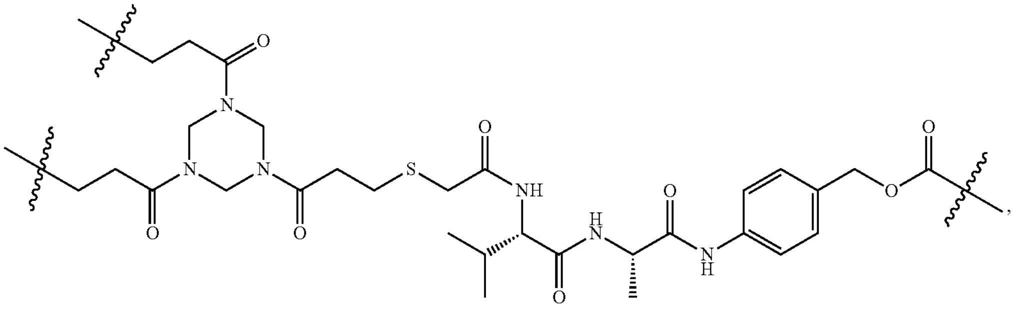
,
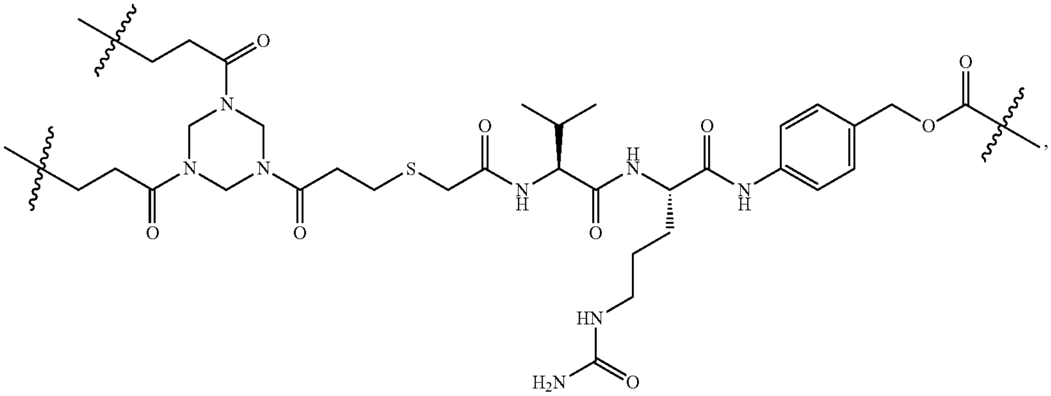
,
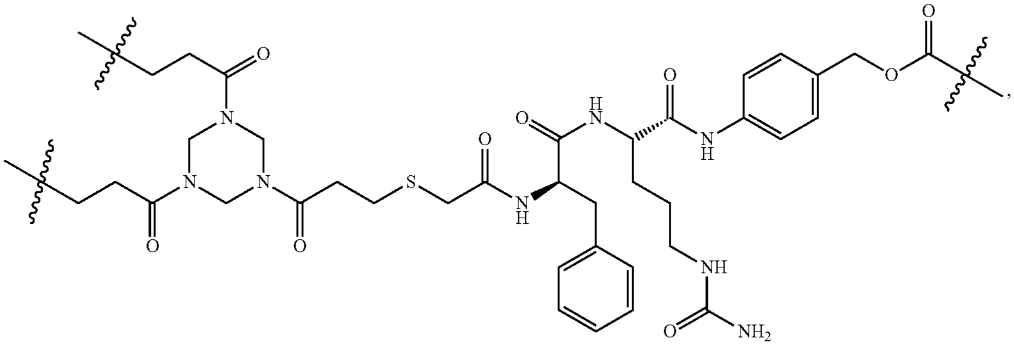
,
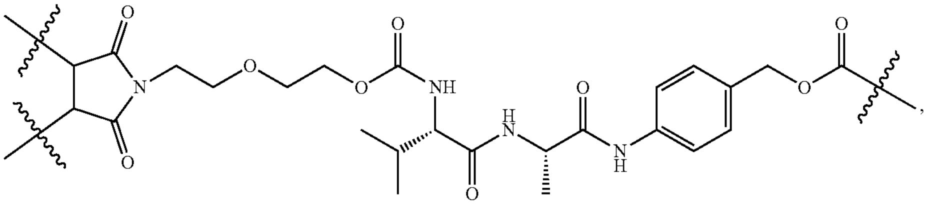
,
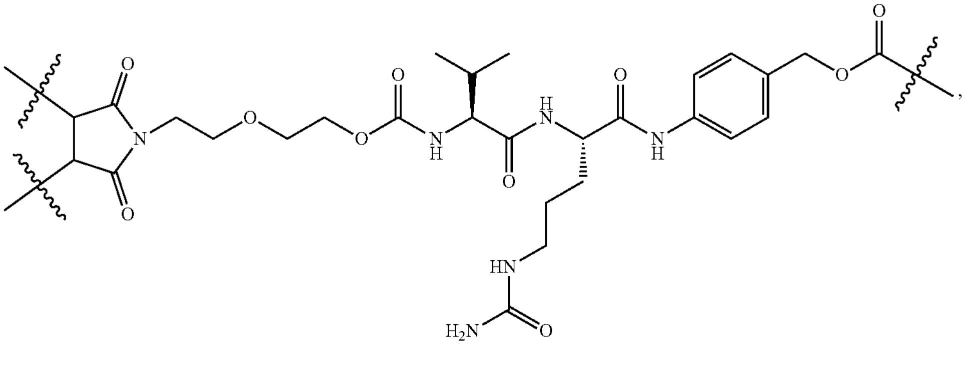
,

-continued
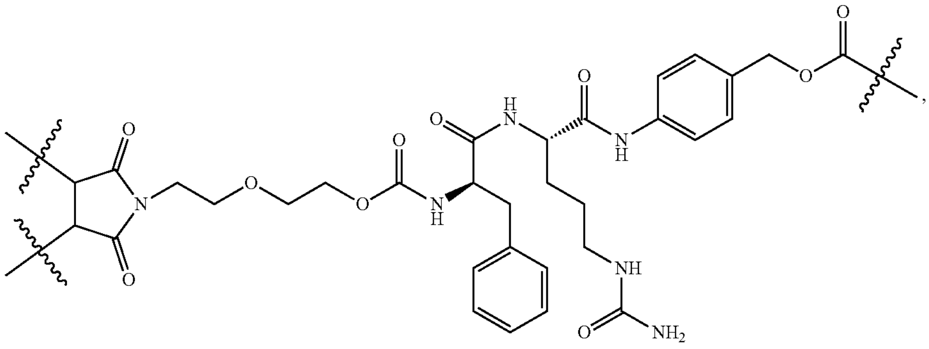
,
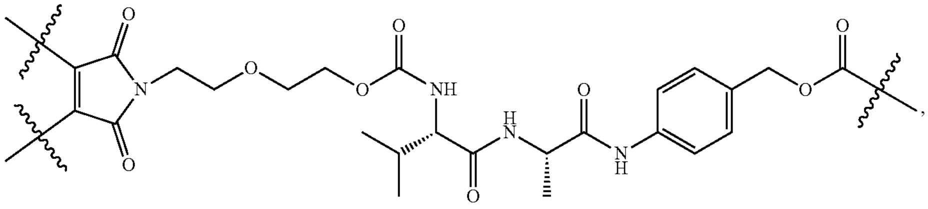
,
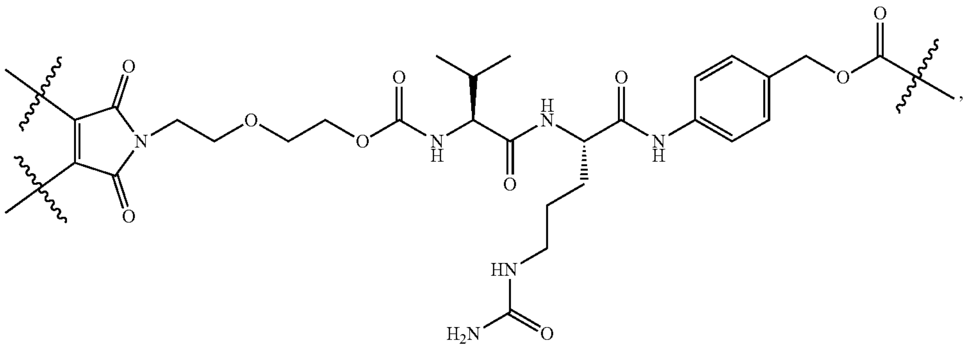
,
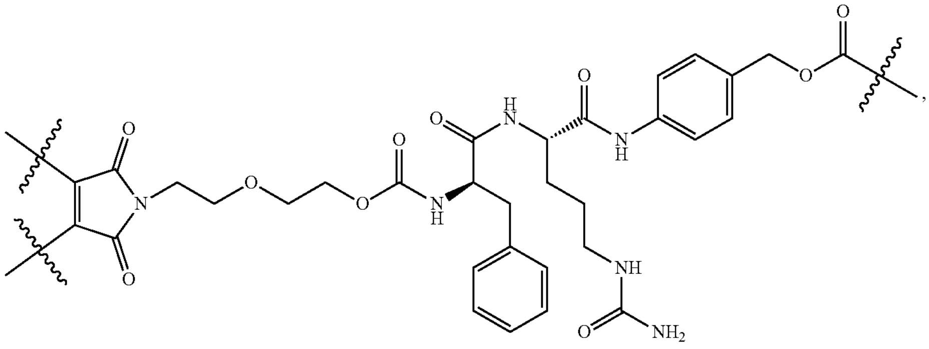
,
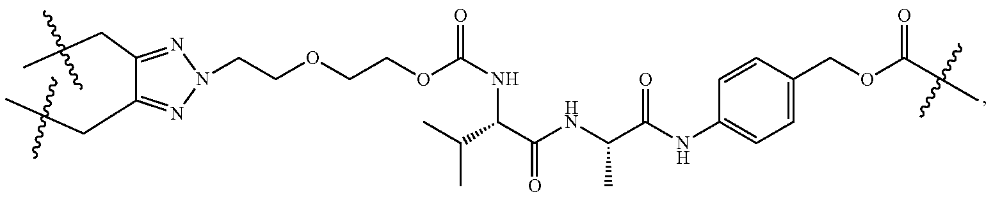
, -continued
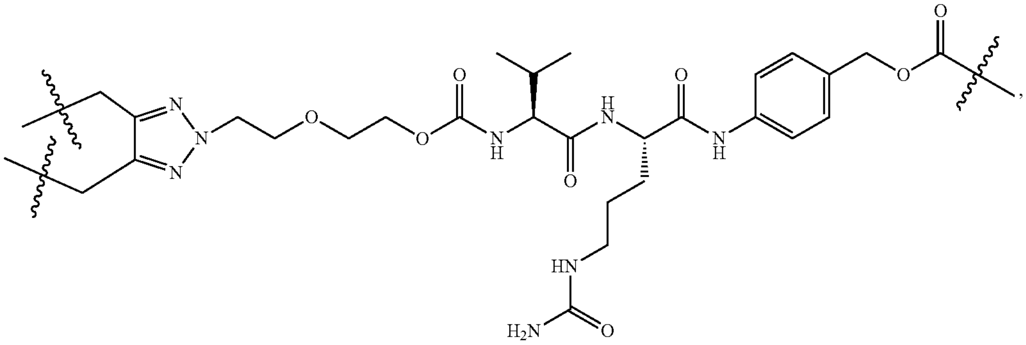
,
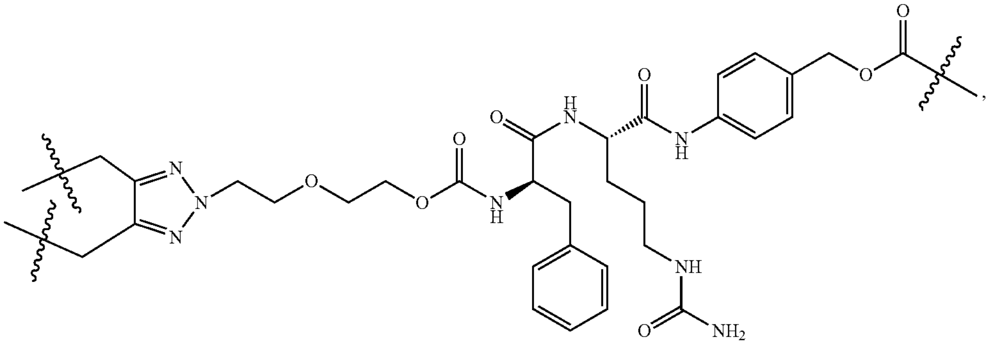
,
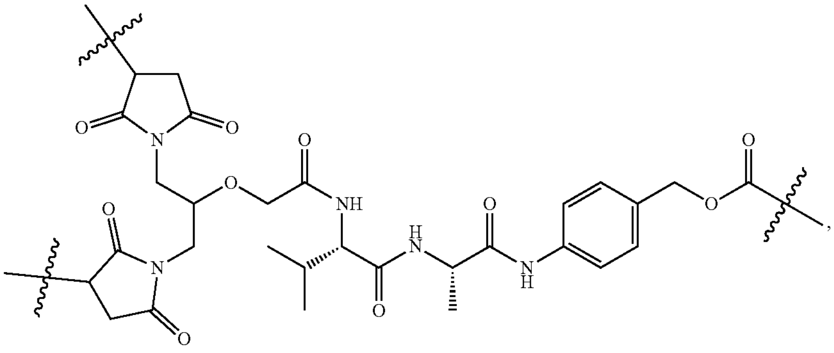
,
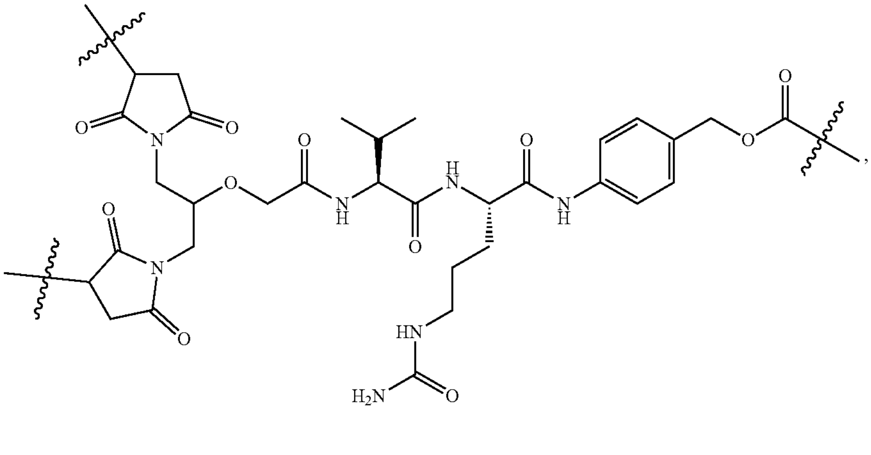
, -continued
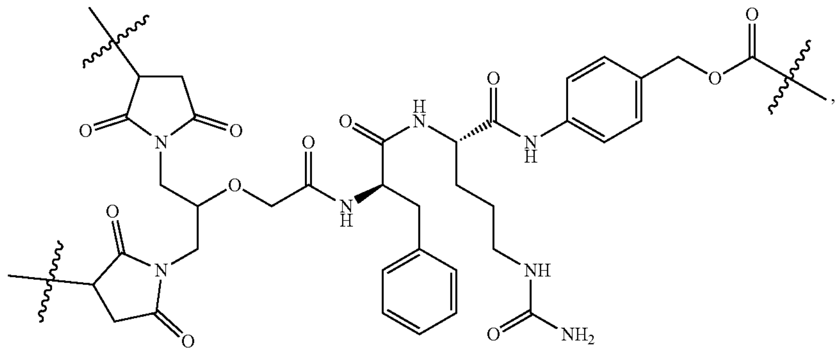
,
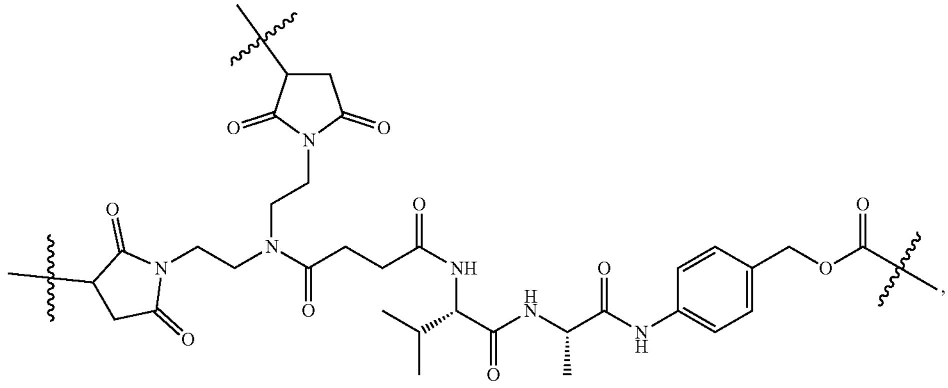
,
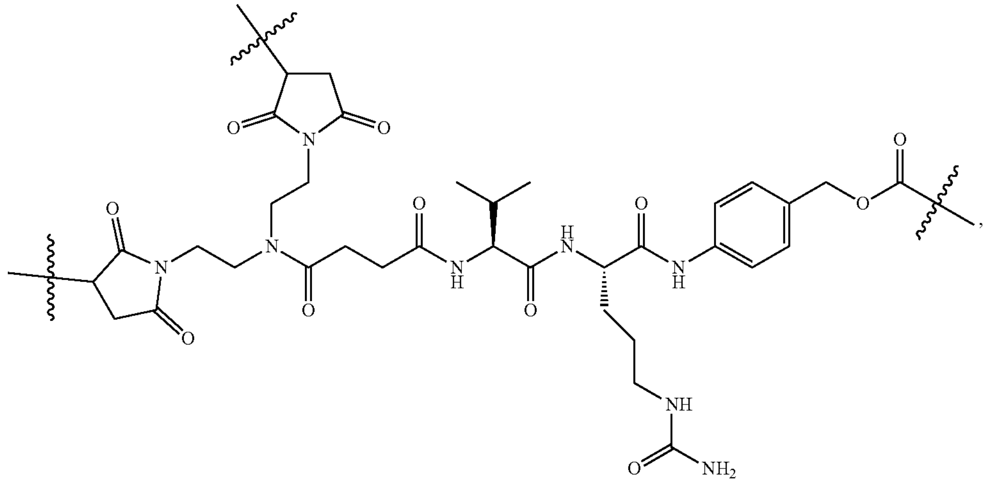
,
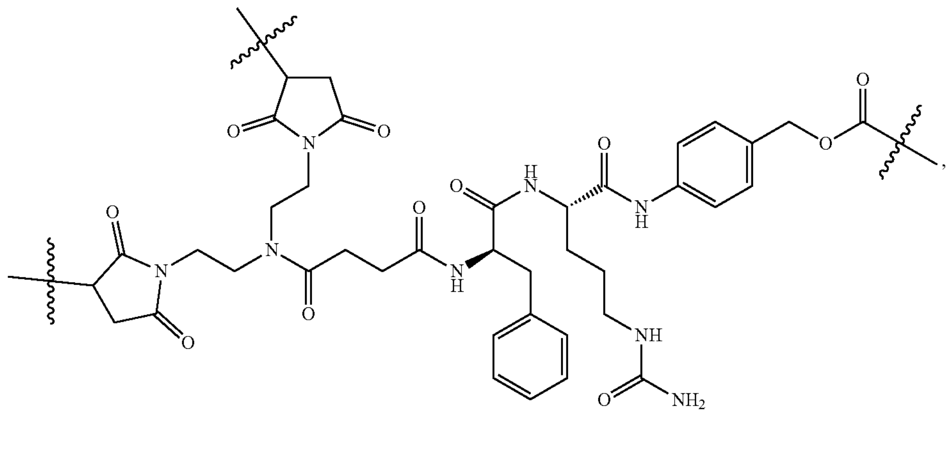
, -continued

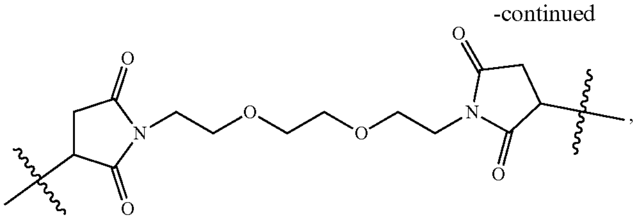

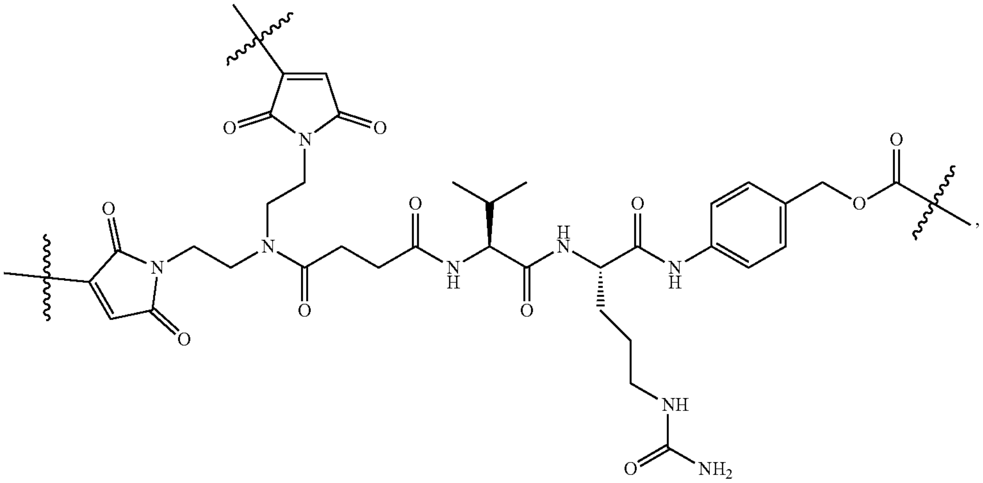

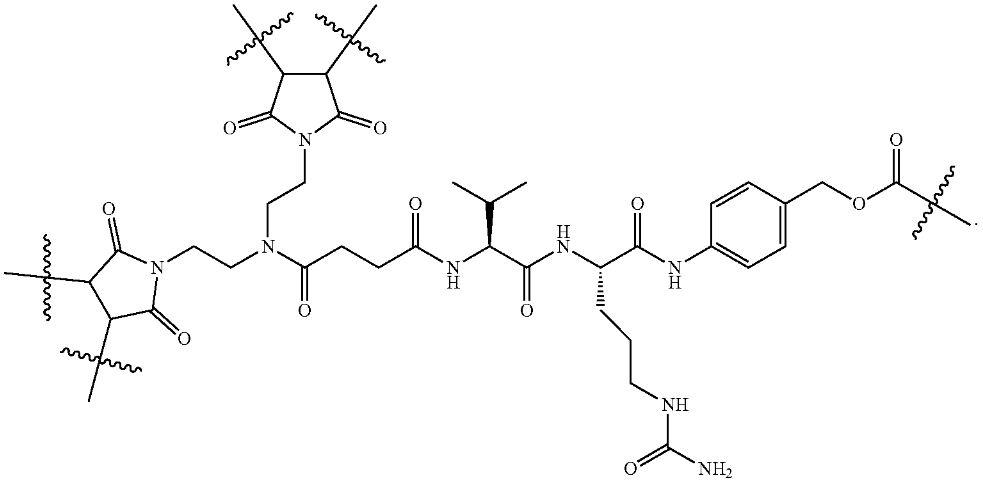

19. The antibody-drug conjugate according to claim 14, wherein L is covalently linked to the thiol residue on A.

20. The antibody-drug conjugate according to claim 14, wherein L is covalently linked to the thiol residue formed after the interchain disulfide bond on A is opened.

21. The antibody-drug conjugate according to claim 13, wherein U has a structure selected from the group consisting of:

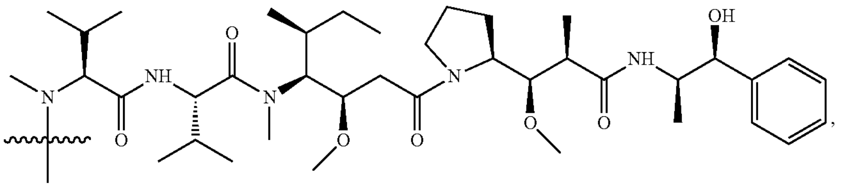

-continued
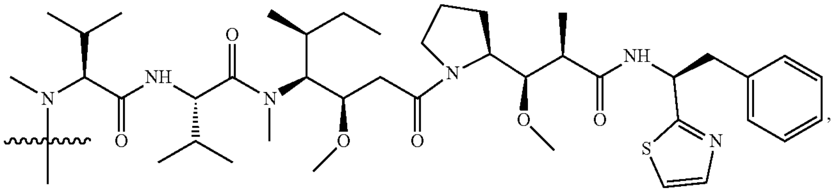,
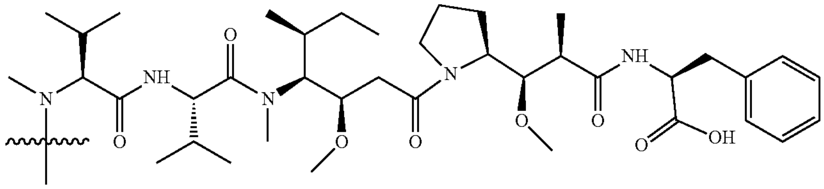,
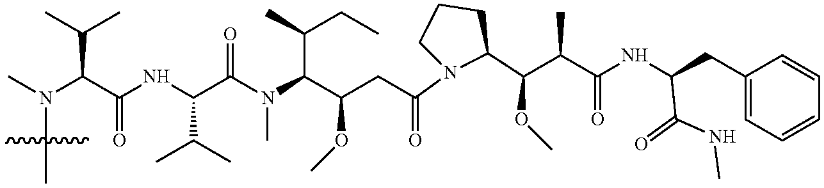,
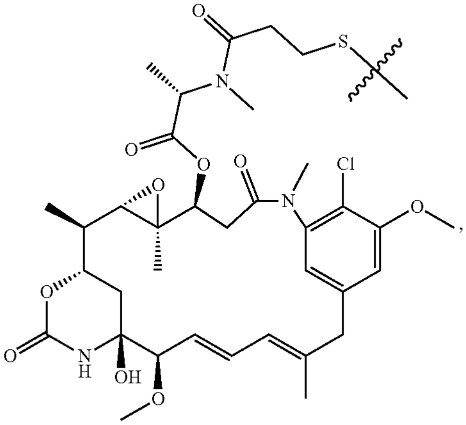,
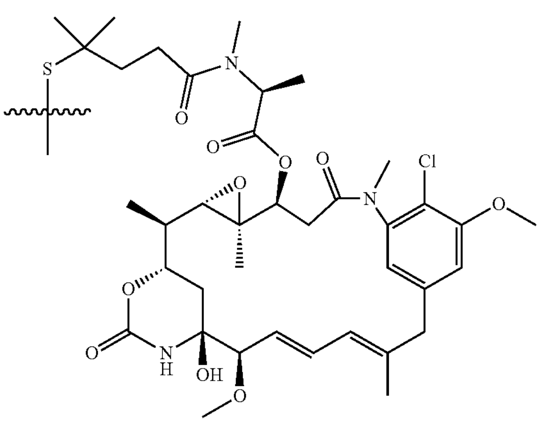,
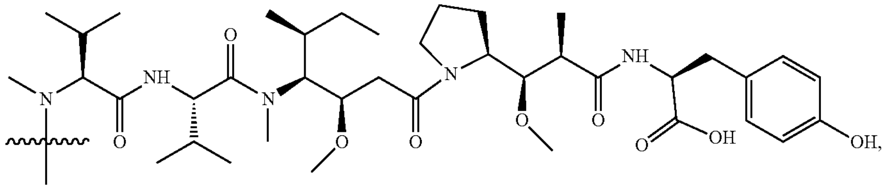
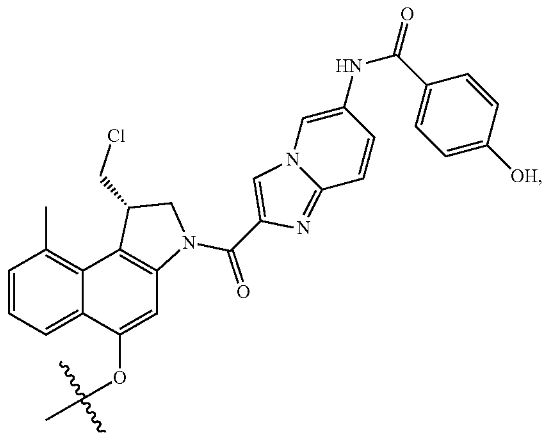

-continued
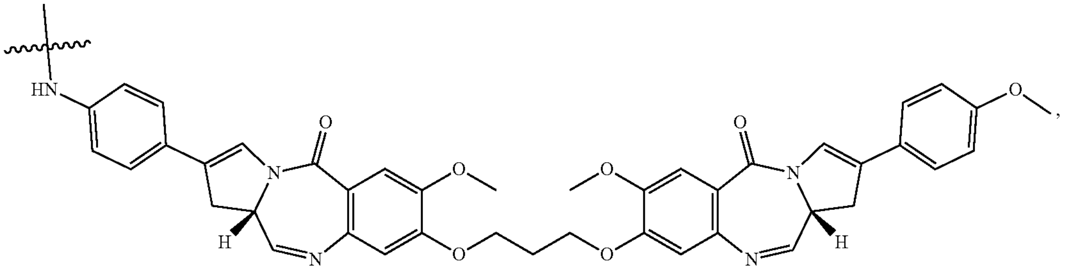
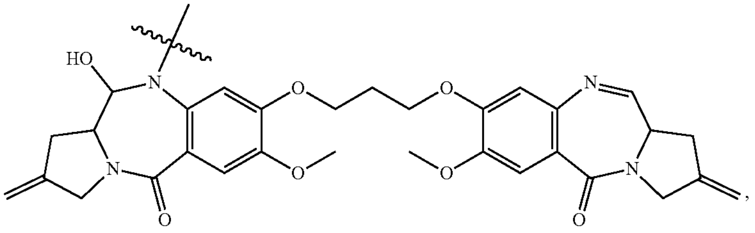
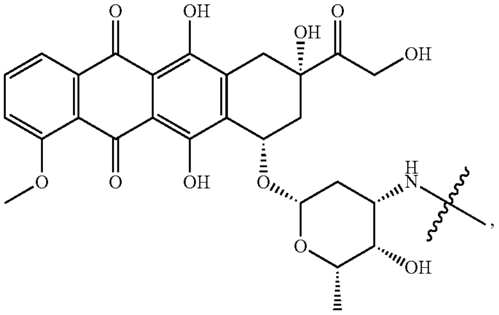
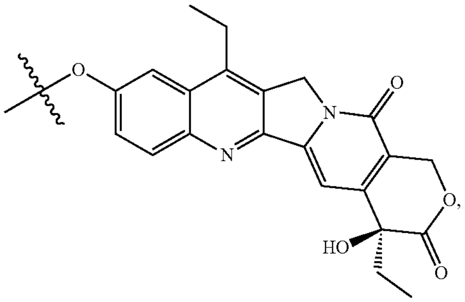
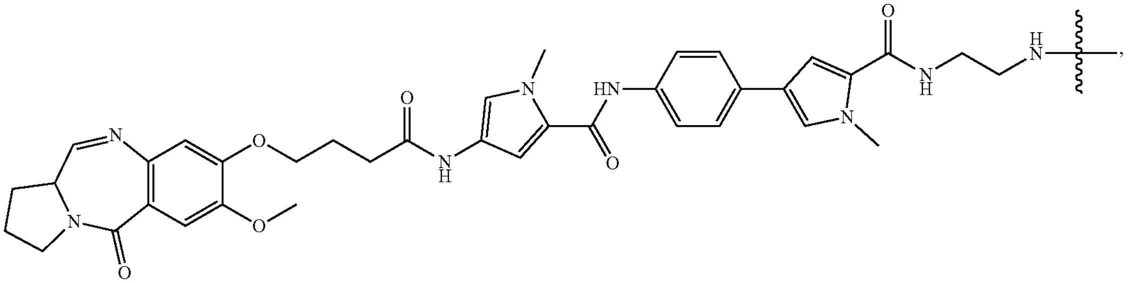
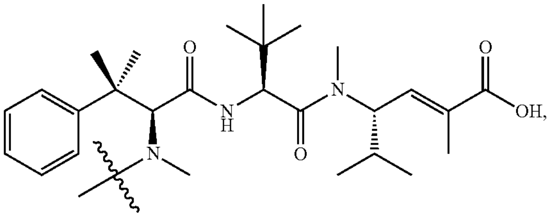
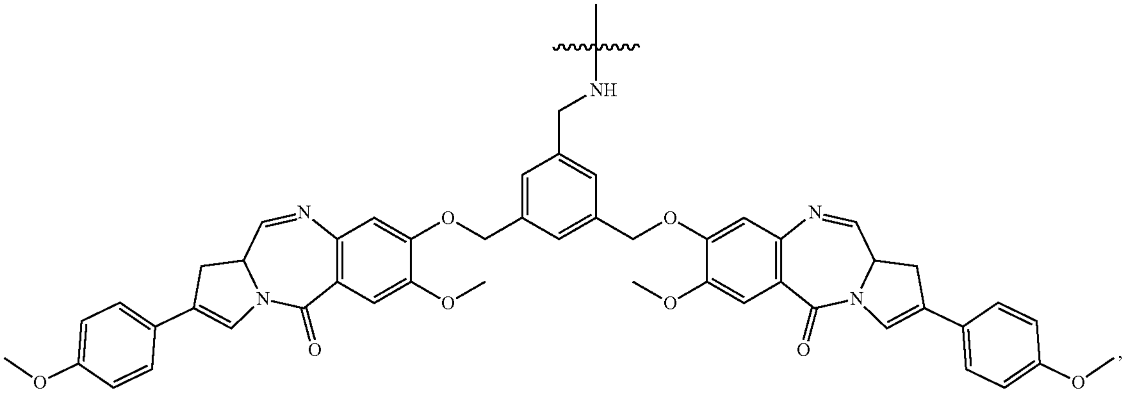

-continued
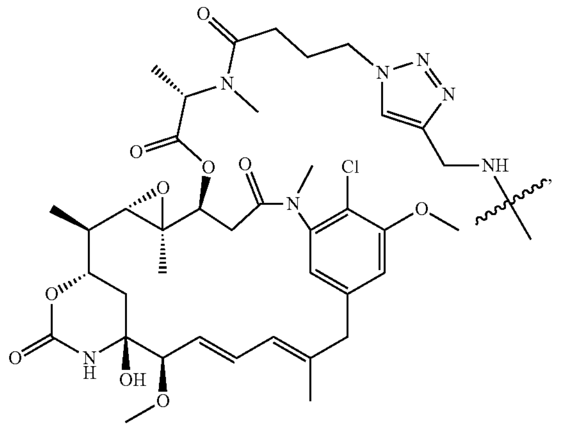
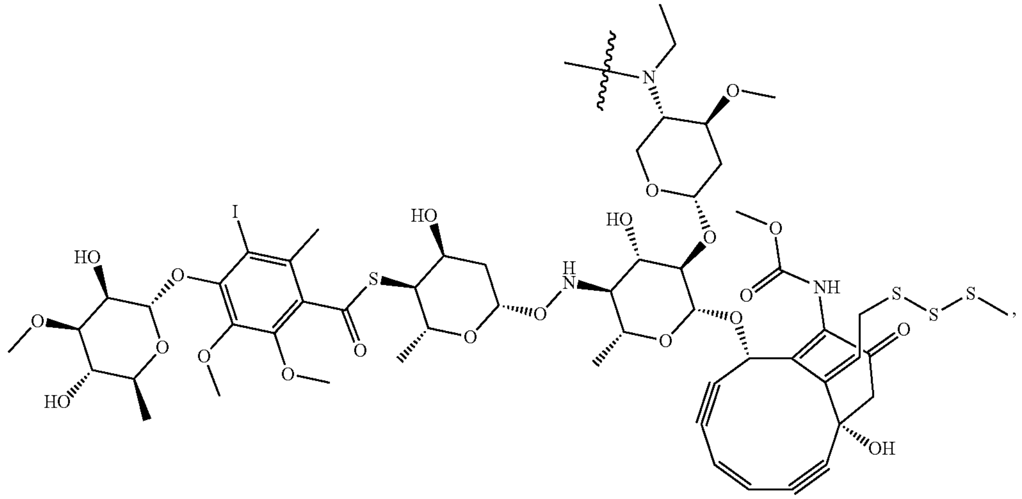
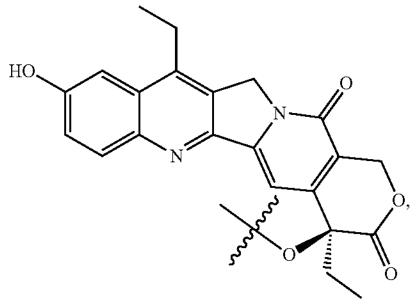
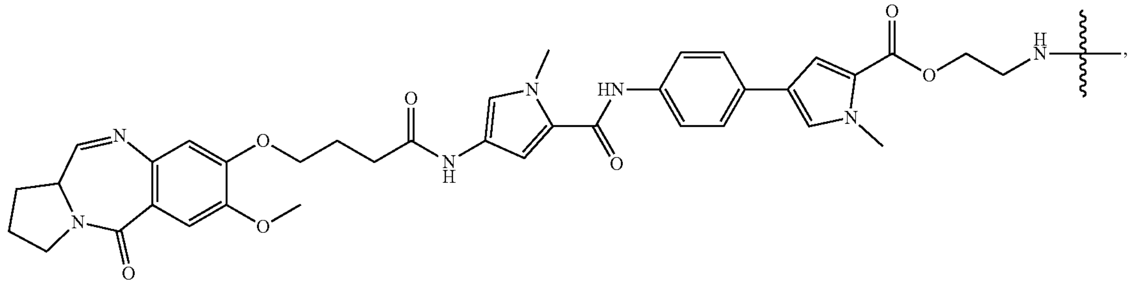

-continued
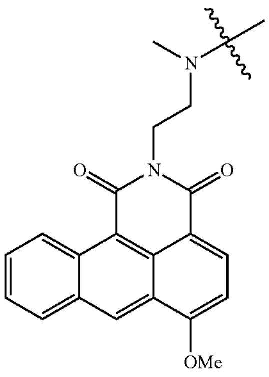
,
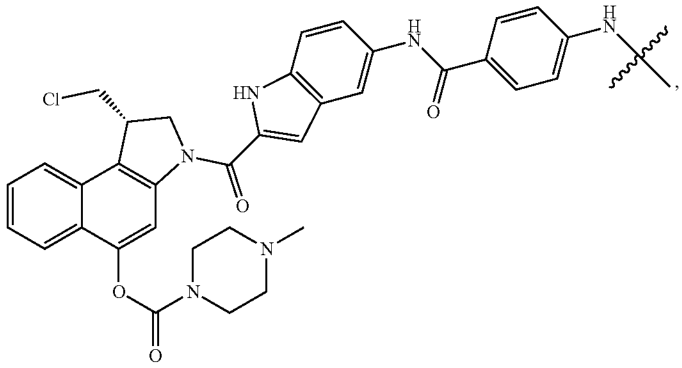
,
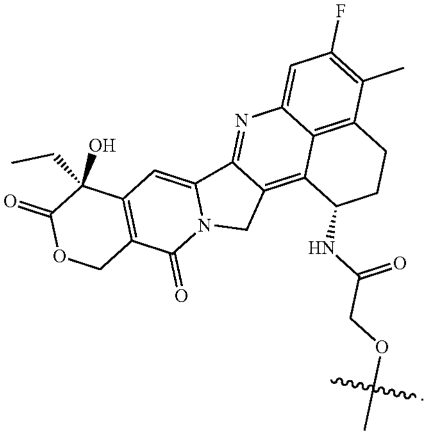
.
22. The antibody-drug conjugate according to claim 13, wherein the antibody-drug conjugate has a structure selected from the group consisting of:
ADC-1
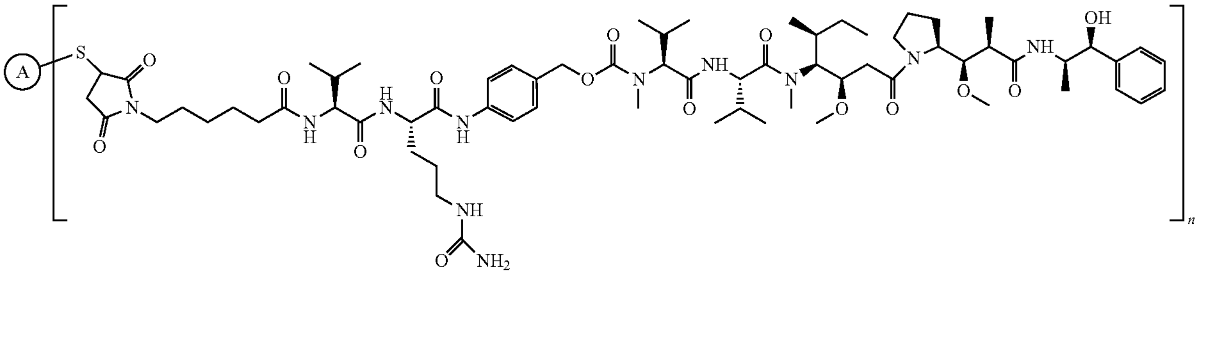

wherein, n in ADC-1 is an integer selected from 1, 2, 3, 4, 5, 6, 7 and 8; or
ADC-2
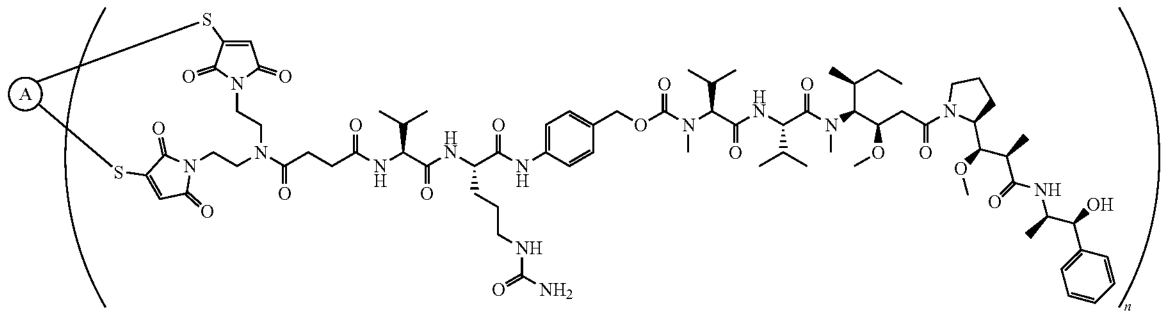
wherein, n in ADC-2 is an integer selected from 1, 2, 3 and 4; or
ADC-3
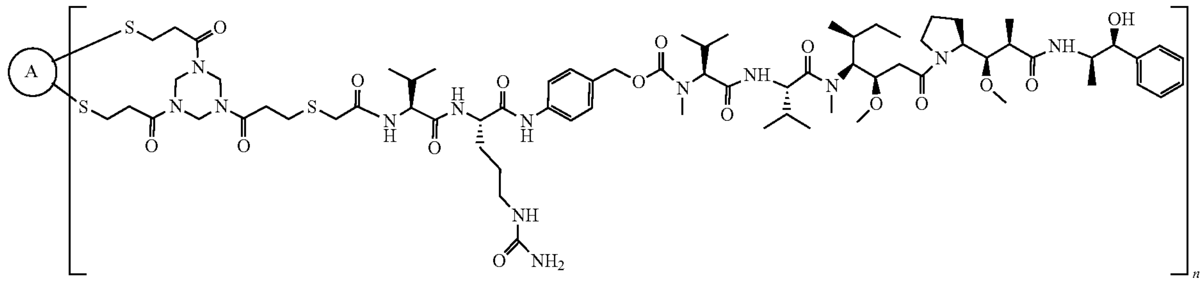
wherein, n in ADC-3 is an integer selected from 1, 2, 3 and 4; or
ADC-4
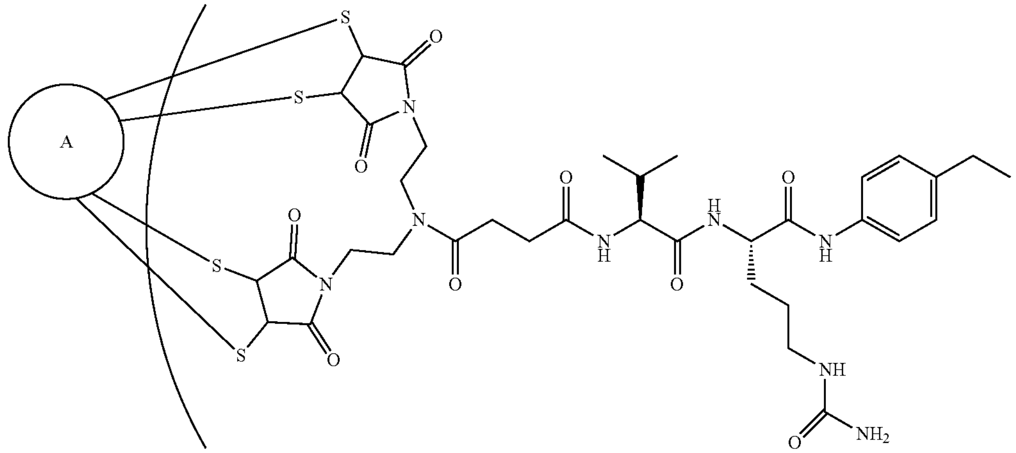

-continued
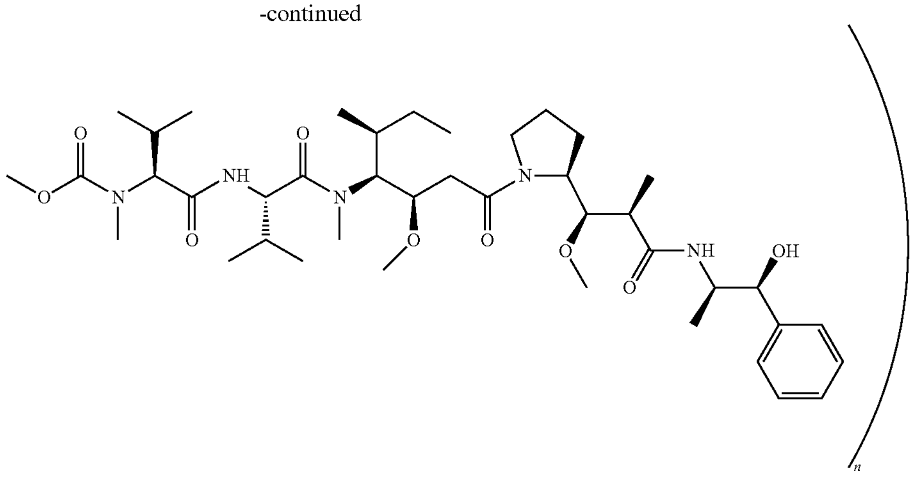
wherein, n in ADC-4 is an integer selected from 1 and 2; or
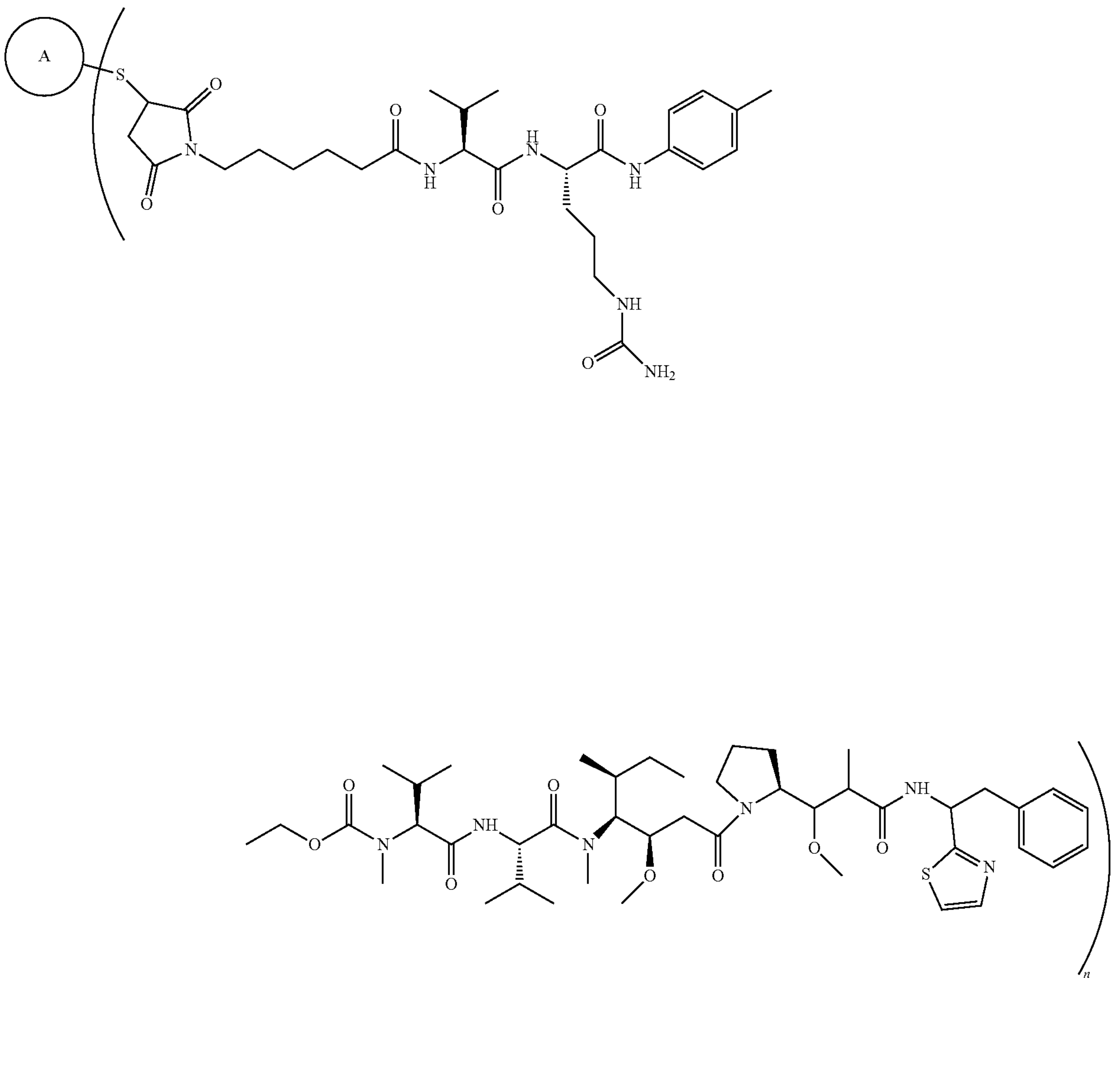

wherein, n in ADC-5 is an integer selected from 1, 2, 3, 4, 5, 6, 7 and 8; or

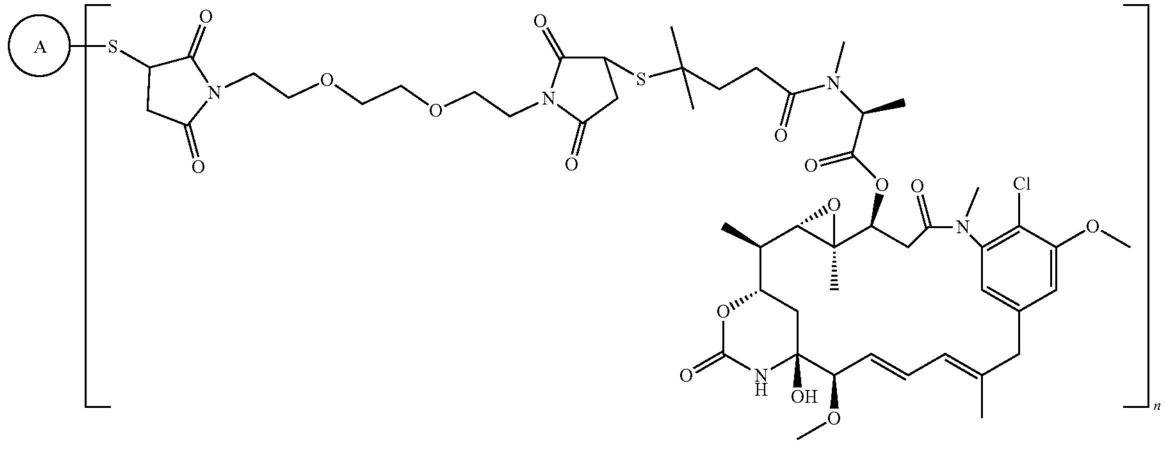

wherein, n in ADC-6 is an integer selected from 1, 2, 3, 4, 5, 6, 7 and 8; or

ADC-7

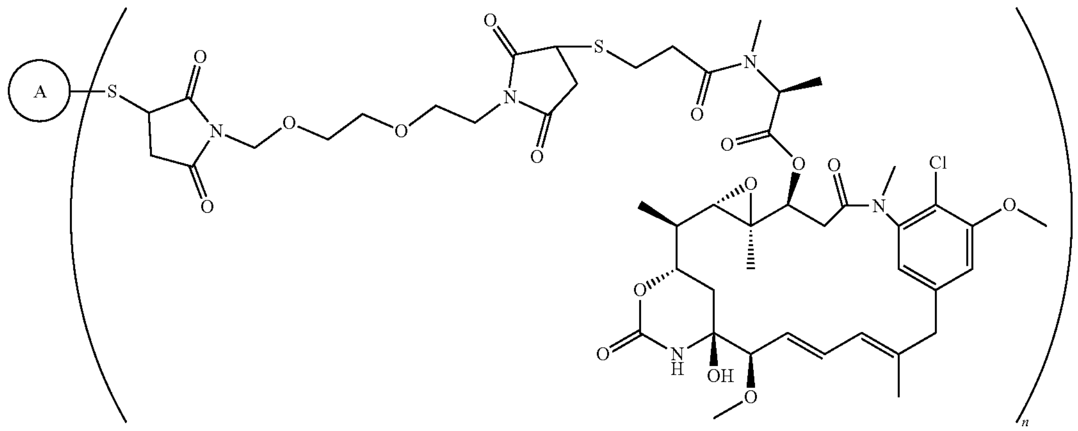

wherein, n in ADC-7 is an integer selected from 1, 2, 3, 4, 5, 6, 7 and 8.

23. The antibody-drug conjugate according to claim 12, wherein the tubulin inhibitor is selected from the group consisting of a cytotoxic molecule of dolastatins and auristatins and a cytotoxic molecule of maytansines; the DNA damaging agent is selected from the group consisting of calicheamicins, duocarmycins, pyrrolobenzodiazepine derivatives (PBD), camptothecins and derivatives thereof, SN-38 and Dxd.

24. The antibody-drug conjugate according to claim 12, wherein the cytotoxic molecule of auristatins is selected from the group consisting of MMAE, MMAF, and a derivative thereof, and the cytotoxic molecule of maytansines is selected from the group consisting of DM1, DM4, and a derivative thereof.

25. A pharmaceutical composition comprising the antibody-drug conjugate according to claim 11, and a pharmaceutically acceptable carrier.

26. A method for treating a disease comprising administering a therapeutically effective amount of the antibody-drug conjugate according to claim 11 to a patient in need thereof, wherein the disease is a c-Met positive cancer.

27. The method according to claim 26, wherein the disease is lung cancer or gastric cancer.

28. A kit comprising a container and a preparation placed in the container; wherein the preparation comprises the antibody-drug conjugate according to claim 11 or a pharmaceutically acceptable salt or solvate thereof.

29. A pharmaceutical composition comprising the antibody or antigen-binding fragment thereof according to claim 1, and a pharmaceutically acceptable carrier.

30. A kit comprising a container and a preparation placed in the container; wherein the preparation comprises the pharmaceutical composition according to claim 29.

31. A kit comprising a container and a preparation placed in the container; wherein the preparation comprises the antibody or antigen-binding fragment thereof according to claim 1.

32. A recombinant protein comprising the antibody or antigen-binding fragment according to claim 1.

33. A method of manufacturing a recombinant protein, comprising using the antibody or antigen-binding fragment according to claim 1.

* * * * *

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: The sequence is synthesized

<400> SEQUENCE: 1

Ser Tyr Trp Met His
1               5


<210> SEQ ID NO 2
<211> LENGTH: 17
<212> TYPE: PRT
<213> ORGANISM: Artificial Sequence
<220> FEATURE:
<223> OTHER INFORMATION: The sequence is synthesized

<400> SEQUENCE: 2

Met Ile Asp Pro Ser Asp Ser Glu Ser Arg Leu Asn Gln Lys Phe Lys
1               5                   10                  15

Asp


<210> SEQ ID NO 3
<211> LENGTH: 13
<212> TYPE: PRT
<213> ORGANISM: Artificial Sequence
<220> FEATURE:
<223> OTHER INFORMATION: The sequence is synthesized

<400> SEQUENCE: 3

Ser Gly Tyr His Gly Thr Ser Tyr Trp Tyr Phe Asp Val
1               5                   10


<210> SEQ ID NO 4
<211> LENGTH: 16
<212> TYPE: PRT
<213> ORGANISM: Artificial Sequence
<220> FEATURE:
<223> OTHER INFORMATION: The sequence is synthesized

<400> SEQUENCE: 4

Arg Ser Ser Lys Ser Leu Leu His Ser Asp Gly Ile Thr Tyr Leu Tyr
1               5                   10                  15


<210> SEQ ID NO 5
<211> LENGTH: 7
<212> TYPE: PRT
```

-continued

<213> ORGANISM: Artificial Sequence
<220> FEATURE:
<223> OTHER INFORMATION: The sequence is synthesized

<400> SEQUENCE: 5

Gln Met Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: The sequence is synthesized

<400> SEQUENCE: 6

Ala Gln Asn Leu Glu Leu Pro Pro Thr
1               5

<210> SEQ ID NO 7
<211> LENGTH: 122
<212> TYPE: PRT
<213> ORGANISM: Artificial Sequence
<220> FEATURE:
<223> OTHER INFORMATION: The sequence is synthesized

<400> SEQUENCE: 7

Gln Val Gln Leu Glu Gln Ser Gly Pro Glu Val Val Lys Pro Gly Ala
1               5                   10                  15

Ser Val Lys Val Ser Cys Lys Ala Ser Gly Tyr Ser Phe Thr Ser Tyr
            20                  25                  30

Trp Met His Trp Val Arg Gln Ala Pro Gly Gln Gly Leu Glu Trp Met
        35                  40                  45

Gly Met Ile Asp Pro Ser Asp Ser Glu Ser Arg Leu Asn Gln Lys Phe
    50                  55                  60

Lys Asp Arg Val Thr Met Thr Val Asp Thr Pro Thr Ser Thr Val Tyr
65                  70                  75                  80

Met Glu Leu Ser Ser Pro Arg Ser Glu Asp Thr Ala Val Tyr Tyr Cys
                85                  90                  95

Ala Arg Ser Gly Tyr His Gly Thr Ser Tyr Trp Tyr Phe Asp Val Trp
            100                 105                 110

Gly Gln Gly Thr Leu Val Thr Val Ser Ser
        115                 120

<210> SEQ ID NO 8
<211> LENGTH: 115
<212> TYPE: PRT
<213> ORGANISM: Artificial Sequence
<220> FEATURE:
<223> OTHER INFORMATION: The sequence is synthesized

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asp Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile

```
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Val Glu Ile Lys
            100                 105                 110

Arg Thr Val
        115


<210> SEQ ID NO 9
<211> LENGTH: 452
<212> TYPE: PRT
<213> ORGANISM: Artificial Sequence
<220> FEATURE:
<223> OTHER INFORMATION: The sequence is synthesized

<400> SEQUENCE: 9

Gln Val Gln Leu Glu Gln Ser Gly Pro Glu Val Val Lys Pro Gly Ala
1               5                   10                  15

Ser Val Lys Val Ser Cys Lys Ala Ser Gly Tyr Ser Phe Thr Ser Tyr
            20                  25                  30

Trp Met His Trp Val Arg Gln Ala Pro Gly Gln Gly Leu Glu Trp Met
        35                  40                  45

Gly Met Ile Asp Pro Ser Asp Ser Glu Ser Arg Leu Asn Gln Lys Phe
    50                  55                  60

Lys Asp Arg Val Thr Met Thr Val Asp Thr Pro Thr Ser Thr Val Tyr
65                  70                  75                  80

Met Glu Leu Ser Ser Pro Arg Ser Glu Asp Thr Ala Val Tyr Tyr Cys
                85                  90                  95

Ala Arg Ser Gly Tyr His Gly Thr Ser Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
```

-continued

```
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 10
<211> LENGTH: 219
<212> TYPE: PRT
<213> ORGANISM: Artificial Sequence
<220> FEATURE:
<223> OTHER INFORMATION: The sequence is synthesized

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asp Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

-continued

```
Pro Val Thr Lys Ser Phe Asn Arg Gly Glu Cys
    210                 215
```